US009255929B2

(12) United States Patent
Jiang et al.

(10) Patent No.: US 9,255,929 B2
(45) Date of Patent: Feb. 9, 2016

(54) ZWITTERIONIC POLYMERS HAVING BIOMIMETIC ADHESIVE LINKAGES

(75) Inventors: Shaoyi Jiang, Redmond, WA (US); Changlu Gao, Fukuoka (JP); Guozhu Li, Shanghai (CN); Hong Xue, Seattle, WA (US); Norman David Brault, Jr., Seattle, WA (US)

(73) Assignee: University of Washington, Seattle, WA (US)

( * ) Notice: Subject to any disclaimer, the term of this patent is extended or adjusted under 35 U.S.C. 154(b) by 1304 days.

(21) Appl. No.: 12/891,524

(22) Filed: Sep. 27, 2010

(65) Prior Publication Data

US 2011/0105712 A1    May 5, 2011

Related U.S. Application Data

(60) Provisional application No. 61/245,892, filed on Sep. 25, 2009.

(51) Int. Cl.
*C08F 118/02* (2006.01)
*G01N 33/68* (2006.01)

(52) U.S. Cl.
CPC .................. *G01N 33/6845* (2013.01)

(58) Field of Classification Search
CPC .... C08F 120/34; C08F 120/38; C08F 120/56; C08F 120/60; C08F 293/005; C08L 33/06; C08L 33/14; C08L 33/26
USPC .................................................. 526/319, 304
See application file for complete search history.

(56) References Cited

U.S. PATENT DOCUMENTS

| | | | |
|---|---|---|---|
| 3,671,502 A | 6/1972 | Samour | |
| 4,138,446 A | 2/1979 | Kawakami | |
| 5,204,060 A | 4/1993 | Allenmark | |
| 5,919,523 A | 7/1999 | Sundberg | |
| 6,361,768 B1 | 3/2002 | Galleguillos | |
| 6,486,333 B1 | 11/2002 | Murayama | |
| 6,897,263 B2 | 5/2005 | Hell | |
| 7,291,427 B2 | 11/2007 | Kawamura | |
| 7,306,625 B1 | 12/2007 | Stratford | |
| 7,335,248 B2 | 2/2008 | Abou-Nemeh | |
| 7,737,224 B2 | 6/2010 | Willis | |
| 2005/0058689 A1 | 3/2005 | McDaniel | |
| 2008/0045420 A1* | 2/2008 | Karagianni et al. | 507/121 |
| 2008/0139746 A1* | 6/2008 | Pacetti | 525/188 |

FOREIGN PATENT DOCUMENTS

| | | |
|---|---|---|
| DE | 10 2006 004 111 A1 | 8/2007 |
| EP | 0 354 984 A2 | 2/1990 |
| EP | 0 419 654 A1 | 4/1991 |
| EP | 0 479 245 A2 | 4/1992 |
| JP | 63-234007 A | 9/1988 |
| SU | 1780673 A1 | 12/1992 |
| WO | 00/39176 A1 | 7/2000 |
| WO | 2004/058837 A2 | 7/2004 |
| WO | 2004/100666 A1 | 11/2004 |
| WO | 2008/083390 A1 | 12/2008 |
| WO | 2009/067562 A1 | 5/2009 |

OTHER PUBLICATIONS

Li et al., "Ultra low fouling zwitterionic polymers with a biomimetic adhesive group", Biomaterials 29 (2008) 4592-4597).*
Chen, S., et al., "Controlling Antibody Orientation on Charged Self-Assembled Monolayers," Langmuir 19(7):2859-2864, Apr. 2003.
Chen, S., et al., "Strong Resistance of Oligo(phosphorylcholine) Self-Assembled Monolayers to Protein Adsorption," Langmuir 22(6):2418-2421, Mar. 2006.
Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.
Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.
Feng., W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.
Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.
Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.
Li, L., et al., "Protein Adsorption on Alkanethiolate Self-Assembled Monolayers: Nanoscale Surface Structural and Chemical Effects," Langmuir 19(7):2974-2982, Apr. 2003.
Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.
Lowe, A.B., et al., "Well-Defined Sulfobetaine-Based Statistical Copolymers as Potential Antibioadherent Coatings," Journal of Biomedical Materials Research 52(1):88-94, Jul. 2000.
West, S.L., et al., "The Biocompatibility of Crosslinkable Copolymer Coatings Containing Sulfobetaines and Phosphobetaines," Biomaterials 25:1195-1204, Apr. 2004.
Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

(Continued)

*Primary Examiner* — Kuo-Liang Peng
(74) *Attorney, Agent, or Firm* — Christensen O'Connor Johnson Kindness PLLC

(57) ABSTRACT

Zwitterionic polymers having adhesive groups, methods for making the polymers, surfaces having the polymers grafted thereto and grafted therefrom, and methods for making and using the polymer-modified surfaces.

13 Claims, 30 Drawing Sheets
(16 of 30 Drawing Sheet(s) Filed in Color)

(56) References Cited

OTHER PUBLICATIONS

Yuan, J., et al., "Improvement of Blood Compatibility on Cellulose Membrane Surface by Grafting Betaines," Colloids and Surfaces B: Biointerfaces 30(1-2):147-155, Jul. 2003.
Yuan, J., "Platelet Adhesion Onto Segmented Polyurethane Surfaces Modified by Carboxybetaine," Journal of Biomaterial Science, Polymer Edition 14(12):1339-1349, Dec. 2003.
Yuan, Y., et al., "Grafting Sulfobetaine Monomer Onto Silicone Surface to Improve Haemocompatability," Polymer International 53(1):121-126, Jan. 2004.
Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.
Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.
Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.
Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.
Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.
Zhang, Z., et al., "Superflow Fouling Sulfobetaine and Carboxybetaine Polymers on Glass Slides," Langmuir 22(24):10072-10077, Nov. 2006.
Zhang, Z., "Surface Grafted Sulfobetaine Polymers Via Atom Transfer Radical Polymerization as Superlow Fouling Coatings," Journal of Physical Chemistry B 110(22)10799-10804, Jun. 2006.
Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.
Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.
Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.
Granéli, A., et al., "Formation of Supported Lipid Bilayer Membranes on $SiO_2$ From Proteoliposomes Containing Transmembrane Proteins," Langmuir 19(3):842-850, Feb. 2003.
Gu, H., et al., "Synthesis and Cellular Uptake of Porphyrin Decorated Iron Oxide Nanoparticles—A Potential Candidate for Bimodal Anticancer Therapy," Chemical Communications, 14(34):4270-4272, Sep. 2005.
Gupta, A., et al., "Single Virus Particle Mass Detection Using Microresonators With Nanoscale Thickness," Applied Physics Letters 84(11):1976-1978, Mar. 2004.
Hanash, S.M., et al., "Mining the Plasma Proteome for Cancer Biomarkers," Nature 452(7187):571-579, Apr. 2008.
Heydorn, A., et al., "Quantification of Biofilm Structures by the Novel Computer Program COMSTAT," Journal of General Microbiology 146(Pt 10):2395-2407, Oct. 2000.
Hirota, K., et al., "Coating of a Surface With 2-Methacryloyloxyethyl Phosphorylcholine (MPC) Co-Polymer Significantly Reduces Retention of Human Pathogenic Microorganisms," Federation of European Microbiological Societies (FEMS) Microbiology Letters 248(1):37-45, Jul. 2005.
Holmlin, R.E., et al., "Zwitterionic SAMs That Resist Nonspecific Adsorption of Protein From Aqueous Buffer," Langmuir 17(9):2841-2850, May 2001.
Homola, J., "Surface Plasmon Resonance Sensors for Detection of Chemical and Biological Species," Chemical Reviews 108(2):462-493, Feb. 2008.
Homola, J., "On the Sensitivity of Surface Plasmon Resonance Sensors With Spectral Interrogation," Sensors and Actuators B: Chemical 41(1-3):207-211, Jun. 1997.
Homola, J., "Spectral Surface Plasmon Resonance Biosensor for Detection of Staphylococcal enterotoxin B in Milk," International Journal of Food Microbiology 75(1-2):61-69, May 2002.
Huang, . N -P., et al., "Biotin-Derivatized Poly(L-lysine)-g-poly(ethylene glycol): A Novel Polymeric Interface for Bioaffinity Sensing," Langmuir 18(1):220-230, Jan. 2002.
Hwang, K.S., et al., "Nanomechanical Microcantilever Operated in Vibration Modes With Use of RNA Aptamer as Receptor Molecules for Label-Free Detection of HCV Helicase," Biosensors and Bioelectronics 23(4):459-465, Nov. 2007.
Ibraeva, Z.E., et al., "Solution Properties and Complexation of Polyampholytes Based on N,N-Dimethyldiallyl-ammonium Chloride and Maleic Acid or Alkyl (Aryl) Derivatives of Maleamic Acids," Macromolecular Chemistry and Physics 205(18):2464-2472, Dec. 2004.
Ikeuchi, M., et al., "A New Synthesis of Phenolic 1-Hydroxy-1-phenyl-2,3,4,5-tetrahydro-1H-3-benzazepines," HeteroCycles 65(12):2925-2935, 2005.
Ishihara, K., et al., "Protein Adsorption From Human Plasma Is Reduced on Phospholipid Polymers," Journal of Biomedical Materials Research 25(11):1397-1407, Nov. 1991.
Jiang, S., and Z. Cao, "Ultralow-Fouling, Functionalizable, and Hydrolyzable Zwitterionic Materials and Their Derivatives for Biological Applications," Advanced Materials 22(9):920-932, Mar. 2010.
Johnston, E.E., et al., "Interactions Between Pseudomonas aeruginosa and Plasma-Deposited PEO-Like Thin Films During Initial Attachment and Growth," Polymer Preprints 38:1016-1017, Apr. 1997.
Jones, D.M., et al., "Surface-Initiated Polymerizations in Aqueous Media: Effect of Initiator Density," Langmuir 18(4):1265-1269, Feb. 2002.
Jun, Y.-W., et al., "Nanoscale Size Effect of Magnetic Nanocrystals and Their Utilization for Cancer Diagnosis via Magnetic Resonance Imaging," Journal of the American Chemical Society 127(16):5732-5733, Apr. 2005.
Kenausis, G.L., et al., "Poly(l-lysine)-g-Poly(ethylene glycol) Layers on Metal Oxide Surfaces: Attachment Mechanism and Effects of Polymer Architecture on Resistance to Protein Adsorption," Journal of Physical Chemistry B 104(14):3298-3309, Apr. 2000.
Kim, S.K., et al., "Nanogap Biosensors for Electrical and Label-Free Detection of Biomolecular Interactions," Nanotechnology 20(45):45502/1-45502/7, Nov. 2009.
Klibanov, A.M., et al., "Permanently Microbicidal Materials Coatings," Journal of Materials Chemistry 17(24):2479-2482, 2007.
Klueh U. et al., "Efficacy of Silver-Coated Fabric to Prevent Bacterial Colonization and Subsequent Device-Based Biofilm Formation," Journal of Biomedical Materials Research 53(6):621-631, 2000.
Ladd, J., et al., "DNA-Directed Protein Immobilization on Mixed Self-Assembled Monolayers via a Streptavidin Bridge," Langmuir 20(19):8090-8095, Sep. 2004.
Ladd, J., et al., "Zwitterionic Polymers Exhibiting High Resistance to Nonspecific Protein Adsorption From Human Serum and Plasma," Biomacromolecules 9(5):1357-1361, May 2008.
Lang, H.P., et al., "Sequential Position Readout From Arrays of Micromechanical Cantilever Sensors," Applied Physics Letters 72(3):383-385, Jan. 1998.
Lee, B.S., et al., "Functionalization of Poly(oligo(ethylene glycol)methacrylate) Films on Gold and $Si/SiO_2$ for Immobilization of Proteins and Cells: SPR and QCM Studies," Biomacromolecules 8(12):3922-3929, Dec. 2007.
Lee, H., et al., "A Reversible Wet/Dry Adhesive Inspired by Mussels and Geckos," Nature 448(7151):338-342, Jul. 2007.
Lee, H., et al., "Mussel-Inspired Surface Chemistry for Multifunctional Coatings," Science 318(5849):426-430, Oct. 2007.
Lee, H., et al., "Single-Molecule Mechanics of Mussel Adhesion," Proceedings of the National Academy of Sciences USA (PNAS) 103(35):12999-13003, Aug. 2006.
Lee, H.-Y. et al. (2008) "Synthesis and Characterization of PVP-Coated Large Core Iron Oxide Nanoparticles as an MRI Contrast

(56) References Cited

OTHER PUBLICATIONS

Agent," Nanotechnology 19(16):165101, Apr. 2008. (Author Manuscript PMCID: PMC3050625, available in PMC Mar. 8, 2011, 14 pages).
Li, G., et al., "Ultralow Fouling Zwitterionic Polymers Grafted from Surfaces Covered With an Initiator via an Adhesive Mussel Mimetic Linkage," Journal of Physical Chemistry B 112:15269-15274, Dec. 2008.
Li, M., et al., "Ultra-Sensitive NEMS-Based Cantilevers for Sensing, Scanned Probe and Very High-Frequency Applications," Nature Nanotechnology 2(2):114-120, Feb. 2007.
Ligler, F.S., "Perspective on Optical Biosensors and Integrated Sensor Systems," Analytical Chemistry 81(2):519-526, Jan. 2009.
Lin, Q., et al., "Adhesion Mechanisms of the Mussel Foot Proteins mfp-1 and mfp-3," Proceedings of the National Academy of Sciences USA (PNAS) 104(10):3782-3786, Mar. 2007.
Liu, F., et al., "Automated in Vivo Segmentation of Carotid Plaque MRI With Morphology-Enhanced Probability Maps," Magnetic Resonance in Medicine 55(3):659-668, Mar. 2006.
Luk, Y.-Y., et al., "Self-Assembled Monolayers of Alkanethiolates Presenting Mannitol Groups Are Inert to Protein Adsorption and Cell Attachment," Langmuir 16(24):9604-9608, Nov. 2000.
Ma, H., et al., "'Non-Fouling' Oligo(ethylene glycol)-Functionalized Polymer Brushes Synthesized by Surface-Initiated Atom Transfer Radical Polymerization," Advanced Materials 16(4):338-341, Feb. 2004.
McArthur, S.L., et al., "Effect of Polysaccharide Structure on Protein Adsorption," Colloids and Surfaces B: Biointerfaces 17(1):37-48, Jan. 2000.
McCarthy, J.R., et al., "Targeted Delivery of Multifunctional Magnetic Nanoparticles," Nanomedicine 2(2):153-167, Apr. 2007.
Messersmith, P.B.,"Multitasking in Tissues and Materials," Science 319(5871):1767-1768, Mar. 2008.
Mrksich, M., and G.M. Whitesides, "Using Self-Assembled Monolayers to Understand the Interactions of Man-Made Surfaces With Proteins and Cells," Annual Review of Biophysics and Biomolecular Structure 25:55-78, 1996.
Nejadnik, M.R., et al., "Bacterial Adhesion and Growth on a Polymer Brush-Coating," Biomaterials 29(30):4117-4121, Oct. 2008.
Ooka, A.A., and R.L. Garrell, "Surface-Enhanced Raman Spectroscopy of DOPA-Containing Peptides Related to Adhesive Protein of Marine Mussel, Mytilus edulis," Biopolymers 57(2):92-102, 2000.
Ostuni, E., et al., "Self-Assembled Monolayers That Resist the Adsorption of Proteins and the Adhesion of Bacterial and Mammalian Cells," Langmuir 17(20):6336-6343, Oct. 2001.
Park, I.-K., et al.,"Determination of Nanoparticle Vehicle Unpackaging by MR Imaging of a T-2 Magnetic Relaxation Switch," Biomaterials 29(6):724-732, Feb. 2008.
Patel, J.D., et al., "Phospholipid Polymer Surfaces Reduce Bacteria and Leukocyte Adhesion Under Dynamic Flow Conditions," Journal of Biomedical Materials Research Part A 73(3):359-366, Jun. 2005.
Paulovich, A.G., et al., "The Interface Between Biomarker Discovery and Clinical Validation: The Tar Pit of the Protein Biomarker Pipeline," Proteomics—Clinical Applications 2(10-11):1386-1402, Oct. 2008.
Polyak, B., et al., "High Field Gradient Targeting of Magnetic Nanoparticle-Loaded Endothelial Cells to the Surfaces of Steed Stents," Proceedings of the National Academy of Sciences USA (PNAS) 105(2):698-703, Jan. 2008.
Abdiche, Y., et al., "Determining Kinetics and Affinities of Protein Interactions Using a Parallel Real-Time Label-Free Biosensor, the Octet," Analytical Biochemistry 377(2):209-217, Jun. 2008.
Adams, A.C., et al., "Characterization of Plasma-Deposited Silicon Dioxide," Journal of the Electrochemical Society 128(7):1545-1551, Jul. 1981.
Adkins, J.N., et al., "Toward a Human Blood Serum Proteome," Molecular & Cellular Proteomics 1(12):947-955, Dec. 2002.
Archakov, A.I., and Y.D. Ivanov, "Analytical Nanobiotechnology for Medicine Diagnostics," Molecular BioSystems 3(5):336-342, May 2007.

Armani, A.M., et al., "Label-Free, Single-Molecule Detection With Optical Microcavities," Science 317(5839):783-787, Aug. 2007.
Azzaroni, O., et al., "UCST Wetting Transitions of Polyzwitterionic Brushes Driven by Self-Association," Angewandte Chemie International Edition 45(11):1770-1774, Mar. 2006.
Bearinger, J.P., et al., "Chemisorbed Poly(propylene sulphide)-Based Copolymers Resist Biomolecular Interactions," Nature Materials 2(4):259-264, Apr. 2003.
Benson, J.D., et al., "Validating Cancer Drug Targets," Nature 441(7092):451-456, May 2006.
Bernards, M.T., et al., "Nonfouling Polymer Brushes via Surface-Initiated, Two-Component Atom Transfer Radical Polymerization," Macromolecules 41(12):4216-4219, May 2008.
Bousse, L., et al., "Zeta Potential Measurements of $TA_2O_5$ and $SiO_2$ Thin Films," Journal of Colloid and Interface Science 147(1):22-32, Nov. 1991.
Brault, N.D., et al., "Ultra-Low Fouling and Functionalizable Zwitterionic Coatings Grafted Onto $SiO_2$ via a Biomimetic Adhesive Group for Sensing and Detection in Complex Media," Biosensors and Bioelectronics 25(10):2276-2282, Jun. 2010.
Burg, T.P., et al., "Weighing of Biomolecules, Single Cells and Single Nanoparticles in Fluid," Nature 446(7139):1066-1069, Apr. 2007.
Campbell, C.T., and G. Kim, "SPR Microscopy and Its Applications to High-Throughput Analyses of Biomolecular Binding Events and Their Kinetics," Biomaterials 28(15):2380-2392, May 2007.
Cao, L., et al., "Plasma-Deposited Tetraglyme Surfaces Greatly Reduce Total Blood Protein Adsorption, Contact Activation, Platelet Adhesion, Platelet Procoagulant Activity, and In Vitro Thrombus Deposition," Journal of Biomedical Materials Research Part A 81(4):827-837, Jun. 2007.
Ceiler, M.F., et al., "Plasma—Enhanced Chemical Vapor Deposition of Silicon Dioxide Deposited at Low Temperatures," Journal of the Electrochemical Society 142(6):2067-2071, Jun. 1995.
Chang, Y., et al., "Highly Protein-Resistant Coatings From Well-Defined Diblock Copolymers Containing Sulfobetaines," Langmuir 22(5):2222-2226, Feb. 2006.
Chang, Y.,, et al., "Development of Biocompatible Interpenetrating Polymer Networks Containing a Sulfobetaine-Based Polymer and a Segmented Polyurethane for Protein Resistance," Biomacromolecules 8(1):122-127, Jan. 2007.
Chapman, R.G., et al., "Polymeric Thin Films That Resist the Adsorption of Proteins and the Adhesion of Bacteria," Langmuir 17(4):1225-1233, Feb. 2001.
Chelmowski, R., et al., "Peptide-Based SAMs That Resist the Adsorption of Proteins," Journal of the American Chemical Society 130(45):14952-14953, Nov. 2008.
Chen, G.Y., et al., "Adsorption-Induced Surface Stress and Its Effects on Resonance Frequency of Microcantilevers," Journal of Applied Physics 77(8):3618-3622, Apr. 1995.
Chen, J., et al., "Nanotechnology and Biosensors," Biotechnology Advances 22(7):505-518, Sep. 2004.
Chen, R.X., et al., "Surface-Initiated Atom Transfer Radical Polymerization Grafting of Poly(2,2,2-trifluoroethyl methacrylate) From Flat Silicon Wafer Surfaces," Journal of Polymer Science Part A: Polymer Chemistry 44(3):1252-1262, Feb. 2006.
Chen, S.F., and S.Y. Jiang, "A New Avenue to Nonfouling Materials," Advanced Materials 20(2):335-338, Jan. 2008.
Cheng, G., et al. "Inhibition of Bacterial Adhesion and Biofilm Formation on Zwitterionic Surfaces," Biomaterials 28(29):4192-4199, Oct. 2007.
Cheng, G., et al., "Switchable Biocompatible Polymer Surface With Self-Sterilizing and Non-Fouling/Biocompatible Capabilities," Angewandte Chemie International Edition 47(46):8831-8834, Nov. 2008.
Cheng, G., et al., "Zwitterionic Carboxybetaine Polymer Surfaces and Their Resistance to Long-Term Biofilm Formation," Biomaterials 30(28):5234-5240, Oct. 2009.
Cheng, M.M.-C., et al., "Nanotechnologies for Biomolecular Detection and Medical Diagnostics," Current Opinion in Chemical Biology 10(1):11-19, Feb. 2006.
Corot, C., et al., "Recent Advances in Iron Oxide Nanocrystal Technology for Medical Imaging," Advanced Drug Delivery Reviews 58(14):1471-1504, Dec. 2006.

(56) References Cited

OTHER PUBLICATIONS

Costerton, J.W., et al., "Bacterial Biofilms in Nature and Disease," Annual Review of Microbiology 41:435-464, 1987.
Da Silva, C.M.F., et al., "Binding of Plasminogen to Pseudomonas aeruginosa Results in Formation of Surface-Associated Plasmin and Enhanced Bacterial Invasiveness," Microbial Pathogenesis 36(2):59-66, Feb. 2004.
Dalsin, J.L., et al., "Mussel Adhesive Protein Mimetic Polymers for the Preparation of Nonfouling Surfaces," Journal of the American Chemical Society 125(14):4253-4258, Apr. 2003.
Dalsin, J.L., et al., "Protein Resistance of Titanium Oxide Surfaces Modified by Biologically Inspired mPEG-DOPA," Langmuir 21(2):640-646, Jan. 2005.
Diamandis, E.P., et al., "Mass Spectrometry as a Diagnostic and a Cancer Biomarker Discovery Tool," Molecular & Cellular Proteomics 3(4):367-378, Apr. 2004.
Dobson, J., et al., "Magnetic Nanoparticles for Drug Delivery," Drug Development Research 67(1):55-60, Jun. 2007.
Duguet, E.,, et al., "Magnetic Nanoparticles and Their Applications in Medicine," Nanomedicine 1(2):157-168, Aug. 2006.
Faca, V.M., et al., "A Mouse to Human Search for Plasma Proteome Changes Associated With Pancreatic Tumor Development," PLoS Medicine 5(6):953-967, Jun. 2008.
Fan, R., et al., "Integrated Barcode Chips for Rapid, Multiplexed Anlaysis of Proteins in Microliter Quantities of Blood," Nature Biotechnology 26(12):1373-1378, Dec. 2008.
Fan, X., et al., "Biomimetic Anchor for Surface-Initiated Polymerization From Metal Substrates," Journal of the American Chemical Society 127(45):15843-15847, Nov. 2005.
Fan, X., et al., "Cell Fouling Resistance of Polymer Brushes Grafted From Ti Substrates by Surface-Initiated Polymerization: Effect of Ethylene Glycol Side Chain Length," Biomacromolecules 7(8):2443-2448, Aug. 2006.
Fang, C., and M. Zhang, "Multifunctional Magnetic Nanoparticles for Medical Imaging Applications," Journal of Materials Chemistry 19(35):6258-6266, Jan. 2009.
Fang, C., et al., "Functionalized Nanoparticles With Long-Term Stability in Biological Media," Small 5(14):1637-1641, Jul. 2009.
Feng, B., et al., "Urinary Markers in Colorectal Cancer," Advances in Clinical Chemistry 47:45-57, 2009.
Ferrari, M., "Cancer Nanotechnology: Opportunities and Challenges," Nature Reviews: Cancer 5(3):161-171, Mar. 2005.
Fischer, H., et al., "Average Protein Density Is a Molecular-Weight-Dependent Function," Protein Science 13(10):2825-2828, Oct. 2004.
Fredriksson, S., et al., "Protein Detection Using Proximity-Dependent DNA Ligation Assays," Nature Biotechnology 20(5):473-477, May 2002.
Fujii, K., et al., "Prevention of Biofilm Formation With a Coating of 2-Methacryloyloxyethyl Phosphorylcholine Polymer," Journal of Veterinary Medical Science 70(2):167-173, Feb. 2008.
Gao, C., et al., "Functionalizable and Ultra-Low Fouling Zwitterionic Surfaces via Adhesive Mussel Mimetic Linkages," Biomaterials 31(7):1486-1492, Mar. 2010.
Gebbink, M.F., et al., "Amyloids—A Functional Coat for Microorganisms," Nature Reviews: Microbiology 3(4):333-341, Apr. 2005.
Glasmästar, K., et al., "Protein Adsorption on Supported Phospholipid Bilayers," Journal of Colloid and Interface Science 246(1):40-47, Feb. 2002.
Zhang, A.F., et al., "A Covalent-Chemistry Approach to Giant Macromolecules and Their Wetting Behavior on Solid Substrates," Angewandte Chemie International Edition 43(39):5185-5188, Oct. 2004.
Zhang, L., et al., "Gum Arabic-Coated Magnetic Nanoparticles for Potential Application in Simultaneous Magnetic Targeting and Tumor Imaging," American Association of Pharmaceutical Scientists (AAPS) Journal 11(4):693-699, Dec. 2009.
Zhang, L., et al., "Imaging and Cell Targeting Characteristics of Magnetic Nanoparticles Modified by a Functionalizable Zwitterionic Polymer With Adhesive 3,4-Dihydroxyphenyl-L-alanine Linkages," Biomaterials 31(25):6582-6588, Sep. 2010.
Zhang, X., et al., "Recent Advances in Nanotechnology Applied to Biosensors," Sensors (Basel) 9(2):1033-1053, Feb. 2009.
Zhang, Z., et al., "Blood Compatibility of Surfaces With Superlow Protein Adsorption," Biomaterials 29(32):4285-4291, Nov. 2008.
Zhang, Z., et al., "Dual-Functional Biomimetic Materials: Nonfouling Poly(carboxybetaine) With Active Functional Groups for Protein Immobilization," Biomacromolecules 7(12):3311-3315, Dec. 2006.
Zheng, G., et al., "Multiplexed Electrical Detection of Cancer Markers With Nanowire Sensor Arrays," Nature Biotechnology 23(10):1294-1301, Oct. 2005.
Zhu, H., and M. Snyder, "Protein Chip Technology," Current Opinion in Chemical Biology 7(1):55-63, Feb. 2003.
Zhu, Z., et al., "An Overview of Si-Based Biosensors," Sensor Letters 3(2):71-88, Jun. 2005.
Zürcher, S., et al., "Biomimetic Surface Modifications Based on the Cyanobacterial Iron Chelator Anachelin," Journal of the American Chemical Society 128(4):1064-1065, Feb. 2006.
McCarthy, J.R. and R. Weissleder, "Multifunctional Magnetic Nanoparticles for Targeted Imaging and Therapy," Advanced Drug Delivery Reviews 60(11):1241-1251, Aug. 2008.
Prime, K.L., and G.M. Whitesides, "Adsorption of Proteins Onto Surfaces Containing End-Attached Oligo(ethylene oxide): A Model System Using Self-Assembled Monolayers," Journal of the American Chemical Society 115(23):10714-10721, Nov. 1993.
Prime, K.L., and G.M. Whitesides, "Self-Assembled Organic Monolayers: Model Systems for Studying Adsorption of Proteins at Surfaces," Science 252(5009):1164-1167, May 1991.
Qavi, A.J., et al., "Label-Free Technologies for Quantitative Multiparameter Biological Analysis," Analytical and Bioanalytical Chemistry 394(1):121-135, May 2009.
Radpour, R., et al., "New Trends in Molecular Biomarker Discovery for Breast Cancer," Genetic Testing and Molecular Biomarkers 13(5):565-571, Oct. 2009.
Rich, R.L., and D.G. Myszka, "Survey of the Year 2007 Commercial Optical Biosensor Literature," Journal of Molecular Recognition 21(6):355-400, Nov.-Dec. 2008.
Rodríguez, R., et al., "Surface Complexation at the $TiO_2$ (Anatase) Aqueous Solution Interface: Chemisorption of Catechol," Journal of Colloid and Interface Science 177(1):122-131, Jan. 1996.
Roosjen, A., et al., "Microbial Adhesion to Poly(ethylene oxide) Brushes: Influence of Polymer Chain Length and Temperature," Langmuir 20(25):10949-10955, Dec. 2004.
Ryu, D.Y., et al., "A Generalized Approach to the Modification of Solid Surfaces," Science 308(5719):236-239, Apr. 2005.
Säfsten, P., et al., "Screening Antibody-Antigen Interactions in Parallel Using Biacore A100," Analytical Biochemistry 353(2):181-190, Jun. 2006.
Sano, T., et al., "Immuno-PCR: Very Sensitive Antigen Detection by Means of Specific Antibody-DNA Conjugates," Science 258(5079):120-122, Oct. 1992.
Sato, T., et al., "Magnetic Properties of Ultrafine Ferrite Particles," Journal of Magnetism and Magnetic Materials 65(2-3):252-256, Mar. 1987.
Sawyers, C.L., "The Cancer Biomarker Problem," Nature 452(7187):548-552, Apr. 2008.
Schweitzer, B., et al., "Multiplexed Protein Profiling on Microarrays by Rolling-Circle Amplification," Nature Biotechnology 20(4):359-365, Apr. 2002.
Seo, S.-B., et al., "Novel Multifunctional PHDCA/PEI Nano-Drug Carriers for Simultaneous Magnetically Targeted Cancer Therapy and Diagnosis via Magnetic Resonance Imaging," Nanotechnology 18(47):475105, Nov. 2007, 8 pages.
Sever, M.J., and J.J. Wilker, "Synthesis of Peptides Containing DOPA (3,4-Dihydroxyphenalalanine)," Tetrahedron 57(29):6139-6146, Jul. 2001.
Shukoor, M.I., et al., "dsRNA-functionalized Multifunctional $\gamma$-$Fe_2O_3$ Nanocrystals: A Tool for Targeting Cell Surface Receptors," Angewandte Chemie International Edition 47(25):4748-4752, Jun. 2008.
Squires, T.M., et al., "Making It Stick: Convection, Reaction and Diffusion in Surface-Based Biosensors," Nature Biotechnology 26(4):417-426, Apr. 2008.

(56) References Cited

OTHER PUBLICATIONS

Statz, A., et al., "Algal Anti-Fouling and Fouling-Release Properties of Metal Surfaces Coated With a Polymer Inspired by Marine Mussels," Biofouling 22(5-6):391-399, 2006.
Statz, A.R., et al., "New Peptidomimetic Polymers for Antifouling Surfaces," Journal of the American Chemical Society 127(22):7972-7973, Jun. 2005.
Statz, A.R., et al., "Protein, Cell and Bacterial Fouling Resistance of Polypeptoid-Modified Surfaces: Effect of Side-Chain Chemistry," Soft Matter 4(1):131-139, Jan. 2008.
Stoeva, S.I., et al., "Multiplexed Detection of Protein Cancer Markers With Biobarcoded Nanoparticle Probes," Journal of the American Chemical Society 128(26):8378-8379, Jul. 2006.
Sun, C., et al., "Magnetic Nanoparticles in MR Imaging and Drug Delivery," Advanced Drug Delivery Reviews 60(11):1252-1265, Aug. 2008.
Szunerits, S., et al., "Stability of the Gold/Silica Thin Film Interface: Electrochemical and Surface Plasmon Resonance Studies," Langmuir 22(25):10716-10722, Dec. 2006.
Teichroeb, J.H., et al., "Quartz Crystal Microbalance Study of Protein Adsorption Kinetics on Poly(2-hydroxyethyl methacrylate)," Journal of Colloid and Interface Science 325(1):157-164, Sep. 2008.
Ullah, M.E, and M. Aatif, "The Footprints of Cancer Development: Cancer Biomarkers," Cancer Treatment Reviews 35(3):193-200, May 2009.
Vaisocherová, H., et al., "Comparative Study of SPR and ELISA Methods Based on Analysis of CD166/ALCAM Levels in Cancer and Control Human Sera," Biosensors and Bioelectronics 24(7):2143-2148, Mar. 2009.
Vaisocherová, H., et al., "Functionalizable Surface Platform With Reduced Nonspecific Protein Adsorption From Full Blood Plasma-Material Selection and Protein Immobilization Optimization," Biosensors and Bioelectronics 24(7):1924-1930, Mar. 2009.
Vaisocherová, H., et al., "Ultralow Fouling and Functionalizable Surface Chemistry Based on a Zwitterionic Polymer Enabling Sensitive and Specific Protein Detection in Undiluted Blood Plasma," Analytical Chemistry 80(20):7894-7901, Oct. 2008.
Varshney, M., et al., "Prion Protein Detection Using Nanomechanical Resonator Arrays and Secondary Mass Labeling," Analytical Chemistry 80(6):2141-2148, Mar. 2008.
Vignali, D.A.A., "Multiplexed Particle-Based Flow Cytometric Assays," Journal of Immunological Methods 243(1-2):243-255, Sep. 2000.
Von Muhlen, M.G., et al., "Label-Free Biomarker Sensing in Undiluted Serum With Suspended Microchannel Resonators," Analytical Chemistry 82(5):1905-1910, Mar. 2010.
Wach, J.-Y., et al., "Protein-Resistant Surfaces Through Mild Dopamine Surface Functionalization," Chemistry—A European Journal 14(34):10579-10584, Nov. 2008.
Wach.J.-Y., et al., "Antimicrobial Surfaces Through Natural Product Hybrids," Angewandte Chemie International Edition 47(37):7123-7126, Sep. 2008.

Wagner, V.E., et al., "Protein and Bacterial Fouling Characteristics of Peptide and Antibody Decorated Surfaces of PEG-poly(acrylic acid) Co-Polymers," Biomaterials 25(12):2247-2263, May 2004.
Waite, J.H., "Mussel Power," Nature Materials 7(1):8-9, Jan. 2008.
Waite, J.H., "Nature's Underwater Adhesive Specialist," International Journal of Adhesion and Adhesives 7(1):9-14, Jan. 1987.
Wang, H., et al., "Improved Method for the Preparation of Carboxylic Acid and Amine Terminated Self-Assembled Monolayers of Alkanethiolates," Langmuir 21(7):2633-2636, Mar. 2005.
Wang, L., et al., "A Biocompatible Method of Decorporation: Bisphosphonate-Modified Magnetite Nanoparticles to Remove Uranyl Ions From Blood," Journal of the American Chemical Society 128:13358-13359, Oct. 2006.
Wassaf, D., et al., "High-Throughput Affinity Ranking of Antibodies Using Surface Plasmon Resonance Microarrays," Analytical Biochemistry 351(2):241-253, Apr. 2006.
Wei, J., et al., "Stainless Steel Modified With poly(ethylene glycol) Can Prevent Protein Adsorption but Not Bacterial Adhesion," Colloids and Surfaces B 32(4):275-291, Dec. 2003.
Wielema, T.A., and J.B.F.N. Engberts, "Zwitterionic Polymers—II. Synthesis of a Novel Series of Poly(vinylbetaines) and the Effect of the Polymeric Structure on the Solubility Behaviour in Water," European Polymer Journal 26(4):415-421, 1990.
Wu, G., et al., "Bioassay of Prostate-Specific Antigen (PSA) Using Microcantilevers," Nature Biotechnology 19(9):856-860, Sep. 2001.
Wu, H., et al., "Water-Soluble Nanocrystals Through Dual-Interaction Ligands," Angewandte Chemie International Edition 47(20):3730-3734, May 2008.
Xie, J., et al., "Controlled PEGylation of Monodisperse $Fe_3O_4$ Nanoparticles for Reduced Non-Specific Uptake by Macrophate Cells," Advanced Materials 19(20):3163-3166, Oct. 2007.
Xu, C., et al., "Dopamine as a Robust Anchor to Immobilize Functional Molecules on the Iron Oxide Shell of Magnetic Nanoparticles," Journal of the American Chemical Society 126(32):9938-9939, Aug. 2004.
Yang, W., et al., "Film Thickness Dependence of Protein Adsorption From Blood Serum and Plasma Onto Poly(sulfobetaine)-Grafted Surfaces," Langmuir 24(17):9211-9214, Sep. 2008.
Yang, W., et al., "Pursuing 'Zero' Protein Adsorption of Poly(carboxybetaine) From Undiluted Blood Serum and Plasma," Langmuir 25(19):11911-11916, Oct. 2009.
Yang, Z., et al., "Long-Circulating Near-Infrared Fluorescence Core-Cross-Linked Polymeric Micelles: Synthesis, Characterization, and Dual Nuclear/Optical Imaging," Biomacromolecules 8(11):3422-3428, Nov. 2007.
Yavuz, C.T., et al., "Low-Field Magnetic Separation of Monodisperse $Fe_3O_4$ Nanocrystals," Science 314(5801):964-967, Nov. 2006.
Yue, M., et al., "Label-Free Protein Recognition Two-Dimensional Array Using Nanomechanical Sensors," Nano Letters 8(2):520-524, Feb. 2008.

\* cited by examiner

Initiator 1

Initiator 2

Ion-pair comonomer

ZWITTERIONIC POLYMERS HAVING BIOMIMETIC ADHESIVE LINKAGES

STATEMENT OF GOVERNMENT LICENSE RIGHTS

This invention was made with Government support under HDTRA1-07-1-0033 awarded by the Defense Threat Reduction Agency and N000140410409 and N000140711036 awarded by the Office of Naval Research. The Government has certain rights in the invention.

CROSS-REFERENCE TO RELATED APPLICATION

This application claims the benefit of U.S. Patent Application No. 61/245,892, filed Sep. 25, 2009, expressly incorporated herein by reference in its entirety.

BACKGROUND OF THE INVENTION

Significant progress in the development of novel nonfouling materials has been made for many applications such as biosensors, biomaterials, drug delivery systems, and marine coatings. Among these nonfouling materials are poly(ethylene glycol) (PEG) or oligo ethylene glycol (OEG), zwitterionic, glycomimetic, and peptidomimetic polymers. Recently zwitterionic poly(sulfobetaine methacrylate) (pSBMA) and poly(carboxybetaine methacrylate) (pCBMA) surfaces have been demonstrated as highly resistant to nonspecific protein adsorption with fibrinogen adsorption levels as low as <0.3 ng/cm². Further studies demonstrate that these surfaces are also highly resist nonspecific protein adsorption even from undiluted blood plasma and serum and bacterial adhesion/biofilm formation. These studies are based on surface-grafting the zwitterionic monomers from a surface via surface-initiated atom transfer radical polymerization (ATRP). While surface-initiated ATRP is an attractive method for achieving high packing densities and controllable film thicknesses, it is desirable to have a more convenient surface modification method to graft these zwitterionic polymers onto a variety of surfaces with various geometric shapes (e.g., interior of a small-diameter catheter tube) and surface chemistries.

Despite the advances in the development of low fouling polymers and polymer treated surfaces, a need exists for improved polymers that can be readily and effectively used to provide low fouling surfaces. The present invention seeks to fulfill this need and provides further related advantages.

SUMMARY OF THE INVENTION

The invention provides low fouling polymers having adhesive groups, methods for making the polymers, surfaces treated with the polymers, methods for making and using the polymer treated surfaces.

In certain aspects, the invention provides zwitterionic polymers, polymers that include hydrolyzable groups to provide zwitterionic polymers on hydrolysis, and polyampholytes, each of which includes one or more adhesive groups; methods for grafting the polymers to surfaces; and surfaces having the polymers grafted thereto. In other aspects, the invention provides surfaces having zwitterionic polymers and polyampholytes grafted therefrom and methods for grafting the polymers from surfaces. In certain embodiments, the polymers are grafted from surfaces to which a polymerization initiator has been adhered through an adhesive group.

In one aspect, the invention provides a polymer, comprising:
(a) polymer backbone;
(b) a plurality of cationic centers, each cationic center covalently coupled to the polymer backbone by a first linker;
(c) a counter ion associated with each cationic center;
(d) an anionic center covalently coupled to each cationic center by a second linker; and
(e) one or more dihydroxyphenyl groups covalently coupled to the polymer backbone.

Representative cationic centers include ammonium, imidazolium, triazolium, pyridinium, morpholinium, oxazolidinium, pyrazinium, pyridazinium, pyrimidinium, piperazinium, pyrrolidinium, and phosphonium centers.

Representative anionic centers include carboxylic acid groups ($CO_2^-$), sulfuric acid groups ($SO_4^{-2}$), sulfonic acid groups ($SO_3^-$), sulfinic acid groups ($SO_2^-$), phosphonic acid groups ($PO_4^{-2}$), and phosphinic acid groups ($PO_3^-$).

In one embodiment, the dihydroxyphenyl group is a 3,4-dihydroxyphenyl group.

In one embodiment, the polymer has the formula:

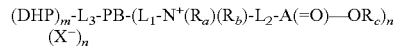

$$(DHP)_m\text{-}L_3\text{-}PB\text{-}(L_1\text{-}N^+(R_a)(R_b)\text{-}L_2\text{-}A(=O)\text{—}OR_c)_n$$
$$(X^-)_n$$

wherein PB is the polymer backbone having n pendant groups $L_1\text{-}N^+(R_a)(R_b)\text{-}L_2\text{-}A(=O)\text{—}OR_c$ and m dihydroxyphenyl groups covalently coupled to the polymer backbone through a linker moiety $L_3$; DHP is a dihydroxyphenyl group; $N^+$ is the cationic center; $R_a$ and $R_b$ are independently selected from alkyl and aryl, or taken together with the nitrogen to which they are attached form a cationic center; $A(=O)\text{—}OR_c$ is the anionic center, wherein $R_c$ is hydrogen or a counterion, and wherein A is selected from the group consisting of C, S, SO, P, or PO; $L_1$ is a linker that covalently couples the cationic center to the polymer backbone; $L_2$ is a linker that covalently couples the cationic center to the anionic center; $L_3$ is a linker moiety that covalently couples the m dihydroxyphenyl groups to the polymer backbone; $X^-$ is the counter ion associated with the cationic center; n is an integer from 1 to about 1,000; and m is from 1 to 20.

In one embodiment, $R_a$ and $R_b$ are independently selected from the group consisting of C1-C5 straight chain and branched alkyl groups. In one embodiment, $L_1$ is selected from the group consisting of —C(=O)O—$(CH_2)_n$— and —C(=O)NH—$(CH_2)_n$—, wherein n is an integer from 1 to 10. In one embodiment, $L_2$ is —$(CH_2)_n$—, where n is an integer from 1 to 5. In one embodiment, A is selected from the group consisting of C, SO, and $PO_2$. In one embodiment, $R_c$ is an ion selected from the group consisting of metal ions and ammonium ions. In one embodiment, $R_c$ is C1-C20 alkyl. In one embodiment, $X^-$ is selected from the group consisting of halide, carboxylate, alkylsulfonate, sulfate; nitrate, perchlorate, tetrafluoroborate, hexafluorophosphate, trifluoromethylsulfonate, bis(trifluoromethylsulfonyl)amide, lactate, and salicylate. In one embodiment, the polymer backbone comprises —$[CH_2\text{—}C(R_d)]_n$—, wherein $R_d$ is selected from the group consisting of hydrogen, fluorine, trifluoromethyl, and C1-C6 alkyl. In one embodiment, n is from about 10 to about 500. In one embodiment, n is from about 100 to about 300. In one embodiment, m is 1 and, in another embodiment, m is 2.

In another aspect, the invention provides a polymer, comprising:
(a) polymer backbone;
(b) a plurality of cationic centers, each cationic center covalently coupled to the polymer backbone by a first linker;
(c) a counter ion associated with each cationic center;

(d) a hydrolyzable group hydrolyzable to an anionic center covalently coupled to each cationic center by a second linker; and (e) one or more dihydroxyphenyl groups covalently coupled to the polymer backbone.

In one embodiment, the polymer has the formula:

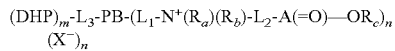

wherein PB is the polymer backbone having n pendant groups $L_1-N^+(R_a)(R_b)-L_2-A(=O)—OR_c)$ and m dihydroxyphenyl groups covalently coupled to the polymer backbone through a linker moiety $L_3$; DHP is a dihydroxyphenyl group; $N^+$ is the cationic center; $R_a$ and $R_b$ are independently selected from alkyl and aryl, or taken together with the nitrogen to which they are attached form a cationic center; $A(=O)—OR_c$ is the hydrolyzable group, wherein is an alkyl, aryl, acyl, or silyl group that may be further substituted with one or more substituents, and wherein A is selected from the group consisting of C, S, SO, P, or PO; $L_1$ is a linker that covalently couples the cationic center to the polymer backbone; $L_2$ is a linker that covalently couples the cationic center to the hydrolyzable group; $L_3$ is a linker moiety that covalently couples the m dihydroxyphenyl groups to the polymer backbone; $X^-$ is the counter ion associated with the cationic center; n is an integer from 1 to about 1,000; and m is from 1 to 20.

In a further aspect, the invention provides a polymer, comprising:

(a) a polymer backbone;

(b) plurality of positively charged repeating units;

(c) a plurality of negatively charged repeating units; and (d) one or more dihydroxyphenyl groups covalently coupled to the polymer backbone.

In one embodiment, the polymer is substantially electronically neutral.

In one embodiment, the polymer has the formula:

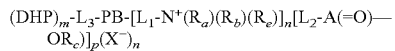

wherein PB is the polymer backbone having n pendant $L_1-N^+(R_a)(R_b)(R_e)$ groups and p pendant $L_2-A(=O)—OR_c$ groups; DHP is a dihydroxyphenyl group; $R_a$, $R_b$, and $R_e$ are independently selected from alkyl and aryl, or taken together with the nitrogen to which they are attached form a cationic center; $A(=O)—OR_c$ is an anionic center, wherein $R_c$ is hydrogen or a counterion, and wherein A is selected from the group consisting of C, S, SO, P, or PO; $L_1$ is a linker that covalently couples the cationic center to the polymer backbone; $L_2$ is a linker that covalently couples the anionic center to the polymer backbone; $L_3$ is a linker moiety that covalently couples the m dihydroxyphenyl groups to the polymer backbone; $X^-$ is the counter ion associated with the cationic center; n is an integer from 1 to about 1,000; p is an integer from 1 to about 1,000; and m is from 1 to 20.

In one embodiment, n=p.

In another aspect, the invention provides a surface of a substrate coated with a plurality of one or more polymers of the invention.

Representative substrates include particles, drug carriers, non-viral gene delivery systems, biosensors, membranes, implantable sensors, subcutaneous sensors, implants, and contact lenses. Other representative substrates include implantable medical devices, such as ear drainage tubes, feeding tubes, glaucoma drainage tubes, hydrocephalous shunts, keratoprostheses, nerve guidance tubes, urinary catheters, tissue adhesives, x-ray guides, artificial joints, artificial heart valves, artificial blood vessels, pacemakers, left ventricular assist devices (LVADs), artery grafts, tissue scaffolds, and stents.

Representative surfaces include metal surfaces, metal oxide surfaces, silicon oxide surfaces, and organic surfaces. In one embodiment, the surface is a crystalline surface.

In one embodiment, the surface further comprises a plurality of target binding partners covalently coupled to a portion of the plurality of polymers, wherein the target binding partner has affinity toward a target molecule. In one embodiment, the surface further comprises a monolayer intermediate the surface and the plurality of polymers.

In another aspect, the invention provides methods for treating a surface. In the methods, one or more of the polymers of the invention are applied to the surface. In one embodiment, applying the polymer to the surface comprises contacting a surface with a solution comprising the polymer. In one embodiment, applying the polymer to the surface comprises flowing a solution comprising the polymer over the surface. Representative surfaces include metal surfaces, metal oxide surfaces, silicon oxide surfaces, and organic surfaces. In one embodiment, the surface is a crystalline surface.

In a further aspect, the invention provides a method for making a surface having zwitterionic polymers grafted therefrom. In one embodiment, the method includes forming a radical initiator terminated monolayer on a substrate surface, wherein the radical initiator comprises one or more dihydroxyphenyl groups; and polymerizing a zwitterionic monomer on the radical initiator terminated monolayer to provide a surface having zwitterionic polymers grafted therefrom.

In another aspect, the invention provides a method for making a surface having a polyampholyte grafted therefrom. In one embodiment, the method includes forming a radical initiator terminated monolayer on a substrate surface, wherein the radical initiator comprises one or more dihydroxyphenyl groups; and polymerizing an ion-pair comonomer on the radical initiator terminated monolayer to provide a surface having polyampholytes grafted therefrom.

DESCRIPTION OF THE DRAWINGS

The patent or application file contains at least one drawing executed in color. Copies of this patent or patent application publication with color drawings will be provided by the Office upon request and payment of the necessary fee.

The foregoing aspects and many of the attendant advantages of this invention will become more readily appreciated as the same become better understood by reference to the following detailed description, when taken in conjunction with the accompanying drawings.

FIG. 11A illustrates the solvent effect on protein adsorption onto a gold surface grafted with pCB$_2$-catechol$_2$ (100% human blood plasma and serum); FIG. 11B illustrates the pH effect on protein adsorption onto a gold surface grafted with pCB$_2$-catechol$_2$; and FIG. 11C compares protein adsorption on the gold surface modified with pCB$_2$-catechol$_2$, pCB-catechol$_2$, and pCB-catechol (100% human blood plasma and serum). The data represents the mean±standard deviation (n=3).

FIG. 13A illustrates undetectable nonspecific adsorption for single protein solutions (Lyz and Fg) before antibody immobilization; FIG. 13B illustrates non-specific adsorptions from 100% human blood serum and plasma before antibody immobilization; FIG. 13C illustrates non-specific adsorption from 100% human blood plasma after anti-ALCAM immobilization.

DETAILED DESCRIPTION OF THE INVENTION

Figure 1:
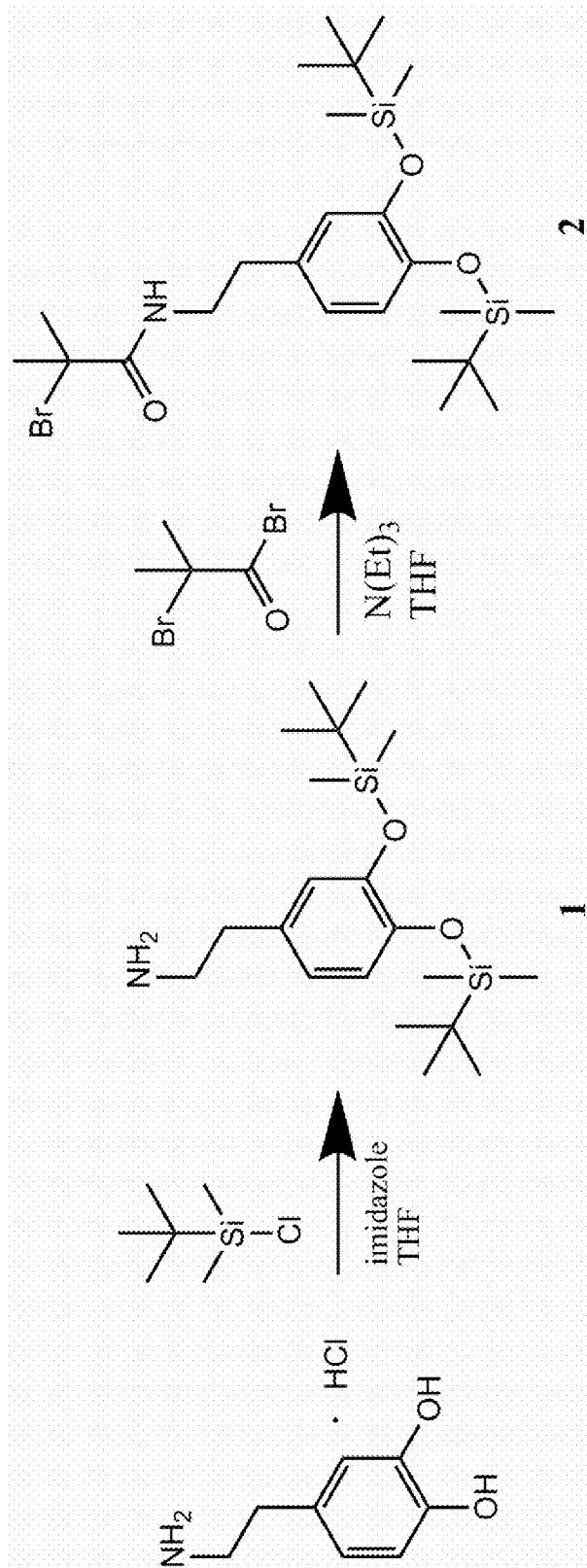
FIG. 1 is a schematic illustration of the preparation of a representative initiator useful for making polymers of the invention.

The invention provides low fouling polymers having adhesive groups, methods for making the polymers, surfaces treated with the polymers, methods for making and using the polymer treated surfaces.

In certain aspects, the invention provides zwitterionic polymers, polymers that include hydrolyzable groups to provide zwitterionic polymers on hydrolysis, and polyampholytes, each of which includes one or more adhesive groups; methods for grafting the polymers to surfaces; and surfaces having the polymers grafted thereto.

In another aspect, the invention provides surfaces having zwitterionic polymers and polyampholytes grafted therefrom and methods for grafting the polymers from surfaces. In certain embodiments, the polymers are grafted from surfaces to which a polymerization initiator has been adhered through an adhesive group.

Adhesive Zwitterionic Polymers

In one aspect, the invention provides low fouling polymers that include an adhesive group that renders the polymers useful for direct attachment to surfaces thereby imparting low fouling properties to those surfaces. In this aspect, the polymer is grafted to the surface through the interaction of the polymer's adhesive group and the surface.

In one embodiment, the polymers of the invention are zwitterionic polymers. In another embodiment, the polymers of the invention include hydrolyzable groups that are hydrolyzed to provide zwitterionic polymers. Zwitterionic polymers are polymers having a balance of positive and negative charge. Zwitterionic polymers can be highly resistant to protein adsorption and bacterial adhesion. Due to their biomimetic nature, zwitterionic polymers, such as phosphobetaine, sulfobetaine, and carboxybetaine polymers, exhibit high biocompatibility.

In one embodiment, the polymer of the invention includes (a) polymer backbone, (b) a plurality of cationic centers, each cationic center covalently coupled to the polymer backbone by a first linker, (c) a counter ion associated with each cationic center, (d) an anionic center or hydrolyzable group that is hydrolyzable to an anionic center covalently coupled to each cationic center through a second linker, and (e) one or more dihydroxyphenyl groups covalently coupled to the polymer backbone. In one embodiment, the one or more dihydroxyphenyl groups are covalently coupled to the terminus of the polymer backbone.

In certain embodiments, the polymer is a zwitterionic polymer in which the polymer includes one or more repeating units, each having a cationic center and an anionic center. In certain other embodiments, the polymer is a cationic polymer in which the polymer includes one or more repeating units, each unit having a cationic center and a hydrolyzable group that can be hydrolyzed to an anionic center, ultimately providing a zwitterionic polymer.

The cationic center can be any one of a variety of groups that include a positively charged nitrogen atom. Representative cationic centers include ammonium, imidazolium, triazolium, pyridinium, morpholinium, oxazolidinium, pyrazinium, pyridazinium, pyrimidinium, piperazinium, and pyrrolidinium groups.

Representative anionic centers include carboxylic acid groups ($CO_2^-$), sulfuric acid groups ($SO_4^{2-}$), sulfonic acid groups ($SO_3^-$), sulfinic acid groups ($SO_2^-$), phosphonic acid groups ($PO_4^{2-}$), and phosphinic acid groups ($PO_3^-$).

The polymer's one or more dihydroxyphenyl groups impart adhesive properties to the polymer. The dihydroxyphenyl group is a biomimetic adhesive group that allows the polymer to adhere to a variety of surfaces thereby immobilizing the polymers on the surface rendering the surface low fouling. In one embodiment, the dihydroxyphenyl group is a 3,4-dihydroxyphenyl group (i.e., a catechol group). In certain embodiments, the polymer of the invention includes a 3,4-dihydroxyphenyl group derived from 3,4-dihydroxyphenyl alanine (i.e., DOPA). The effectiveness of the polymers of the invention to adhere to surfaces is described in detail below.

Representative polymers of the invention have formula (I):

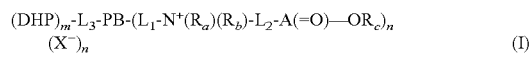

$$(DHP)_m\text{-}L_3\text{-}PB\text{-}(L_1\text{-}N^+(R_a)(R_b)\text{-}L_2\text{-}A(=O)\text{---}OR_c)_n$$
$$(X^-)_n \qquad (I)$$

wherein PB is the polymer backbone having n pendant groups $L_1\text{-}N^+(R_a)(R_b)\text{-}L_2\text{-}A(=O)\text{---}OR_c$) and m dihydroxyphenyl groups covalently coupled to the polymer backbone through a linker moiety $L_3$; DHP is a dihydroxyphenyl group; $N^+$ is the cationic center; $R_a$ and $R_b$ are independently optional as necessary to provide a cationic center and independently selected from alkyl and aryl; $A(=O)\text{---}OR_c$ is the anionic center when $R_c$ is hydrogen or a counterion or a hydrolyzable group when $R_c$ is an alkyl, aryl, acyl, or silyl group that may be further substituted with one or more substituents, wherein A is selected from the group consisting of C, S, SO, P, or PO; $L_1$ is a linker that covalently couples the cationic center to the polymer backbone; $L_2$ is a linker that covalently couples the cationic center to the anionic center or hydrolyzable group; $L_3$ is a linker moiety that covalently couples the m dihydroxyphenyl groups to the polymer backbone; $X^-$ is the counter ion associated with the cationic center; n is an integer from 1 to about 1,000; and m is an integer from 1 to 20 (for example, 1, 2, 3, or 4).

As noted above, the polymers of the invention include one or more dihydroxyphenyl groups. In one embodiment, the dihydroxyphenyl group is a 3,4-dihydroxyphenyl group (i.e., a catechol group). In certain embodiments, the polymer of the invention includes a 3,4-dihydroxyphenyl group derived from 3,4-dihydroxyphenyl alanine (i.e., DOPA). In one embodiment of formula (I), m is 1 and, in another embodiment, m is 2. In formula (I), $L_3$ is a linker moiety that covalently couples the m dihydroxyphenyl groups to the polymer backbone. The linker moiety is a group of atoms that is effective to covalently couple the m dihydroxyphenyl groups to the polymer backbone.

In formula (I), PB is the polymer backbone. Representative polymer backbones include vinyl backbones (i.e., —C(R')(R")—C(R''')(R'''')—, where R', R", R''', and R'''' are independently selected from hydrogen, alkyl, and aryl) derived from vinyl monomers (e.g., acrylate, methacrylate, acrylamide, methacrylamide, styrene). In one embodiment, the polymer backbone comprises —[$CH_2$—$C(R_d)]_n$—, wherein $R_d$ is selected from the group consisting of hydrogen, fluorine, trifluoromethyl, and C1-C6 alkyl, and n is from 1 to about 1,000.

Other suitable backbones include polymer backbones that provide for pendant cationic groups that include hydrolyzable groups that can be converted to zwitterionic groups, and backbones that include cationic groups and that provide for pendant hydrolyzable groups that can be converted to zwitterionic groups. Other representative polymer backbones include peptide (polypeptide), urethane (polyurethane), and epoxy backbones.

For the polymers of the invention, the degree of polymerization (DP or n), number average molecular weight ($M_n$), and the ratio of weight average and number average molecular weights ($M_w/M_n$), also known as polydispersity index, can vary. In one embodiment, the polymers of the invention have a degree of polymerization (n) from 1 to about 1,000. In one embodiment, n is from about 10 to about 500. In another embodiment, n is from about 100 to about 350. In one embodiment, the polymers of the invention have a number average molecular weight ($M_n$) of from about 200 to about 200,000. In one embodiment, $M_n$ is from about 2,000 to about 100,000. In another embodiment, $M_n$ is from about 20,000 to about 80,000. In one embodiment, the polymers of the invention have a ratio of weight average and number average molecular weight ($M_w/M_n$) of from about 1.0 to about 2.0. In one embodiment, $M_w/M_n$ is from about 1.1 to about 1.5. In another embodiment, $M_w/M_n$ is from about 1.2 to about 2.0.

In formula (I), $N^+$ is the cationic center. In certain embodiments, the cationic center is a quaternary ammonium (N bonded to $L_1$; $R_a$, $R_b$, and $L_2$). In addition to ammonium, other useful cationic centers include imidazolium, triazaolium, pyridinium, morpholinium, oxazolidinium, pyrazinium, pyridazinium, pyrimidinium, piperazinium, and pyrrolidinium. In these embodiments, $R_a$ and $R_b$ are absent because the four valencies of the positively-charged nitrogen are taken up by the ring structure of the cationic center and bonds to $L_1$ and $L_2$. In another embodiment, the cationic center is a phosphonium center.

When present, $R_a$ and $R_b$ are independently selected from hydrogen, alkyl, and aryl groups. Representative alkyl groups include C1-C5 straight chain and branched alkyl groups. In certain embodiments, the alkyl group is further substituted with one of more substituents including, for example, an aryl group (e.g., —$CH_2C_6H_5$, benzyl). In one embodiment, $R_a$ and $R_b$ are methyl. Representative aryl groups include C6-C12 aryl groups including, for example, phenyl.

$L_1$ is a linker that covalently couples the cationic center to the polymer backbone. In certain embodiments, $L_1$ includes a functional group (e.g., ester or amide) that couples the remainder of $L_1$ to the polymer backbone. In addition to the functional group, $L_1$ can include an C1-C10 alkylene chain. Representative $L_1$ groups include —C(=O)O—($CH_2$)$_n$— and —C(=O)NH—($CH_2$)$_n$—, where n is 1-10 (e.g., 2 or 3). In one embodiment, n is 2. In one embodiment, n is 3.

$L_2$ is a linker that covalently couples the cationic center to the anionic center or hydrolyzable group. $L_2$ can be a C1-C25 alkylene chain. Representative $L_2$ groups include —($CH_2$)$_n$—, where n is 1-5. In one embodiment, n is 2. In one embodiment, n is 3.

For those embodiments that include a hydrolyzable group, the hydrophobicity and the rate of hydrolysis of the polymers of formula (I) can be controlled by $L_1$ and/or $L_2$. The greater the hydrophobicity of $L_1$ or $L_2$, the slower the hydrolysis of the hydrolyzable group and the conversion of the cationic polymer to the zwitterionic polymer.

$L_3$ is a linker moiety that covalently couples the m dihydroxyphenyl groups to the polymer backbone. The linker moiety is a group of atoms that is effective to covalently couple the m dihydroxyphenyl groups to the polymer backbone. Suitable $L_3$ moieties include from one to about 20 atoms.

A(=O)—$OR_c$ is the anionic center or hydrolyzable group. The anionic center can be a carboxylic acid (A is C), a sulfinic acid (A is S), a sulfonic acid (A is SO), a phosphinic acid (A is P), or a phosphonic acid (A is PO). When A(=O)—$OR_c$ is an anionic center, $R_c$ is hydrogen or a counterion ion. Representative counterions include metals ions (e.g., lithium sodium, potassium, calcium, magnesium) and nitrogen-containing ions (e.g., ammonium, imidazolium, triazolium, pyridinium).

Suitable hydrolyzable groups include esters, such as a carboxylic acid ester (A is C), a sulfinic acid ester (A is S), a sulfonic acid ester (A is SO), a phosphinic acid ester (A is P), or a phosphonic acid ester (A is PO). The hydrolyzable group can also be an anhydride. When A(=O)—$OR_c$ is a hydrolyzable group, $R_c$ can be an alkyl, aryl, acyl, or silyl group that may be further substituted with one or more substituents. Representative alkyl groups include C1-C30 straight chain and branched alkyl groups. In certain embodiments, the alkyl group is further substituted with one of more substituents including, for example, an aryl group (e.g., —$CH_2C_6H_5$, benzyl). In certain embodiments, $R_c$ is a C1-C20 straight chain alkyl group. In one embodiment, $R_c$ is methyl. In another embodiment, $R_c$ is ethyl. In one embodiment, $R_c$ is a C3-C20 alkyl. In one embodiment, $R_c$ is a C4-C20 alkyl. In one embodiment, $R_c$ is a C5-C20 alkyl. In one embodiment, $R_c$ is a C6-C20 alkyl. In one embodiment, $R_c$ is a C8-C20 alkyl. In one embodiment, $R_c$ is a C10-C20 alkyl. For applications where relatively slow hydrolysis is desired, $R_c$ is a C4-C20 n-alkyl group or a C4-C30 n-alkyl group. Representative aryl groups include C6-C12 aryl groups including, for example, phenyl including substituted phenyl groups (e.g., benzoic acid). Representative acyl groups (—C(=O)$R_e$) include acyl groups where $R_e$ is C1-C20 alkyl or C6-C12 aryl. Representative silyl groups (—$SiR_3$) include silyl groups where R is C1-C20 alkyl or C6-C12 aryl.

The rate of hydrolysis of the polymers of formula (I) that include a hydrolyzable group can also be controlled by $R_c$. The slower the hydrolysis of the hydrolyzable group due to, for example, steric and/or kinetic effects due to $R_c$, the slower the conversion of the cationic polymer to the zwitterionic polymer.

In the polymers of the invention, $X^-$ is the counter ion associated with the cationic center. The counter ion can be the counter ion that results from the synthesis of the cationic polymer of formula (I) (e.g., $Cl^-$, $Br^-$, $I^-$). The counter ion that is initially produced from the synthesis of the cationic center can also be exchanged with other suitable counter ions to provide polymers having controllable hydrolysis properties and other biological properties.

The rate of hydrolysis of the cationic polymers of formula (I) can be controlled by the counter ion. The more hydrophobic the counter ion, the slower the hydrolysis of the hydrolyzable group and the slower the conversion of the cationic polymer to the zwitterionic polymer. Representative hydrophobic counter ions include halides; carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from sulfate, nitrate, perchlorate ($ClO_4$), tetrafluoroborate ($BF_4$), hexafluorophosphate ($PF_6$), trifluoromethylsulfonate ($SO_3CF_3$), bis(trifluoromethylsulfonyl)amide, lactate, salicylate, and derivatives thereof.

The formation of zwitterionic polymers from cationic polymers including hydrolyzable groups and their use is described in WO 2009/067562, expressly incorporated herein by reference in its entirety.

Figure 2:
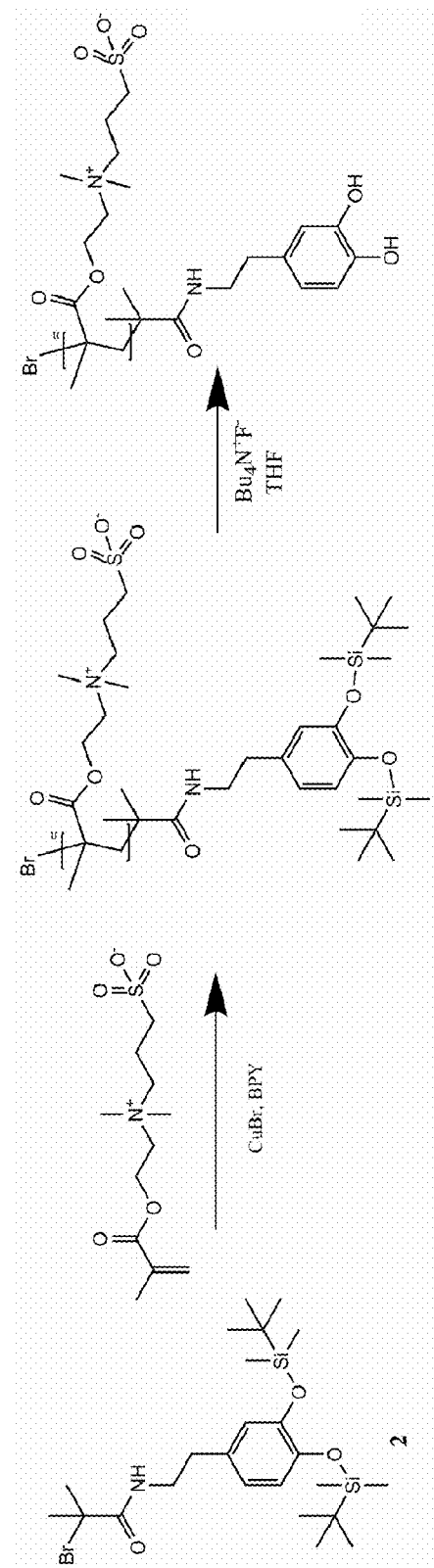
FIG. 2 is a schematic illustration of the preparation of a representation polymer of the invention.

The preparation of a representative polysulfobetaine polymer of the invention, pSB-Catechol, is described in Example 1 and illustrated in FIG. 2. The preparation of representative polycarboxybetaine polymers of the invention, pCB-Catechol polymers, are described in Example 4 and illustrated in FIGS. 9 and 10.

Adhesive Polyampholytes

In another aspect, the invention provides polyampholytes that include an adhesive group, methods for grafting the polyampholytes to surfaces, and surfaces having the polyampholytes grafted thereto and grafted therefrom. As used herein, the term "polyampholyte" refers to a copolymer having a polymer backbone, a plurality of positively charged repeating units, and a plurality of negatively charged repeating units. In the practice of the invention, these copolymers may be prepared by polymerization of an ion-pair comonomer. The polyampholytes of the invention further include one or more dihydroxyphenyl groups covalently coupled to the polymer backbone.

The polyampholytes of the invention include a plurality of positively charged repeating units, and a plurality of negatively charged repeating units. In one embodiment, the polyampholyte is substantially electronically neutral. As used herein, the term "substantially electronically neutral" refers to a copolymer that imparts advantageous nonfouling properties to a surface to which the copolymer is attached. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9.

Representative polyampholytes of the invention have formula (II):

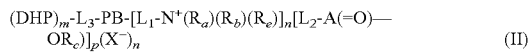  (II)

wherein

PB is the polymer backbone having n pendant $L_1-N^+(R_a)(R_b)(R_e)$ groups and p pendant $L_2-A(=O)-OR_c$ groups;

DHP is a dihydroxyphenyl group;

$R_a$, $R_b$, and $R_e$ are independently selected from alkyl and aryl, or taken together with the nitrogen to which they are attached form a cationic center;

$A(=O)-OR_c$ is an anionic center, wherein $R_c$ is hydrogen or a counterion, and wherein A is selected from the group consisting of C, S, SO, P, or PO;

$L_1$ is a linker that covalently couples the cationic center $[N^+(R_a)(R_b)(R_e)]$ to the polymer backbone;

$L_2$ is a linker that covalently couples the anionic center $[A(=O)-OR_c]$ to the polymer backbone;

$L_3$ is a linker moiety that covalently couples the m dihydroxyphenyl groups to the polymer backbone;

$X^-$ is the counter ion associated with the cationic center;

n is an integer from 1 to about 1,000;

p is an integer from 1 to about 1,000; and m is an integer from 1 to 20.

In the formula (II), $R_e$ is as described above for $R_a$ and $R_b$.

In formula (II), PB, DHP, $L_1$, $L_2$, $L_3$, $N^+$, $R_a$, $R_b$, $A(=O)OR_c$, and $X^-$ are as described above.

As noted above, in certain embodiments, the copolymers are substantially electronically neutral. In one embodiment, n is about equal to p. In one embodiment, n=p.

The polyampholytes of the invention are prepared by polymerization of ion-pair comonomers. A representative ion-pair comonomer useful in the invention has formulas (III) and (IV):

  (III)

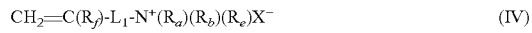  (IV)

wherein $L_1$, $L_2$, $N^+$, $R_a$, $R_b$, $R_e$, $A(=O)OR_c$, and $X^-$ are as described above, and $R_d$ and $R_f$ are independently selected from the group consisting of hydrogen, fluorine, trifluoromethyl, and C1-C6 alkyl.

Polymer Treated Surfaces and Substrates

In another aspect, the invention provides surfaces that are treated with, coated with, modified by, or otherwise incorporate one or more polymers of the invention. In certain embodiments, the invention provides a surface of a substrate that has been treated with, coated with, modified by, or otherwise incorporates one or more polymers of the invention.

In one aspect, the invention provides a surface that has been treated with a polymer of the invention. In one embodiment the surface is a surface of a substrate coated with a plurality of polymers of the invention. In certain embodiments, the surface includes a monolayer intermediate the surface and the plurality of polymers.

Representative surfaces that can be advantageously treated with the polymers of the invention include metal and metal oxide surfaces, ceramic surfaces, synthetic and natural polymeric surfaces, glass surfaces, fiber glass surface, silicon/silica surfaces, and carbon-based material surfaces. Representative natural polymeric surfaces include collagen, fibrins, and other carbohydrate surfaces suitable for the use of tissue engineering. Representative carbon-based material surfaces include carbon fiber, nanotube, and bulky ball surfaces.

Representative metals surfaces to which the polymers can be attached include gold, silver, and platinum surfaces. Representative metal oxide surfaces to which the polymers can be attached include titanium oxide and iron oxide surfaces. Representative silicon oxide surfaces to which the polymers can be attached include glass surfaces, and silica wafers. Representative organic surfaces to which the polymers can be attached include organic surfaces such as organic polymer surfaces including polyurethane, polyethylene, polystyrene, poly(methyl methacrylate) and silicone.

The polymers of the invention can be advantageously adhered to fiber surfaces. Representative fibers and fibrous materials to which the polymers can be adhered include nylon, polyvinyl nitrile, and polyester.

The polymers of the invention can also be advantageously adhered to crystalline surfaces. Representative crystalline surfaces include calcium fluoride and quartz surfaces.

The surfaces treated with the polymers of the invention can be those of substrates that benefit from such polymer treatment. Representative substrates include particles, drug carriers, non-viral gene delivery systems, biosensors, membranes, implantable sensors, subcutaneous sensors, implants, contact lenses, cables, heat exchangers, fuel and water tanks, and optical glass windows.

Suitable substrate include implantable medical devices including ear drainage tubes, feeding tubes, glaucoma drainage tubes, hydrocephalous shunts, keratoprostheses, nerve guidance tubes, urinary catheters, tissue adhesives, x-ray guides, artificial joints, artificial heart valves, artificial blood vessels, pacemakers, left ventricular assist devices (LVAD), artery grafts, tissue scaffolds, and stents.

Surfaces of diagnostic devices can be advantageously treated with the polymers of the invention. In certain embodiments, the surface further comprises a plurality of target binding partners covalently coupled to a portion of the plurality of polymers adhered to the surface. In this embodiment, the target binding partner has affinity toward a target molecule. In these embodiments, the surfaces can be used in diagnostic assays.

The binding affinity of a target molecule toward to the surface results from the target binding partners immobilized on the surface. The target binding partner and the target molecule, each termed a binding pair member, form a binding pair. Each binding pair member is a molecule that specifically binds the other member. In one embodiment, the target binding partner has affinity to a target molecule with $K_d$ less than about $10^{-8}$.

A binding pair member can be any suitable molecule including, without limitation, proteins, peptides, proteins, poly- or oligo-saccharides, glycoproteins, lipids and lipoproteins, and nucleic acids, as well as synthetic organic or inorganic molecules having a defined bioactivity, such as an antibiotic, anti-inflammatory agent, or a cell adhesion mediator.

Examples of proteins that can be immobilized on the surfaces of the present invention include ligand-binding proteins, lectins, hormones, receptors, and enzymes. Representative proteins include antibodies (monoclonal, polyclonal, chimeric, single-chain or other recombinant forms), their protein/peptide antigens, protein-peptide hormones, streptavidin, avidin, protein A, proteins G, growth factors and their respective receptors, DNA-binding proteins, cell membrane receptors, endosomal membrane receptors, nuclear membrane receptors, neuron receptors, visual receptors, and muscle cell receptors. Representative oligonucleotides that can be immobilized on the surfaces of the present invention include DNA (genomic or cDNA), RNA, antisense, ribozymes, and external guide sequences for RNAase P, and can range in size from short oligonucleotide primers up to entire genes.

Other target binding partners that bind specifically to a target compound include poly- or oligosaccharides on glycoproteins that bind to receptors, for example, the carbohydrate on the ligand for the inflammatory mediators P-selectin and E-selectin, and nucleic acid sequences that bind to complementary sequences, such as ribozymes, antisense, external guide sequences for RNAase P, and aptamers.

In one embodiment, the target binding partner is an antibody, and the target molecule is an antigen against the antibody. In this embodiment, the surface of the invention specifically binds to the antigen and resists non-specific protein adsorption. In one embodiment, the target binding partner is a protein capable of promoting cell adhesion, and the target molecule is a cell. In this embodiment, the surface of the invention specifically binds to the cell and resists non-specific protein adsorption and non-specific cell adhesion.

The use of carboxybetaine polymer surfaces for immobilizing target binding partners is described in WO 2008/083390, expressly incorporated herein by reference in its entirety.

The use of a representative polymer of the invention, $DOPA_2$-$pCBMA_2$, for coating silicon dioxide surfaces in a suspended microchannel resonator is described in von Muhlen et al., Label-Free Biomarker Sensing in Undiluted Serum with Suspended Microchannel Resonators, Anal. Chem., 2010, 82, 1905-1910, expressly incorporated herein by reference in its entirety.

The use of a representative polymer of the invention, $DOPA_2$-$pCBMA_2$, for coating silicon dioxide surfaces of surface plasmon resonance sensor chips is described in Jiang et al., Ultra-low fouling and functionalizable zwitterionic coatings grafted onto $SiO_2$ via a biomimetic adhesive group for sensing and detection in complex media, Biosensors and Bioelectronics 25 (2010) 2276-2282, expressly incorporated herein by reference in its entirety.

The use of a representative polymer of the invention, $DOPA_2$-pCBMA, for coating magnetic (iron oxide) nanoparticles is described in Jiang et al., Imaging and cell targeting characteristics of magnetic nanoparticles modified by functionalizable zwitterionic polymer with adhesive 3,4-dihydroxyphenyl-L-alanine linkages, Biomaterials 31 (2010) 6582-6588, expressly incorporated herein by reference in its entirety.

Surface coating using a representative polysulfobetaine polymer of the invention, pSB-Catechol, is described in Example 2 and the properties of the coated surface are described in Example 3. Surface coating using a representative polycarboxybetaine polymers of the invention, $pCB_2$-$Catechol_2$, is described in Example 4 and the properties of the coated surface are described in Example 6.

Figure 12:
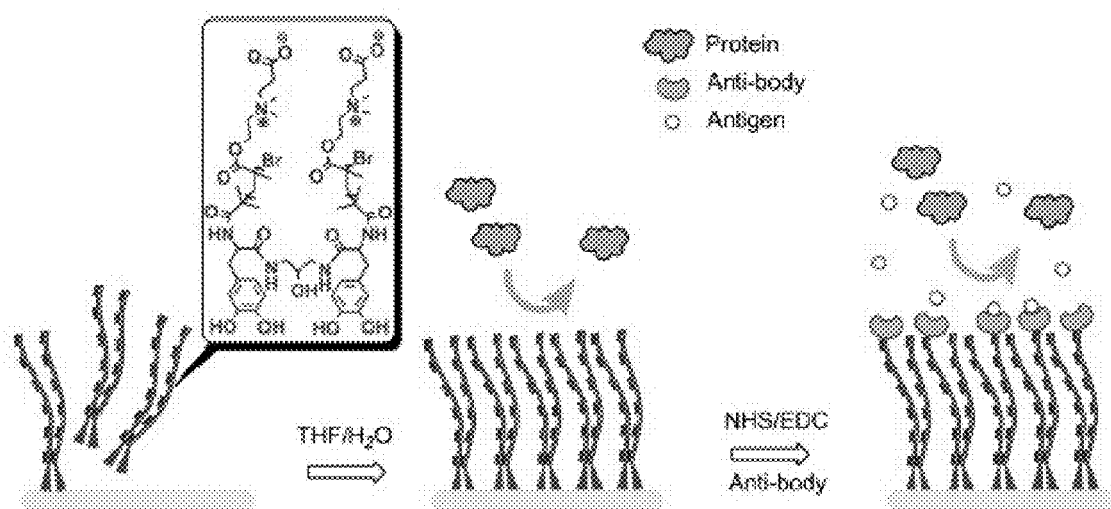
FIG. 12 is an illustration of grafting a representative polymer of the invention (pCB$_2$-catechol$_2$) to a gold surface in THF/H$_2$O, immobilizing a representative antibody (anti-ALCAM) to the pCB-modified surface, and capture of a representative antigen (ALCAM) on the antibody-bound to the pCB-modified surface.

Immobilization of a representative target binding agent (anti-ALCAM) and to a surface and the use of the surface to detect a representative target molecule (ALCAM) is described in Example 7 and illustrated in FIG. 12.

Methods for Surface Treatment

In a further aspect, methods for applying, coating, modifying, or otherwise incorporating one or more polymers of the invention onto a surface of a substrate are also provided. The polymers can be directly applied to a surface by, for example, various deposition techniques including dissolving or suspending in a solvent and then spin coating, painting or spraying. Alternatively, in other embodiments, the surfaces can be substrates onto which the polymers are made by conventional polymerization techniques involving suitable monomers.

In one aspect, the invention provides methods for treating surfaces with the polymers of the invention (i.e., polymers grafted to a surface). In the methods, a surface is treated with a polymer of the invention by applying the polymer to the surface or contacting the surface with the polymer. In one embodiment, applying the polymer to the surface comprises contacting a surface with a solution comprising the polymer. In one embodiment, applying the polymer to the surface comprises flowing a solution comprising the polymer over the surface.

Conditions for effectively adhering the polymers of the invention depend on the nature of the polymer and the surface to which the polymer is to be adhered. In certain embodiments, effective adhesion of the polymer to the surface involves presenting the polymer's adhesive group to the surface. Presenting the adhesive group to the surface can involve using a polymer solution or composition that allows the polymer to assume a conformation that reveals or exposes the adhesive group for binding to the surface (e.g., extends the polymer away from the adhesive group).

Compositions for adhering a polymer to a surface include the polymer and a solvent. Suitable solvents include aqueous solvents, organic solvents, and combinations thereof. Representative aqueous solvents include aqueous buffers such as MOPS, Tris, and PBS buffers. Representative organic solvents include acetone, acetonitrile, methanol, ethanol, isopropanol, n-propanol, dimethylformamide, dimethylsulfoxide, tetrahydrofuran, and trifluoroethanol. Representative combinations of aqueous and organic solvents include organic solvents that are miscible in water. Suitable water-miscible organic solvents include acetone, acetonitrile, methanol, ethanol, isopropanol, n-propanol, dimethylformamide, dimethylsulfoxide, tetrahydrofuran, and trifluoroethanol. Suitable compositions include water and water-miscible solvents combined in a ratio of from about 1:20 v/v to about 20:1 v/v. In one embodiment, the surface is contacted with a polymer in a MOPS buffer. In one embodiment, the surface is contacted with a polymer in a Tris buffer. In one embodiment, the surface is contacted with a polymer in aqueous tetrahydrofuran (e.g., THF:water, 1:2).

The pH of the polymer composition can affect the effectiveness of polymer adhesion to a surface. For carboxybetaine polymers, the pH is from about 2 to about 10. For sulfobetaine polymers, the pH is from about 1 to about 12.

The grafting of representative zwitterionic polymers of the invention to surfaces is described in Examples 2 and 5 and illustrated in FIG. 12.

In another aspect, the invention provides surfaces having zwitterionic polymers grafted therefrom and methods for grafting the polymers from surfaces (i.e., polymers grafted from a surface). In certain embodiments, the zwitterionic polymers are grafted from surfaces to which a polymerization initiator has been adhered through an adhesive group.

In one embodiment, the invention provides a method for making a surface having zwitterionic polymers grafted therefrom. In the method, a radical initiator terminated monolayer is formed on a substrate surface. The radical initiator comprises one or more dihydroxyphenyl groups effective to adhere the initiator to the surface. A zwitterionic monomer is then polymerized on the radical initiator terminated monolayer to provide a surface having zwitterionic polymers grafted therefrom.

In one embodiment, zwitterionic polymers are grafted from self-assembly monolayers (SAMs) terminated with initiators through atom transfer radical polymerization (ATRP) by polymerization of suitable zwitterionic monomers. In the process, the substrate surface is coated with the SAMs terminated with radical initiator followed by zwitterionic monomer polymerization onto the SAMs to form a zwitterionic polymer coating on the substrate surface. The atom transfer radical polymerization is initiated by the radical initiator at the terminus of the SAMs.

The radical terminated SAMs can be formed by a one-step or a two-step method. In a one-step method, an initiator SAM is formed by attaching radical initiator-terminated molecules to the surface through interaction with the radical initiator's dihydroxyphenyl group. In a two-step method, a functional group-terminated SAM is formed by attaching functional group-terminated molecule to the surface through covalent or noncovalent bonding. The functional group-terminated SAM is subsequently converted to the initiator-terminated SAM by chemical reaction.

Suitable polymerization methods include atom transfer radical polymerization (ATRP), reversible addition fragmentation chain transfer (RAFT) polymerization, and free radical polymerization. Any conventional radical initiators for polymerization may be used to practice the invention. The representative initiators for normal thermal or photochemical free radical polymerization include benzoyl peroxide, 2,2'-azobis(2-methylproionitrile) and benzoin methyl ether. Representative initiators for ATRP include alkyl halides, such as bromoisobutyryl bromide (BIBB). Representative initiators for RAFT polymerization (i.e., free radical initiators with chain reversible agency (CTA)) include thiocarbonylthio compounds.

As noted above, in the grafted from method, the radical initiator terminated monolayer formed on a substrate surface comprises a radical initiator that includes one or more dihydroxyphenyl groups effective to adhere the initiator to the surface.

In one embodiment, representative radical initiators of the invention have formula (V):

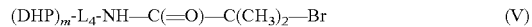

$(DHP)_m\text{-}L_4\text{-}NH\text{—}C(=O)\text{—}C(CH_3)_2\text{—}Br$ (V)

wherein $L_4$ is a linker moiety that covalently couples the m dihydroxyphenyl (DHP) groups to the amide nitrogen. Linker moiety $L_4$ can include up to about 20 atoms.

In the grafted from method, a zwitterionic monomer is polymerized on the radical initiator terminated monolayer to provide a surface having zwitterionic polymers grafted therefrom.

In one embodiment, zwitterionic monomers useful in the invention have formula (VI):

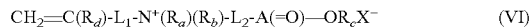

$CH_2=C(R_d)\text{-}L_1\text{-}N^+(R_a)(R_b)\text{-}L_2\text{-}A(=O)\text{—}OR_cX^-$ (VI)

wherein $L_1$, $N^+$, $R_a$, $R_b$, $A(=O)OR_c$, and $L_2$, and $X^-$ are as described above for the zwitterionic polymers, and $R_d$ is selected from the group consisting of hydrogen, fluorine, trifluoromethyl, and C1-C6 alkyl.

The preparations of representative initiators are described in Examples 1, 4, and 8 and illustrated in FIGS. 1 (showing di-TBDMS protected initiator 2), 9 (showing tetra-TBDMS protected initiator 5), and 10 (showing tetra-TBDMS protected initiator 7). The polymerization of a representative zwitterionic monomer to the radical initiator-treated surface is described in Example 8 and illustrated in FIG. 14. The properties of the surface prepared by grafting a representative zwitterionic polymer from the surface are described in Example 8.

Methods for making carboxybetaine and sulfobetaine polymers and their uses described in WO 2007/024393, expressly incorporated herein by reference in its entirety.

The following provides a description of specific polymers of the invention, methods for making the polymers, surfaces treated with the polymers, methods treating surfaces using the polymers, and characteristics of the polymer treated surfaces.

In one embodiment, the invention provides a zwitterionic sulfobetaine polymer having an adhesive moiety (e.g., catechol moiety) effective for immobilizing the polymer to a surface thereby imparting low fouling properties to the polymer-modified surface.

Figure 3:
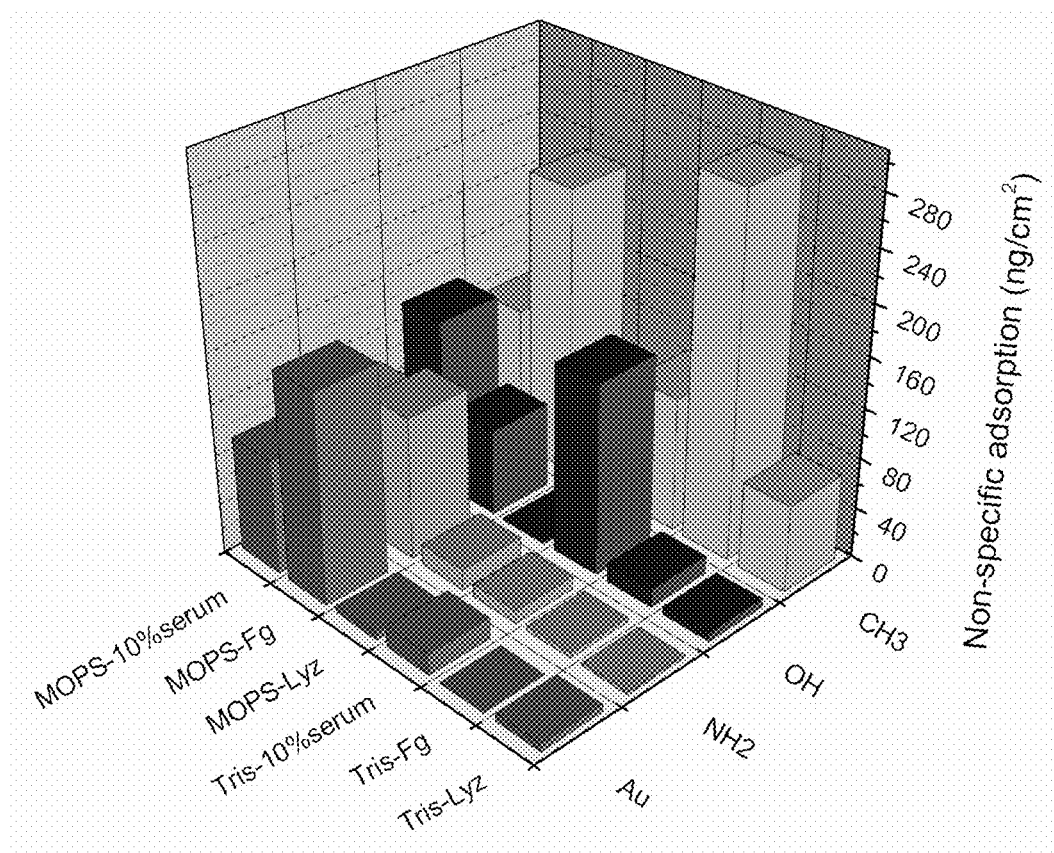
FIG. 3 compares non-specific protein adsorption (ng/cm$^2$) to various surfaces [bare gold (Au), and amino-(NH$_2$), hydroxy-(OH), and methyl-(CH$_3$) terminated self assembled monolayers] coated with pSBMA15-catechol from MOPS (pH 6.0) or Tris-HCl (pH 8.5) buffers. The non-specific protein adsorption was measured by surface plasmon resonance (SPR) for 1.0 mg/mL solutions of fibrinogen (Fg) and lysozyme (Lyz) in PBS (0.15 M, pH 7.4), and 10% serum in PBS (0.15 M, pH 7.4) (flowed over the surface at a flow rate of 0.05 mL/min for 15 min).

A catechol initiator for grafting zwitterionic polymers as shown in FIG. 1. The tert-butyldimethylsilyl (TBDMS) protecting group is acid-labile and was attached to catechol to protect the catechol oxygens. This protection is necessary for two reasons. First, the protection prevents the side reaction of the catechol oxygens with BIBB in the preparation of the initiator during Step 2 of FIG. 1. Second, the unprotected catechol oxygens are active and may lose their adhesive functionality by engaging in side reactions during storage. With the TBDMS protection, the adhesive polymer can be kept stable for a long periods. ATRP was then carried out using the catechol initiator and SBMA monomers to obtain pSBMA-catechol as shown in FIG. 2. TBAF, a mild deprotecting reagent, was then used to remove the TBDMS groups before anchoring the pSBMA-catechol onto a surface.

pSBMA-catechol is a very convenient molecule for surface modification by simply flowing the polymer over a surface. Surface packing densities of pSBMA have been established as being important for achieving ultra-low fouling in complex media such as undiluted blood. pSBMA-catechol was tested on bare gold and $NH_2$—, OH—, and $CH_3$-terminated SAM surfaces under both acidic (MOPS buffer, pH 6.0) and basic (Tris-HCl, pH 8.5) conditions. Single protein solutions of fibrinogen (Fg) and lysozyme (Lyz), and 10% blood serum were used as model probe proteins to evaluate the nonfouling properties of pSBMA-catechol coated surfaces. Fibrinogen is a soft and negatively charged protein while lysozyme is a hard and positively charged protein. 10% serum is often used for clinical medical diagnostics. pSBMA15-catechol (DPs 15, $M_n$ 4764, $M_w/M_n$ 1.26) at a concentration of 5 mg/mL was first used to modify various surface chemistries in MOPS (pH 6.0) and Tris-HCl (pH 8.5) buffers for 24 h. Protein adsorption on these surfaces was measured by a SPR sensor. FIG. 3 shows the non-specific protein adsorption to pSBMA15-catechol treated surfaces that were formed under acidic and basic conditions. As seen in FIG. 3, bare gold and $NH_2$-terminated surfaces modified by pSBMA15-catechol under basic conditions show great resistance to protein adsorption. The OH-terminated surfaces formed under identical conditions showed great resistance to protein adsorption from single protein solutions, but had more adsorption from a 10% serum solution. For the hydrophilic-SAM surfaces, protein adsorption is obviously reduced when pSBMA15-catechol is attached in basic Tris-HCl buffer as compared to acidic MOPS buffer. This can be explained by the quinone-hydroquinone interconversion of catechol. The pH of the aqueous solution can affect the quinone/hydroquinone ratio of the catechol groups. The ratio of quinone/hydroquinone in Tris-HCl buffer is more suitable for the adhesion of pSBMA-catechol. The results confirm the assumption that the ratio of quinone/hydroquinone can be adjusted to tailor the catechol adhesion. Among the surfaces tested, bare gold and $NH_2$-gold surfaces treated in Tris-HCl buffer show lowest adhesion. Metal and $NH_2$-treated surfaces interact strongly with catechol groups as demonstrated by the results shown in FIG. 3. The results demonstrated that the coatings formed on these two surfaces are highly resistant to fibrinogen, lysozyme, and 10% serum adsorption (FIG. 3) indicating a uniform coating was obtained. However, when these surfaces were exposed to whole blood plasma and serum, the treated $NH_2$ SAM surfaces showed improved performance compared to the bare gold surfaces. The $NH_2$ SAM surface was prepared using the method described in Jiang S. et al., Improved method for the preparation of carboxylic acid and amine terminated self-assembled monolayers of alkanethiolates. Langmuir 2005; 21(7):2633-2636 and provided surfaces having improved properties, including surface chemical composition, roughness, and wettability as measured by X-ray photoelectron spectroscopy, atomic force microscopy, and contact angle, respectively. The interactions between catechol and $NH_2$ have been shown to be strong, requiring 2.2 nN of pull-off force for removal of single molecule. The hydrophobic $CH_3$-terminated surface had relatively high protein adsorption even after modification under both acidic and basic conditions. The amount of adsorbed fibrinogen was as high as that found previously for $HS(CH_2)_{15}CH_3$ SAM surfaces (15 nm wavelength).

Although pSBMA15-catechol modified surfaces can effectively resist protein adsorption from single protein solutions of fibrinogen and lysozyme to a level of <5 ng/cm$^2$, these surfaces are not sufficient to resist complex media, such as undiluted blood plasma/serum and bacterial adhesion.

Figure 4:
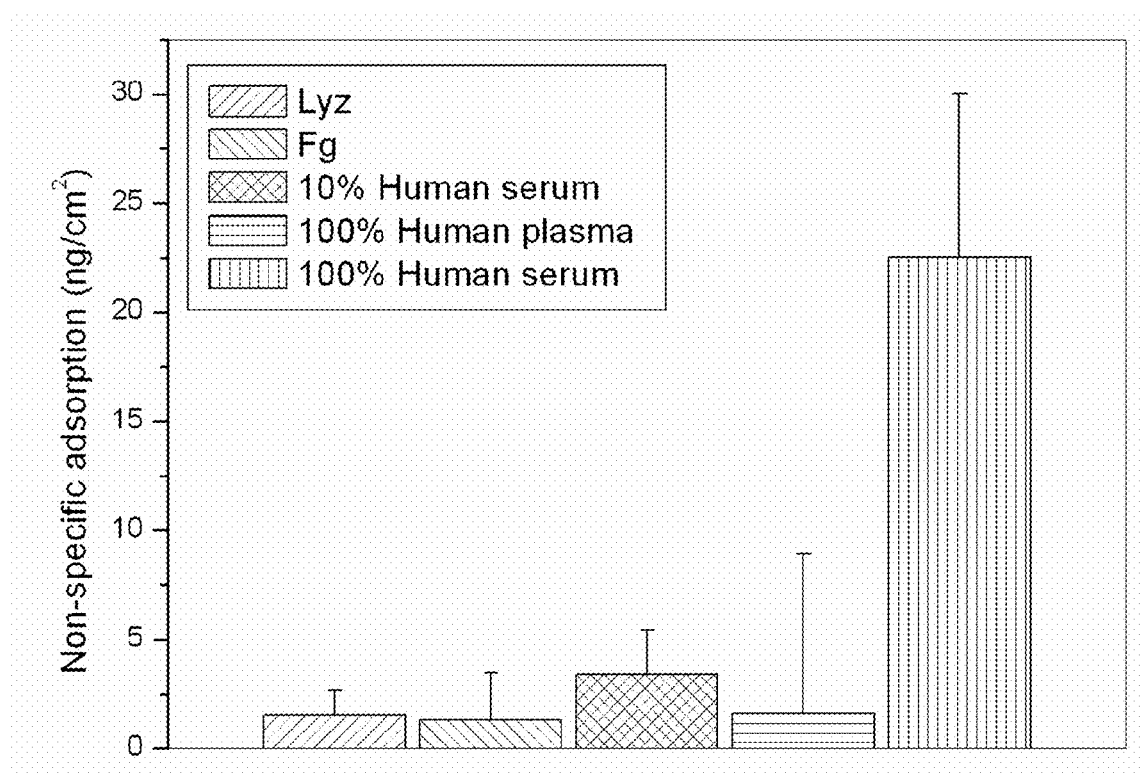
FIG. 4 compares non-specific protein adsorption (Fg, Lyz, serum, plasma) to NH$_2$ SAM surfaces coated with pSBMA300-catechol in Tris-HCl. Error bars represent standard deviations of the mean (n=5). For comparison, non-specific protein adsorption to $NH_2$ SAM surfaces coated with pSBMA15-catechol in Tris-HCl (shown in FIG. 3) is 2.1 ng/cm$^2$ of Lyz, 4.1 ng/cm$^2$ of Fg, and 10.5 ng/cm$^2$ of 10% serum (1.0 mg/mL solutions of fibrinogen (Fg) and lysozyme (Lyz) in PBS (0.15 M, pH 7.4), and 10% serum in PBS (0.15 M, pH 7.4) flowed over the surface at a flow rate of 0.05 mL/min for 15 min).
Figure 5:
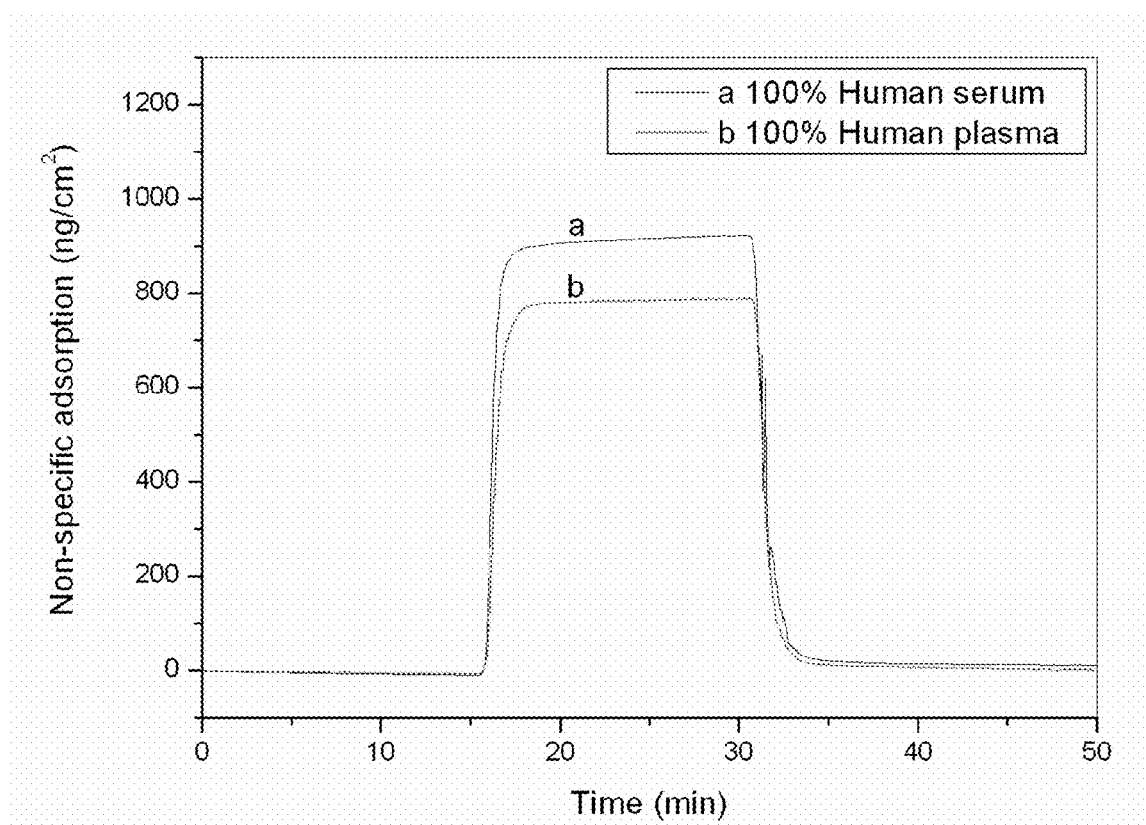
FIG. 5 compares SPR sensorgrams showing the non-specific protein adsorption to $NH_2$ SAM surfaces coated with pSBMA300-catechol in Tris-HCl upon exposure to either undiluted (100%) human plasma (a) or serum (b).

A polymer having with greater molecular weight, pSBMA300-catechol (DPs 300, $M_n$ 90340, $M_w/M_n$ 1.47) was synthesized and studied. Results are summarized in FIG. 4 (non-specific protein adsorption to the pSBMA300-catechol treated $NH_2$—Au surfaces following exposure to lysozyme (1 mg/ml), fibrinogen (1 mg/ml), 10% human serum, 100% plasma, and 100% serum). The surfaces modified with pSBMA300-catechol show less protein adsorption from lysozyme, fibrinogen, and 10% human serum as compared to the pSBMA15-catechol treated surfaces (FIG. 4). Undiluted human blood plasma and serum are among the most complex media and are far more demanding than single protein solutions or 10% serum for preventing non-specific adsorption. The pSBMA300-catechol modified surfaces were further evaluated by exposing them to 100% human plasma and serum. FIG. 5 shows representative SPR sensorgrams of pSBMA300-catechol coated $NH_2$—Au surfaces exposed to undiluted human plasma and serum indicating the nonfouling properties of this surface coating. This coating had an average protein adsorption of 1.6±7.3 ng/cm$^2$ and 22.5±7.5 ng/cm$^2$ from 100% plasma and serum, respectively, demonstrating the non-fouling properties of pSBMA300-catechol coated surfaces.

Microbial adhesion and the subsequent formation of biofilm are critical issues for many biomedical and engineering applications. Therefore, the development of surfaces that resist the initial adhesion of bacteria is the first step towards the effective prevention of long-term biofilm formation. It should be pointed out that a surface having low protein adsorption does not necessarily have high resistance to bacterial adhesion and biofilm formation. The ability to reduce protein adsorption at a surface did not correlate with the ability to reduce bacterial adhesion. Stainless steel modified with PEG resists protein adsorption, but not bacterial adhesion. The accumulation of *P. aeruginosa* after one day on pSBMA modified glass chips showed strong resistance to bacterial adhesion and biofilm formation. The 3-day accumulation of *P. aeruginosa* on the pSBMA300-catechol modified $NH_2$-glass surfaces was studied in a laminar flow chamber in situ. Bare glass was used as a reference.

Figure 6:
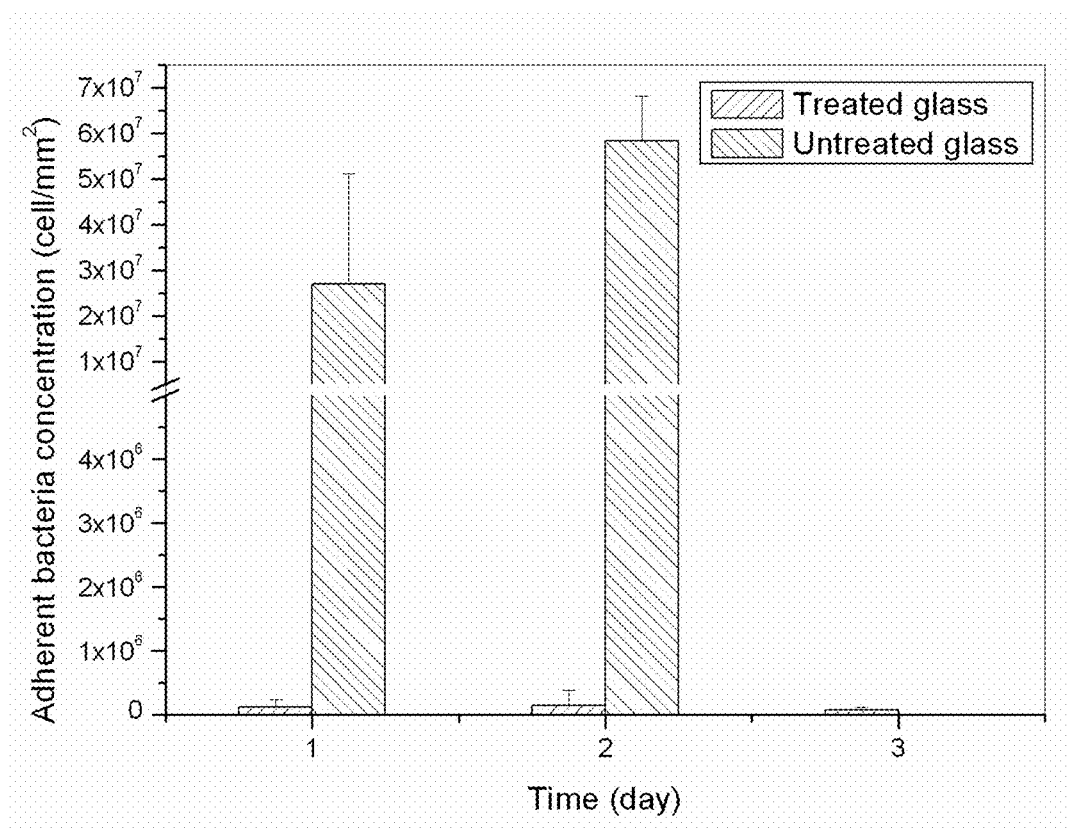
FIG. 6 compares in situ *P. aeruginosa* attachment to untreated glass and treated $NH_2$-glass surfaces coated with pSBMA300-catechol after 3 days of exposure. The data represents the mean±standard deviation (n=10). The untreated glass surface was completely covered by bacteria in 2 days (no data was collected beyond 2 days for these samples).
Figure 7A:
FIGS. 7A-7D compare fluorescence microscopy images of *P. aeruginosa* attachment to an untreated glass surface after 2 days (FIG. 7A) and to pSBMA300-catechol-coated $NH_2$-glass surface after 1 day (FIG. 7B), 2 days (FIG. 7C), and 3 days (FIG. 7D).
Figure 7B:
Figure 7C:
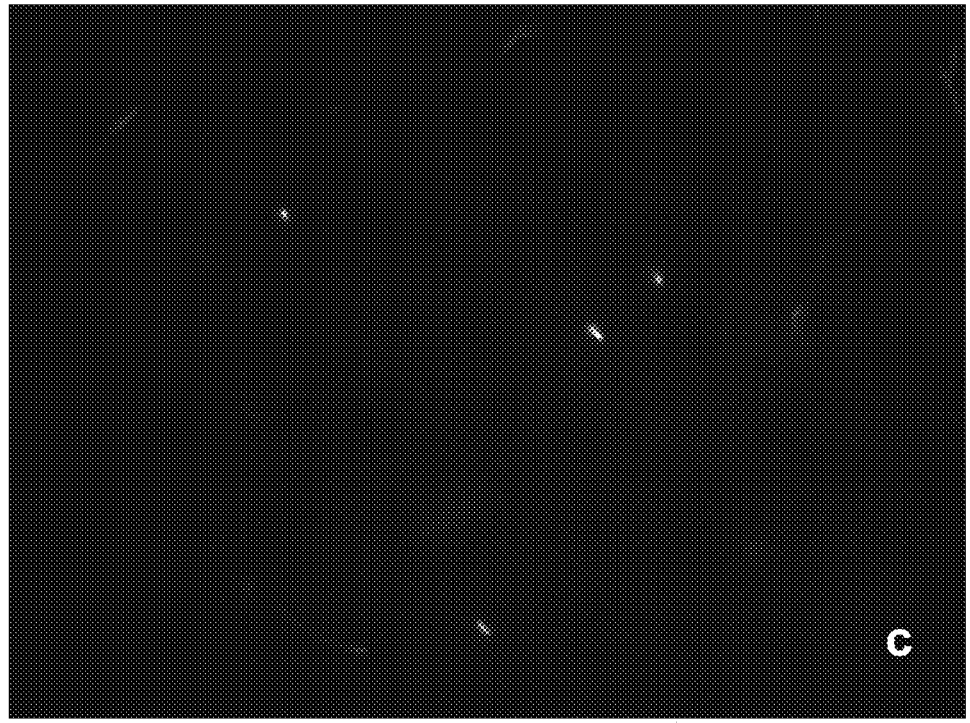
Figure 7D:
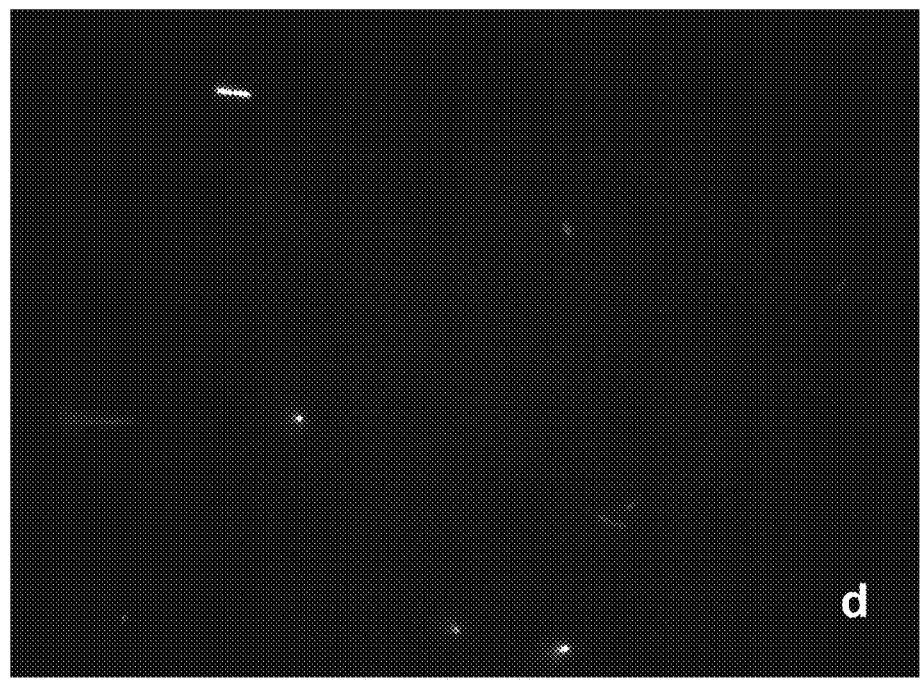

FIG. 6 compares the concentration of attached *P. aeruginosa* on the treated and untreated surfaces over a 3-day growth period. On the bare glass surface, bacterial adhesion and subsequent biofilm formation of *P. aeruginosa* were observed. A confluent biofilm was formed by the second day on the bare glass. However, the surface concentration of adherent *P. aeruginosa* on the pSBMA300-catechol treated $NH_2$ glass was substantially less (<<10$^6$ cell/mm$^2$) and did not change significantly over the 3-day period. Over the 3-day growth experiments, little bacterial adhesion was observed on the treated surfaces and no biofilm formation was observed. After 3 days, the adhesion of *P. aeruginosa* on the treated surface is reduced by 99.6% as compared to that on the bare glass surfaces tested for 2 days (p<0.05). FIG. 7 shows representative microscopy images of the accumulated *P. aeruginosa* after 3 days in the growth medium. The ability of zwitterionic pSBMA materials to inhibit protein adsorption and bacterial adhesion is believed to be due to its strong hydration via ionic solvation. The excellent properties of pSBMA to resist nonspecific protein adsorption and bacterial adhesion/biofilm formation when appropriate surface packing densities are achieved. The results demonstrate that the strong and stable anchoring of the catechol group in pSBMA-catechol can lead to well-packed pSBMA nonfouling surfaces.

Figure 8:
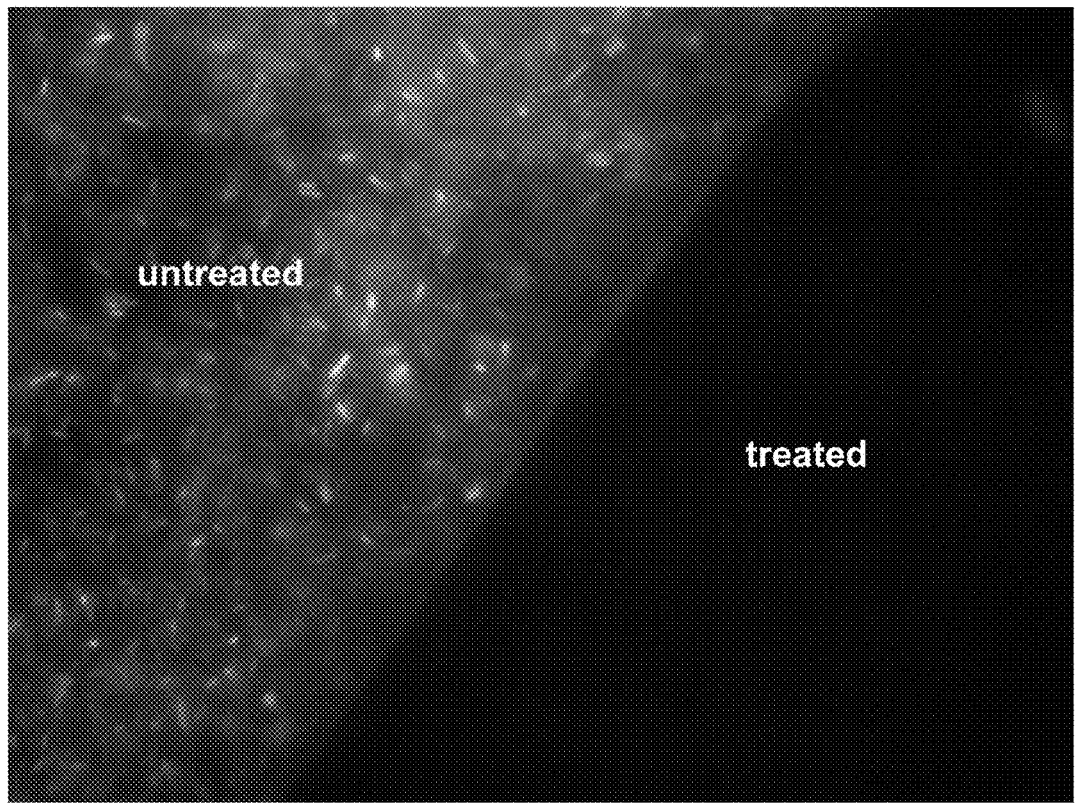
FIG. 8 is a fluorescence microscopy image showing *P. aeruginosa* attachment to a partially-coated $NH_2$-glass substrate after 70 h of bacterial adhesion. A portion of the surface was treated with pSBMA300-catechol (treated) and the remainder of the surface was unmodified (untreated).

FIG. 8 shows a fluorescence microscopy image of bacterial adhesion/biofilm formation on a $NH_2$-glass surface that was partially coated by pSBMA300-catechol. There is an absence of attached bacteria in the treated section after exposure to *P. aeruginosa* for 70 h, while *P. aeruginosa* is readily attached to the unmodified portion of the substrate. The results also show that the adhesive pSBMA-catechol polymer can be conveniently used for surface patterning protein adsorptive and resistant regions (e.g., via microcontact printing).

The present invention provides biomimetic polymers that include zwitterionic moieties for ultra-low fouling and a catechol end group for surface anchoring. Binding tests of the adhesive polymers on various surfaces, including bare gold and amino-($NH_2$), hydroxyl-(OH), and methyl-($CH_3$) terminated self-assembled monolayers (SAMs) were performed under acidic and basic conditions. Protein adsorption from single-protein solutions of fibrinogen, lysozyme, and complex media of 10-100% blood plasma and serum was measured using a surface plasmon resonance (SPR) sensor. The coated surfaces were highly resistant to nonspecific protein adsorption from both single protein solutions and blood serum/plasma. Furthermore, 3-day accumulation of *Pseudomonas aeruginosa* on the coated surfaces was evaluated in situ in a laminar flow chamber. Results show that the coated surfaces are highly resistant to bacterial adhesion and biofilm formation.

In one embodiment, the invention provides a zwitterionic carboxybetaine polymer having an adhesive moiety (e.g., catechol moiety) effective for immobilizing the polymer to a surface thereby imparting low fouling properties to the polymer-modified surface. In one embodiment, the zwitterionic carboxybetaine polymer has a single carboxybetaine polymer chain and a single adhesive moiety (e.g., pCB-catechol). In one embodiment, the zwitterionic carboxybetaine polymer has a single carboxybetaine polymer chain and two adhesive moieties (e.g., pCB-catechol$_2$). In one embodiment, the zwitterionic carboxybetaine polymer has two carboxybetaine polymer chains and two adhesive moieties (e.g., pCB$_2$-catechol$_2$).

Figure 9:
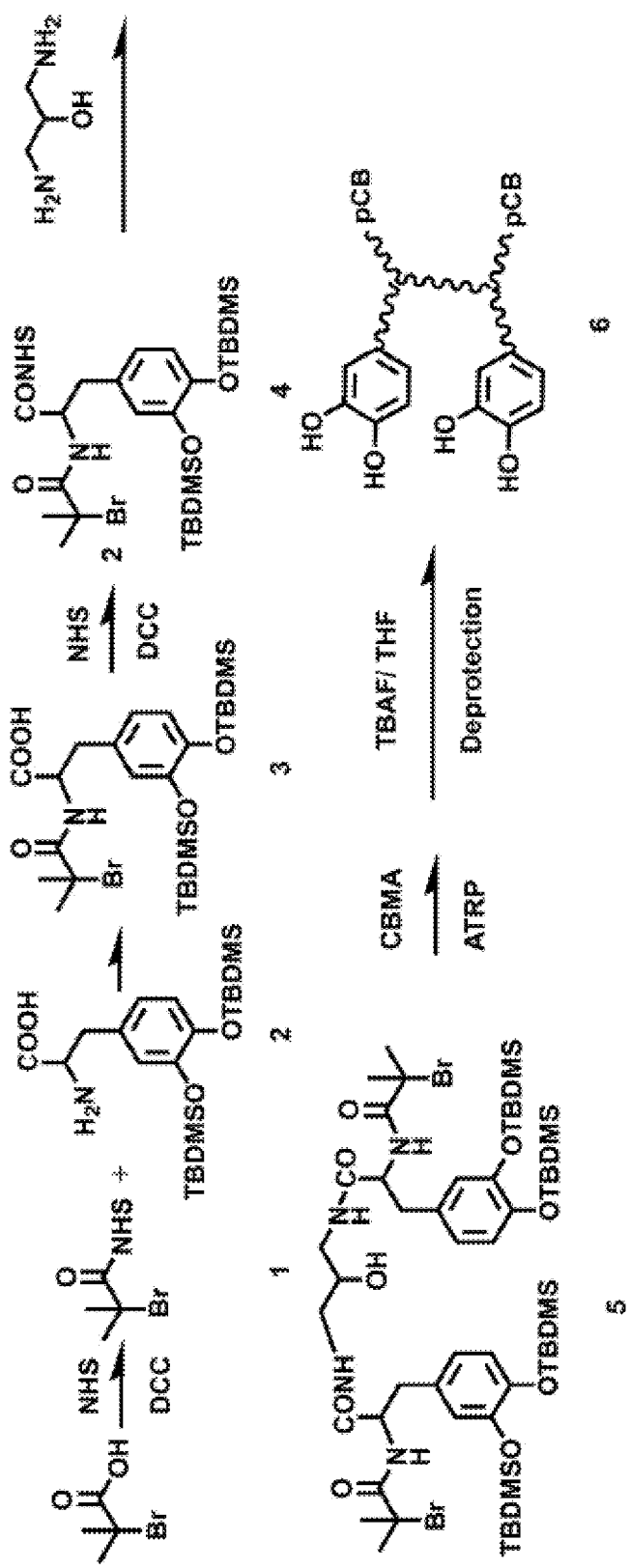
FIG. 9 is a schematic illustration of the preparation of a representative initiator (catechol$_2$-Br$_2$) useful for making polymers of the invention and a representative polymer (pCB$_2$-catechol$_2$) of the invention.
Figure 10:
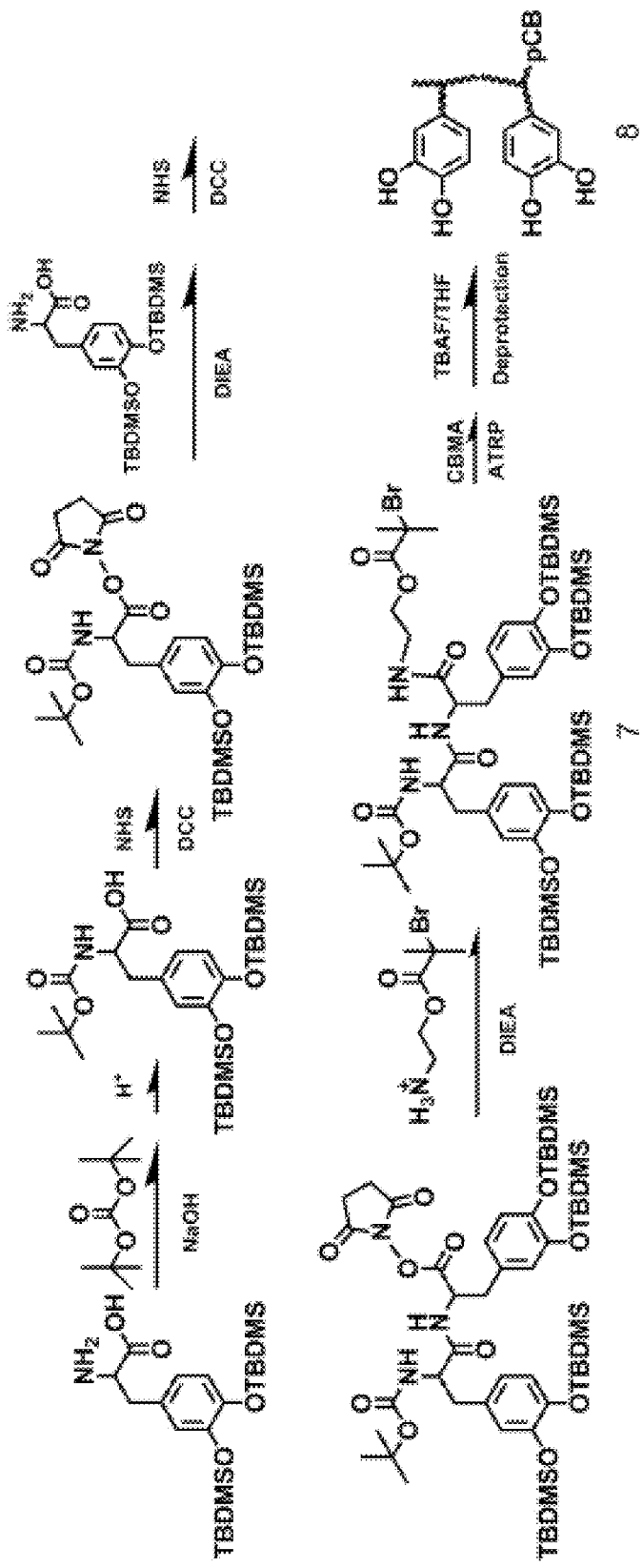
FIG. 10 is a schematic illustration of the preparation of a representative initiator (catechol$_2$-Br) useful for making polymers of the invention and a representative polymer (pCB-catechol$_2$).

The preparation of a representative initiator (catechol$_2$-Br$_2$) useful for making polymers of the invention and the preparation of a representative polymer (pCB$_2$-catechol$_2$) of the invention is illustrated in FIG. 9. FIG. 10 is a schematic illustration of the preparation of a representative initiator (catechol$_2$-Br) useful for making polymers of the invention and a representative polymer (pCB-catechol$_2$).

Initiator (5) has two protected catechol groups and two Br groups. pCB$_2$-catechol$_2$ was synthesized by ATRP of carboxybetaine monomers from the initiator. Polymers having the two adhesive catechol groups provide stronger anchoring to a surface. The uniqueness of pCB$_2$-catechol$_2$ is to demonstrate that multiple chains can grow from each initiator containing multiple catechol groups. The two pCB arms of pCB$_2$-catechol$_2$ provide greater polymer packing densities on the surface compared to pCB-catechol or pCB-catechol$_2$. The acid-labile group, t-butyldimethylsilane (TBDMS), was used to protect the active OH group in catechol molecule because catechol acts as a radical inhibitor during radical polymerization. The polymerization of CBMA with the initiator was carried out in DMF/H$_2$O (4/1, v/v) at room temperature under N$_2$. GPC data showed that the number average molecular weight (Mn) of the polymer was 83000 (narrow molecular weight polyethylene oxide used as standards) and its polydispersity was 1.20. TBDMS group in the polymer was removed by reaction with 2.5 equimolar TBAF in THF solution before the polymer was used.

Surface packing densities of a nonfouling polymer are known to be important for resisting non-specific protein adsorption, especially in complex media, such as 100% blood plasma and serum. Surfaces grafted with a functionalizable pCB polymer via surface-initiated ATRP had been shown to achieve excellent ultra-low fouling properties before and after antibody immobilization in 100% human blood serum and plasma. Unlike the "graft from" method, it is harder to control high surface packing densities via the "grafted to" method. Many studies reported the interaction mechanism of DOPA-containing polymer with TiO$_2$ surfaces. It has been shown that catechol can react with OH groups on TiO$_2$ surfaces to form a charge-transfer complex. Anchoring of pSBMA-catechol onto surfaces with NH$_2$ groups to obtain ultra-low fouling surfaces are described above. Under these conditions, formation of covalent bonds between catechol and amine groups was found. However, the interaction mechanism of adhesive catechol-containing pCB with a gold surface remains unclear.

Figure 11A:
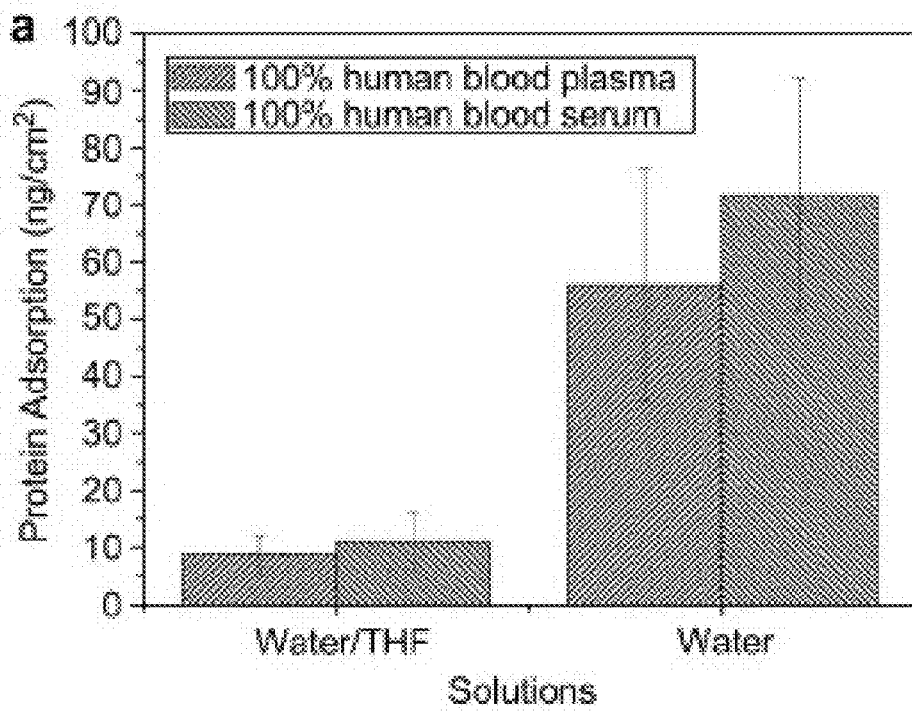
FIGS. 11A-11C compare binding to representative CB polymers of the invention.
Figure 11B:
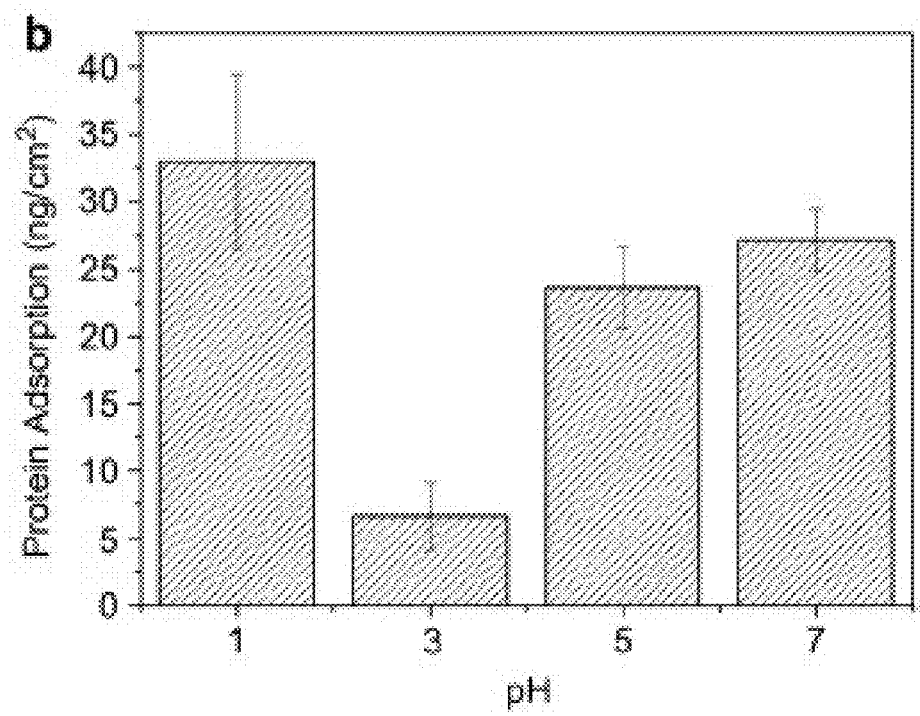
Figure 11C:
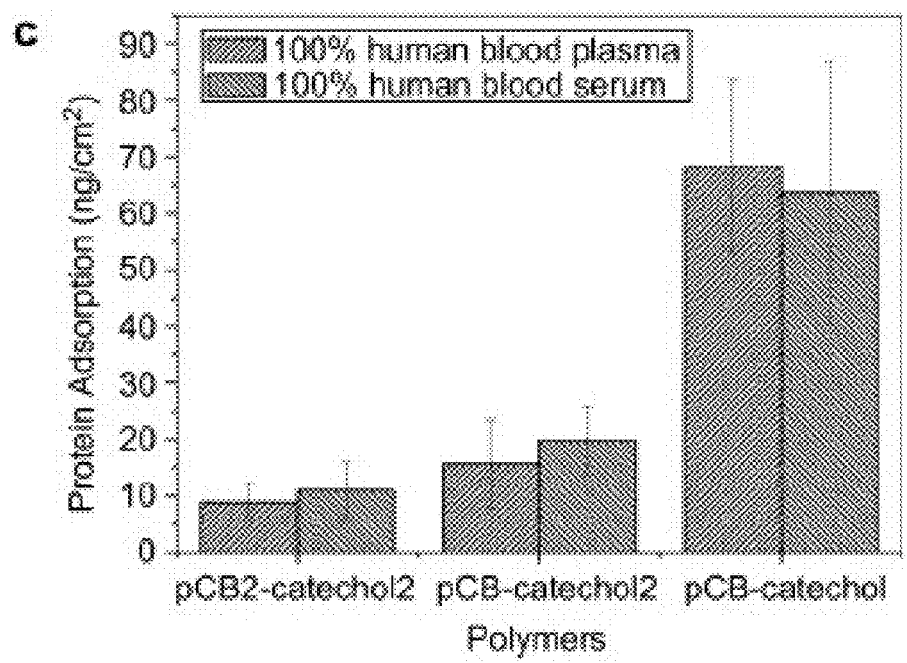

The assembly of pCB$_2$-catechol$_2$ onto a gold surface at various pH and in different solvents was evaluated. FIGS. 11A-11C compare binding to representative CB polymers of the invention.

FIG. 11A illustrates the solvent effect on protein adsorption onto a gold surface grafted with pCB$_2$-catechol$_2$ (100% human blood plasma and serum) in water and water/tetrahydrofuran (H$_2$O/THF) (2/1, v/v) solutions. The chip coated in water exhibited significant protein adsorption from 100% human blood and serum. The polymer assembled more favorably in H$_2$O/THF than in water. The film thicknesses were estimated to be 9-10 nm from H$_2$O/THF and 3-4 nm from water. Results imply that more hydrophobic catechol moieties are buried inside hydrophilic betaine brushes in water. At the same time, the presence of an organic solvent such as THF may help the exposure of hydrophobic DOPA moieties to the solvent so as to have better contact with the gold surface.

FIG. 11B illustrates the pH effect on protein adsorption onto a gold surface grafted with pCB$_2$-catechol$_2$. The pH influence on nonfouling properties of the pCB$_2$-catechol$_2$ coated gold surface in H$_2$O/THF was evaluated and results showed that the most effective nonfouling surface was obtained at about pH 3.0. The CB polymer is positively charged under acidic conditions, resulting in the extension of the polymer chains. In this way, the catechol groups will have a higher chance to be exposed to the surface. At about pH 1, although the catechol groups may be more exposed, because catechol groups do not bind strongly to the gold surface, protein adsorption is higher.

In addition to pCB$_2$-catechol$_2$, pCB-catechol with one catechol group and one pCB chain and pCB-catechol$_2$ with one pCB and two catechol groups (7) were also prepared and evaluated. The three adhesive CB polymers were compared under the optimized assembly conditions discussed above. FIG. 11C compares protein adsorption on the gold surface modified with pCB$_2$-catechol$_2$, pCB-catechol$_2$, and pCB-catechol (100% human blood plasma and serum). The lowest protein adsorption was observed for pCB$_2$-catechol$_2$, which can be explained by the strong anchoring and high surface packing of pCB$_2$-catechol$_2$ on the surface.

pCB$_2$-catechol$_2$ was grafted onto an Au surface by the simple immersion of a cleaned Au chip in the polymer solution (H$_2$O/THF=2/1, v/v, pH 3 of H$_2$O) as shown in FIG. 12. This surface had undetectable protein adsorption (<0.3 ng/cm$^2$) from single protein solutions, such as Lyz and Fg from SPR measurements. This surface had 11.0±5.0 ng/cm$^2$ and 8.9±3.4 ng/cm$^2$ in 100% human blood serum and plasma, respectively.

Figure 13A:
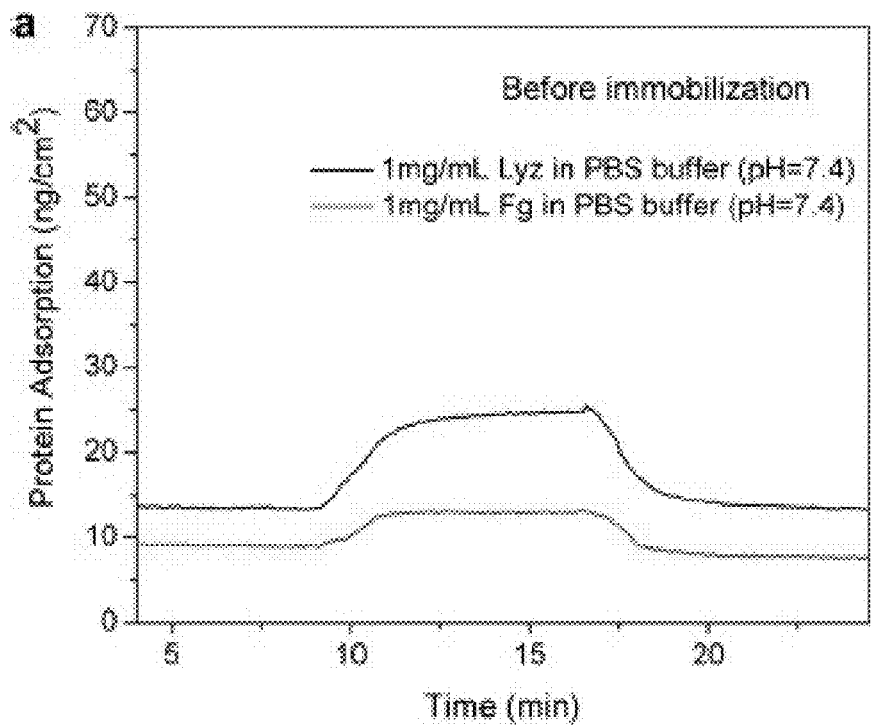
FIGS. 13A-13C are representative SPR sensorgrams of non-specific protein adsorptions before and after antibody immobilization on pCB$_2$-catechol$_2$ coated gold surfaces.
Figure 13B:
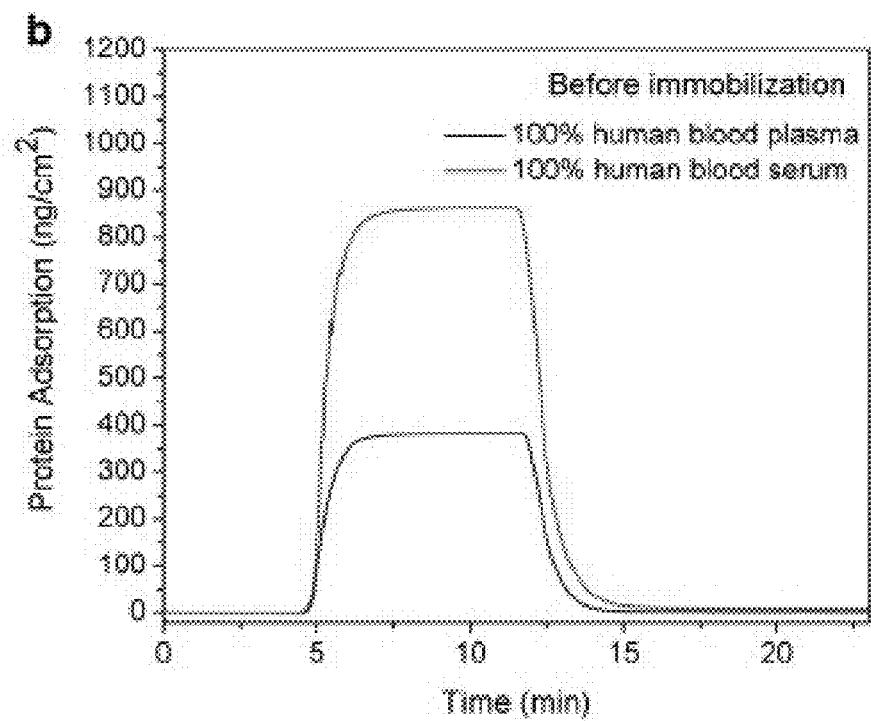
Figure 13C:
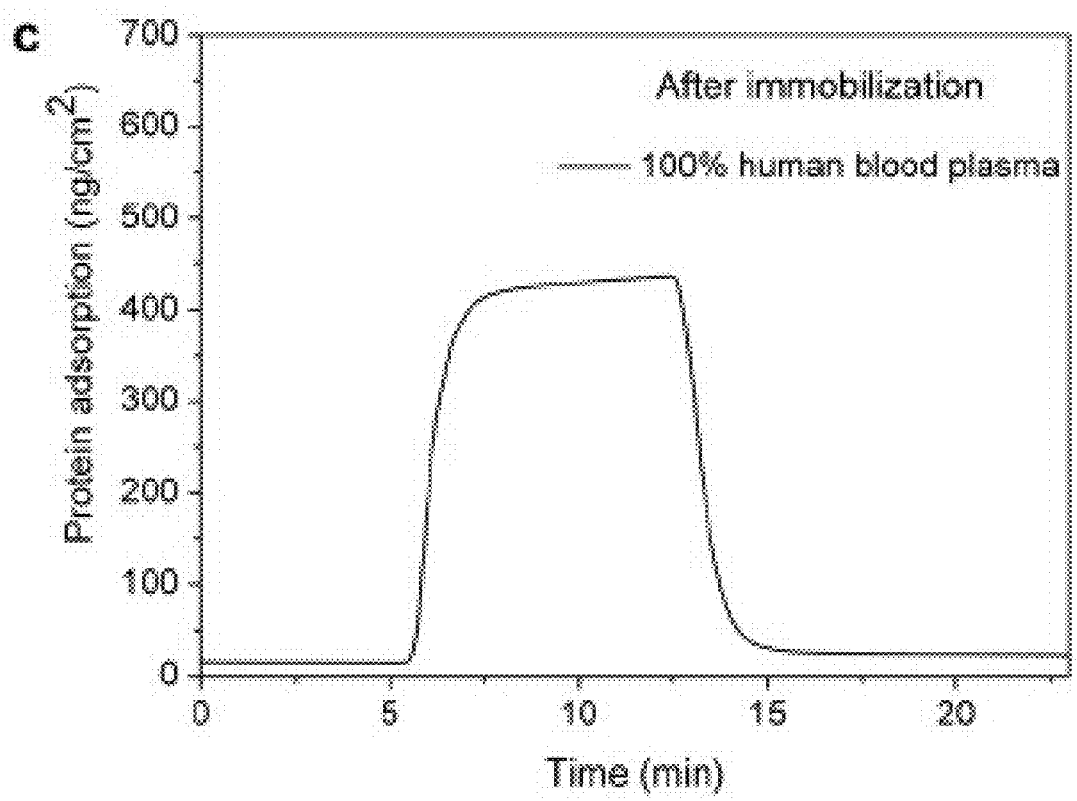

FIGS. 13A-13C are representative SPR sensorgrams of non-specific protein adsorptions before and after antibody immobilization on pCB$_2$-catechol$_2$ coated gold surfaces. FIG. 13A illustrates undetectable nonspecific adsorption for single protein solutions (Lyz and Fg) before antibody immobilization; FIG. 13B illustrates non-specific adsorptions from 100% human blood serum and plasma before antibody immobilization; FIG. 13C illustrates non-specific adsorption from 100% human blood plasma after anti-ALCAM immobilization.

pCB-modified surfaces prepared by ATRP can be immobilized with antibody without loss of nonfouling properties from undiluted blood plasma. pCB$_2$-catechol$_2$ was grafted to a gold surface and 105-135 ng/cm$^2$ anti-ALCAM was functionalized on the modified pCB surface (see FIG. 12) via an NHS/EDC conjugation. After antibody immobilization, the resulting surface had $9.5\pm4.1$ ng/cm$^2$ adsorbed proteins from 100% human blood plasma. Such low protein adsorption from 100% human blood plasma has not been achieved by other existing "graft to" coating methods. FIG. 13C shows a typical SPR sensorgram of protein adsorption onto a surface immobilized with 135 ng/cm$^2$ ALCAM from 100% blood plasma.

To investigate the bioactivity of the antibody-immobilized pCB$_2$-catechol$_2$ surface for the detection of an antigen, 100% blood plasma was spiked with recombinant ALCAM to obtain a series of samples with concentrations in a range of 30-1000 ng/mL. Each sample was flowed through the measuring channel with immobilized anti-ALCAM for 10 min, followed by 15 min of washing with PBS buffer (pH=7.4). Surfaces of pCB$_2$-catechol$_2$ were functionalized with anti-ALCAM with similar immobilized levels in the range of 105-135 ng/cm$^2$. To eliminate the effect of native ALCAM present in blood, the adsorption of plasma without extra ALCAM added on the functionalized surface was used as reference. A detection curve (not shown) was obtained for recombinant ALCAM measured in 100% blood plasma on a pCB$_2$-catechol$_2$ coated surface. The SPR results were obtained by subtracting the SPR response from the blood sample with spiked ALCAM from that without spiked ALCAM. In this way, the detected ALCAM amount reflects only that spiked since ALCAM in the native blood sample was subtracted. The detection limit (LOD) of about 30 ng/mL was determined for ALCAM detection.

In one embodiment, the invention provides functionalizable and ultra-low fouling polymers (e.g., pCB$_2$-catechol$_2$). The adhesive polymers bind strongly to surfaces via the catechol anchoring groups and provide high polymer surface packing density by the pCB2 chain(s) grown from the catechol groups. pCB$_2$-catechol$_2$ showed advantages for surface modification compared to pCB-catechol$_2$ and pCB-catechol. When compared to other adhesive polymers (e.g., DOPA-PEG, DOPA-peptidomimetic polymers, and pSB-catechol), the surfaces modified with pCB$_2$-catechol$_2$ are ready to be functionalized for further applications. Furthermore, pCB$_2$-catechol$_2$ was assembled on the Au surface other than TiO$_2$ in THF/H$_2$O at pH 3. The surface modified by pCB$_2$-catechol$_2$ are highly resistant non-specific protein adsorption (<0.3 ng/cm$^2$ for single protein adsorptions, and $11.0\pm5.0$ ng/cm$^2$ and $8.9\pm3.4$ ng/cm$^2$ in 100% human blood serum and plasma, respectively). The pCB-immobilized surface enables the direct rapid, effective, and stable immobilization of anti-ALCAM (105-135 ng/cm$_2$) onto the ultra-low fouling surface. The resulting functionalized surface maintained excellent nonfouling properties ($9.5\pm4.1$ ng/cm$^2$ for 100% human blood plasma) and excellent bioactivity for the detection of ALCAM in complex blood media. The method for immobilizing zwitterionic polymers described herein is as simple as the preparation of alkanethiolate self-assembled monolayers on noble metal surfaces, but with significant improvements in performance for applications in complex blood media. The method can be extended to surfaces other than gold.

As noted above, the invention provides surfaces having zwitterionic polymers attached thereto. In one embodiment, the zwitterionic polymers of the invention are grafted to a suitable surface by virtue of the polymers' adhesive moiety or moieties. In another embodiment, the surfaces have zwitterionic polymers grafted from the surface through the use of initiators attached to the surface by virtue of the initiators' adhesive moiety or moieties.

Figure 14:
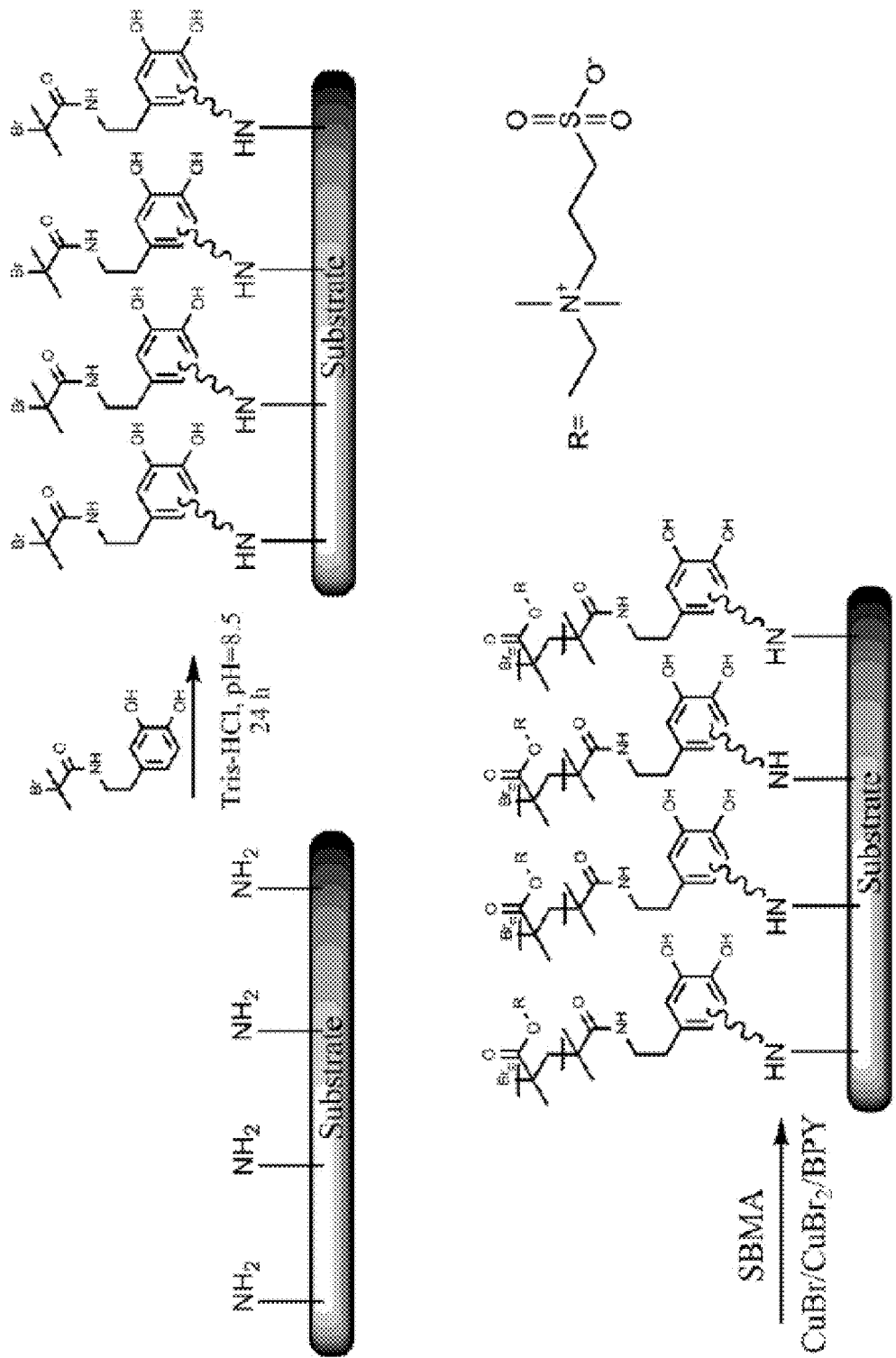
FIG. 14 is an illustration of a method of the invention for preparing a representative surface of the invention: anchoring of a catechol initiator to a surface functionalized with $NH_2$ groups and polymerization (surface-grafting) of SBMA via surface-initiated ATRP to provide a surface of the invention (pSBMA-catechol-$NH_2$-gold substrate surface).
Figure 15A:
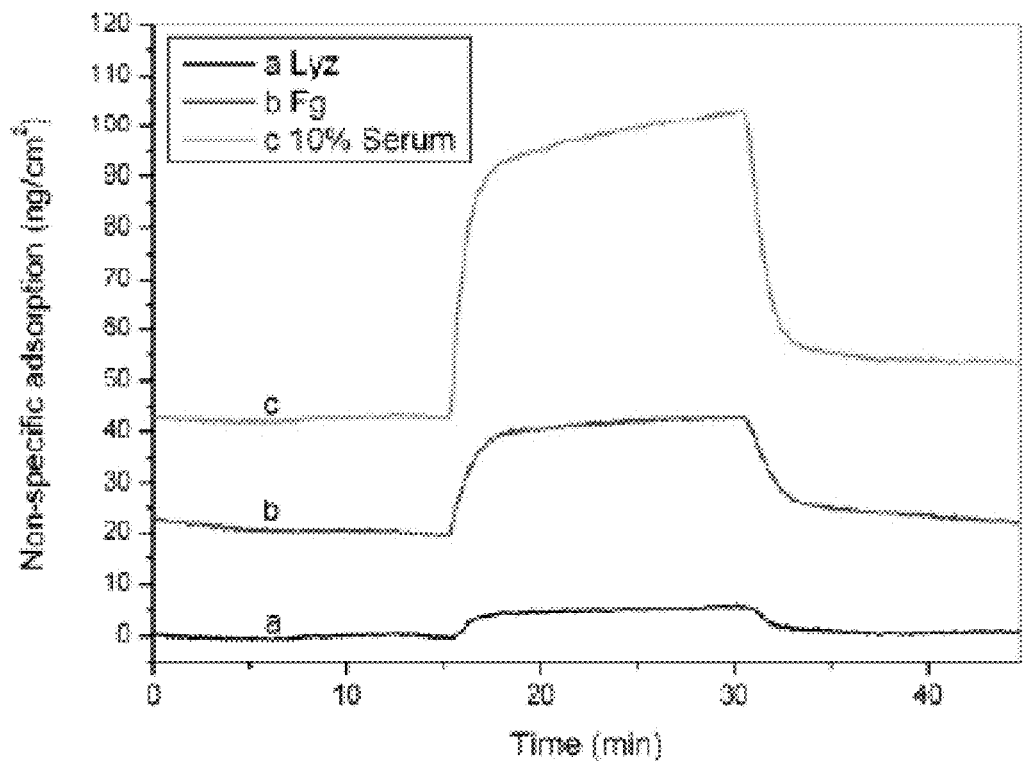
FIGS. 15A and 15B illustrate typical SPR sensorgrams showing the non-specific protein adsorption to pSBMA-catechol-gold surfaces (FIG. 15A) and pSBMA-catechol-$NH_2$-gold surfaces (FIG. 15B) from solutions of fibrinogen (1 mg/mL), lysozyme (1 mg/mL), and 10% serum in PBS (0.15 M, pH 7.4).
Figure 15B:
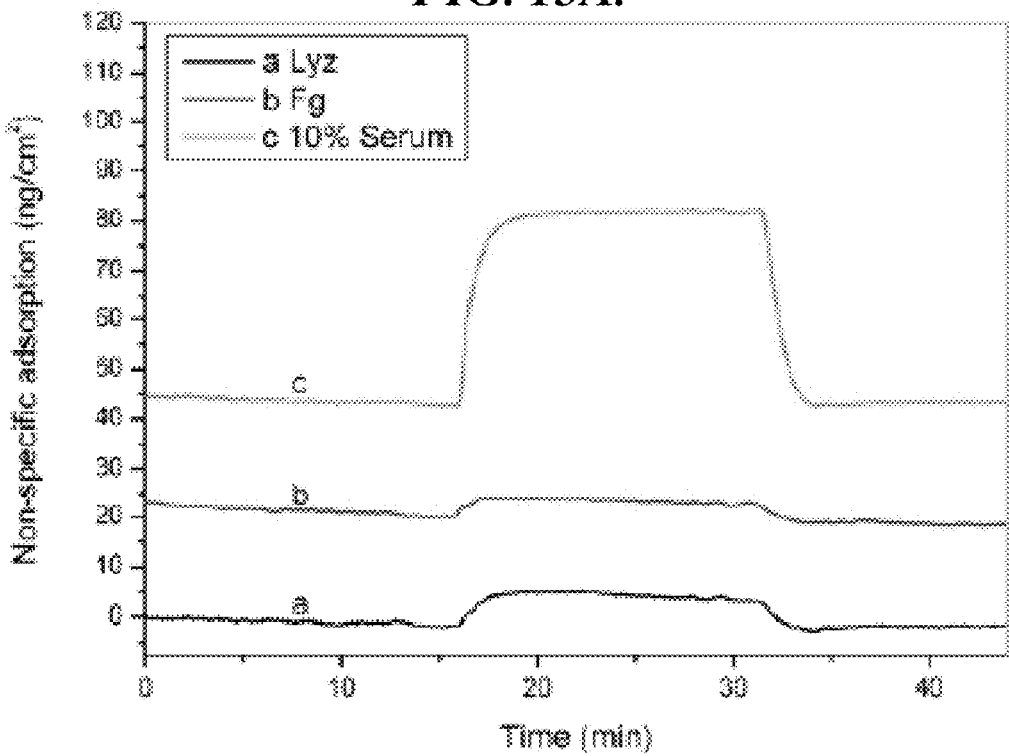
Figure 16:
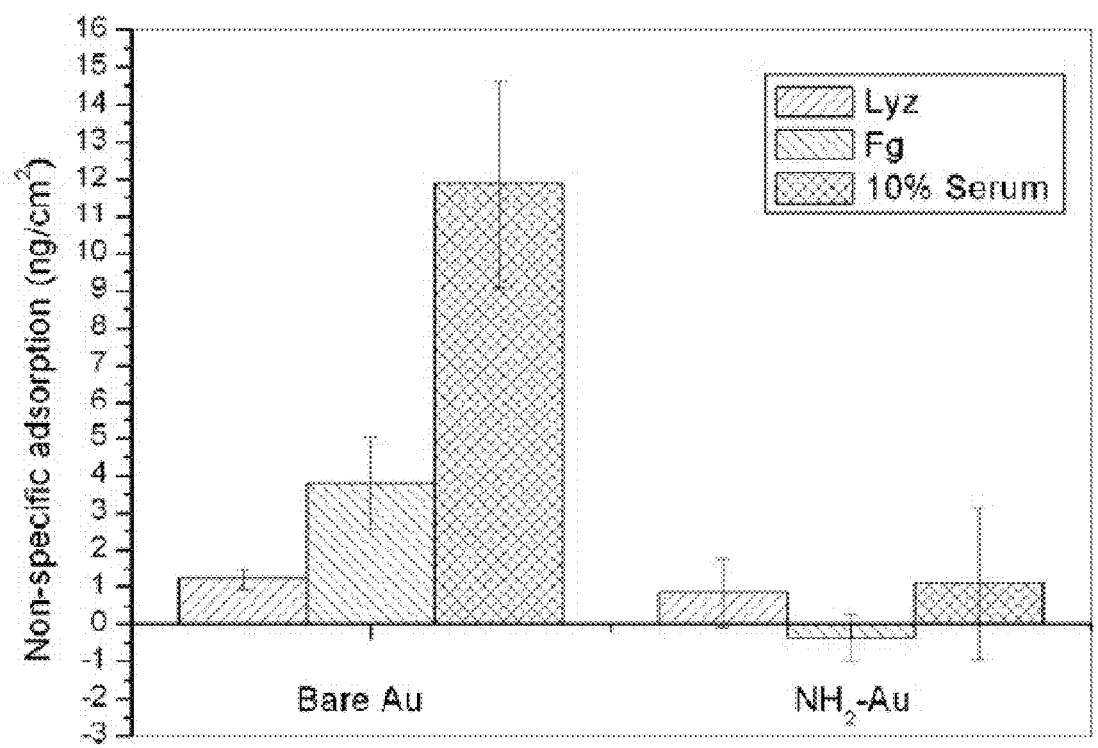
FIG. 16 compares non-specific protein adsorption (fibrinogen, 1 mg/mL; lysozyme, 1 mg/mL; and 10% serum in PBS) to bare gold (Bare Au) and $NH_2$-SAM surfaces ($NH_2$—Au) modified by a catechol initiator and ATRP of SBMA as measured by SPR. A full monolayer of adsorbed protein on the surface is equivalent to about 270 ng/cm$^2$. Error bars represent the standard deviations of the mean (n=4).

Representative catechol initiators were adhered to both bare gold and NH$_2$—SAM surfaces in Tris-HCl buffer (pH=8.5). Then SBMA was grafted from the initiator via ATRP as shown in FIG. 14. The ATR-FTIR spectrum of the pSBMA-coated NH$_2$—Au surface shows strong absorbance peaks at 1193 cm$^{-1}$ and 1044 cm$^{-1}$, which correspond to CO and SO$_3$ stretches, respectively, attributed to a surface coated with pSB. Single-protein solutions of fibrinogen (Fg) and lysozyme (Lyz) and 10% blood serum were used as model probe proteins to evaluate the nonfouling properties of the SBMA treated surfaces. These surfaces were further evaluated for protein adsorption from undiluted blood plasma and serum and for long-term *P. aeruginosa* adhesion/biofilm formation. Non-specific protein adsorption on these two surfaces were measured by SPR and compared. FIGS. 15A and 15B show typical SPR sensorgrams of the SBMA grafted to catechol-modified bare gold and NH$_2$-treated surfaces, respectively. These sensorgrams indicate the low levels of non-specific protein adsorption to these surfaces following exposure to Lyz, Fg, and 10% blood serum. These results are summarized in FIG. 16, where it can be seen that both surfaces have low fouling, indicating the successful anchoring of the initiator and grafting of SBMA via ATRP. However, only the NH$_2$-treated (pSBMA-catechol-NH$_2$-gold) surface achieved ultra-low fouling (<5 ng/cm$^2$). Although the adsorption of Lyz, Fg, and 10% blood serum was very low on the bare gold coated (pSBMA-catechol-gold) surface, this surface was not sufficient for resisting protein adsorption from complex media such as undiluted human plasma/serum and bacteria. This can be attributed to an insufficiently high pSBMA surface packing density on the bare gold surface. Previously, it was shown that catechol has strong anchoring interaction (a pull-off force of 2.2 nN for a single-molecular pair) with an NH$_2$ coating. The specific interactions between catechol and the NH$_2$ groups on the NH$_2$ SAM provides a strong bound and uniform initiator layer on the surface to provide a pSB brush. The measured amounts of adsorbed Lyz, Fg, and 10% serum of $0.8\pm0.9$ ng/cm$^2$, $-0.4\pm0.6$ ng/cm$^2$, and $1.1\pm2.0$ ng/cm$^2$ (FIGS. 15 and 16), respectively, were all within one SD of the limit of detection for the sensor (about 0.3 ng/cm$^2$).

Figure 17:
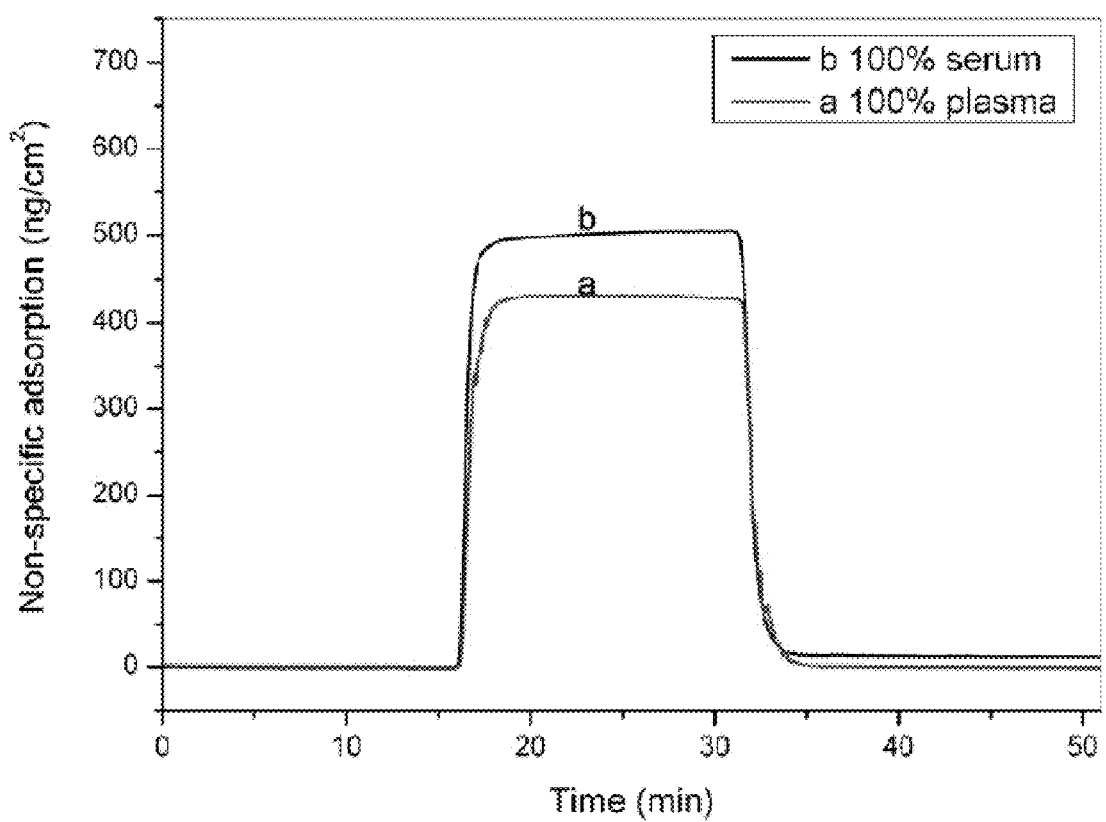
FIG. 17 compares non-specific protein adsorption (100% human serum and 100% human plasma) to a representative surface of the invention (pSBMA-catechol-$NH_2$-gold surface) as measured by SPR.
Figure 18:
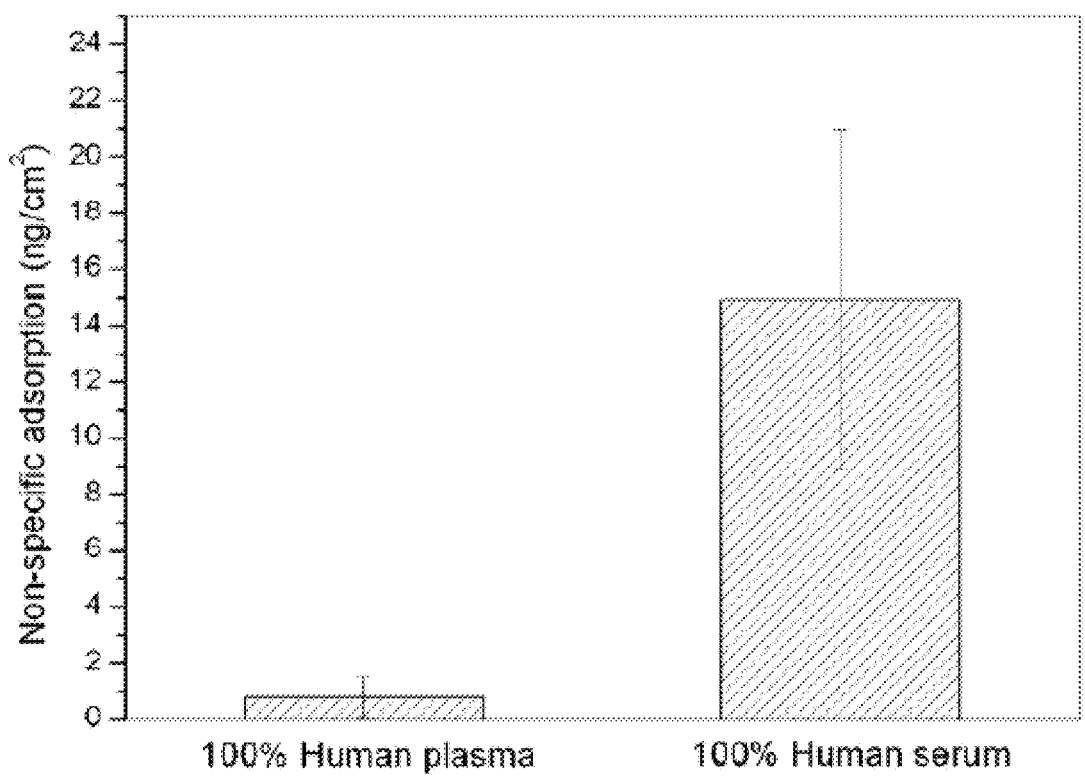
FIG. 18 compares non-specific protein adsorption (100% human serum and 100% human plasma) to a representative surface of the invention (pSBMA-catechol-$NH_2$-gold surface) as measured by SPR. A full monolayer of adsorbed protein on the surface is equivalent to about 270 ng/cm$^2$ based on the amount of fibrinogen that adsorbs to a methyl-terminated SAM. The error bars represent the standard deviations of the mean (n=4).
Figure 19A:
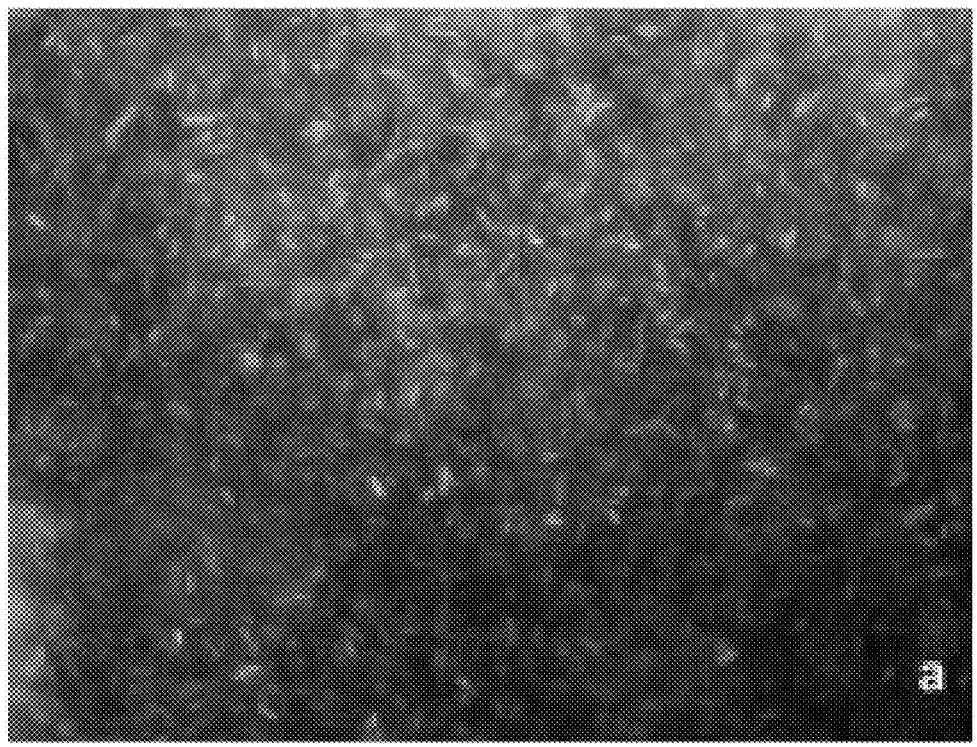
FIGS. 19A-19D are fluorescence microscopy images of *P. aeruginosa* attachment to bare glass after 2 days (FIG. 19A) and pSBMA-catechol-$NH_2$-glass surfaces after 1 day (FIG. 19B), 2 days (FIG. 19C), and 3 days (FIG. 19D).
Figure 19B:
Figure 19C:
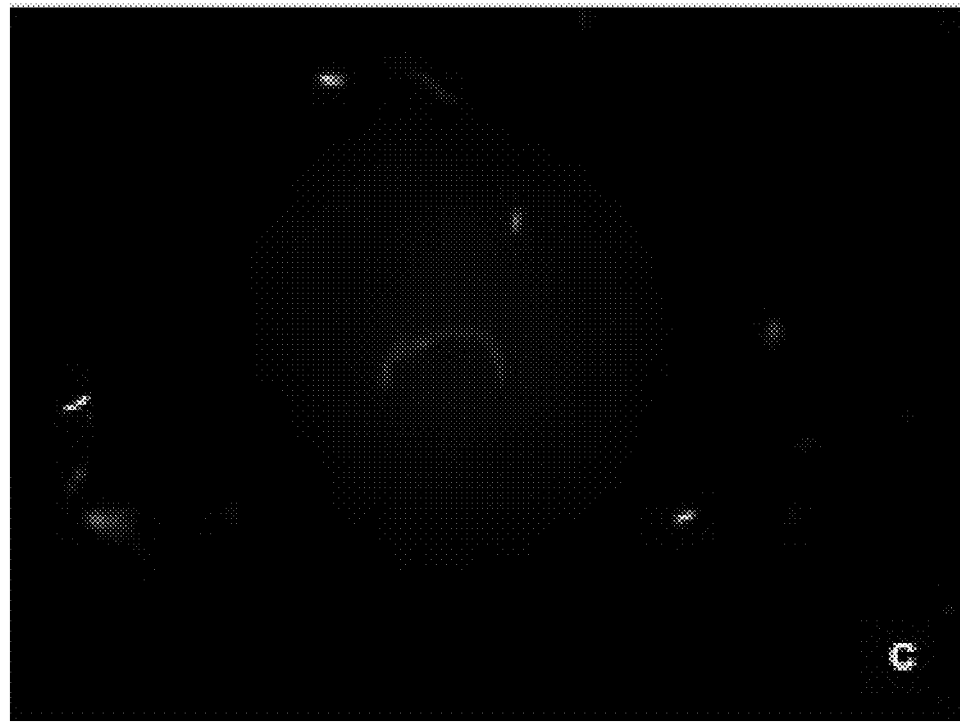
Figure 19D:
Figure 20:
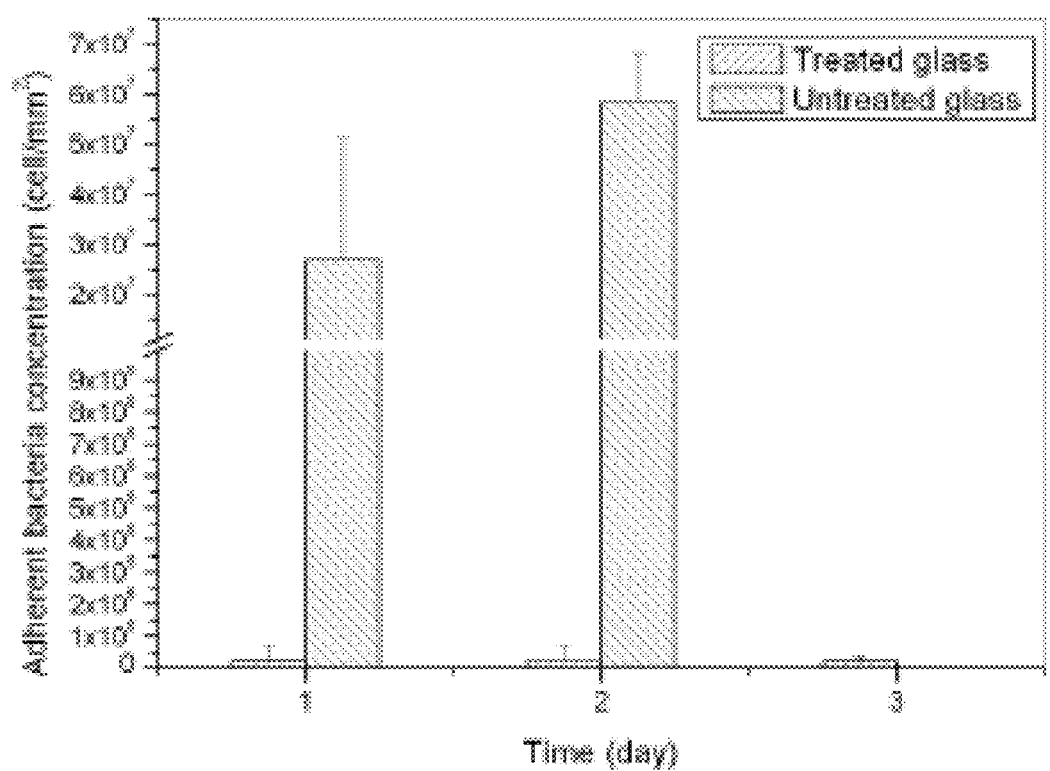
FIG. 20 compares in situ *P. aeruginosa* attachment to the untreated glass and pSBMA-catechol-$NH_2$-glass surfaces over 3 days of exposure. The data represents the mean±SD for 10 images of each sample (n=10). The bare glass surface was completely covered by bacteria after 2 days, thus no data were collected for the bare-glass surface beyond 2 days.

Undiluted human blood plasma and serum are among the most complex media and are far more demanding than single-protein solutions or 10% blood serum. For example, 100% human serum contains roughly 53-55 mg/mL of total protein. The nonfouling properties of the pSBMA-catechol-NH$_2$-gold surface coating was tested under more demanding conditions by exposing the coated surface to undiluted human plasma and serum. FIG. 17 shows typical SPR sensorgrams of pSBMA-catechol-NH$_2$-gold surfaces exposed to 100% human serum and plasma indicating the nonfouling properties of this coating in complex media. These results are summarized in FIG. 18, which shows that the pSBMA-catechol-NH$_2$-gold surface had nonspecific protein adsorption levels of $0.8\pm0.7$ ng/cm$^2$ and $14.9\pm6.0$ ng/cm$^2$ from 100% human serum and plasma, respectively. The human serum had no added anticoagulant, while the human plasma has citric phosphate dextran (CPD) added. Neither CPD itself nor human serum with added CPD alters protein adsorption results. Furthermore, NH$_2$ SAM coated gold substrates grafted with pSBMA were immersed in PBS at room temperature for 42 days without losing their ultra-low fouling properties to 100% serum and plasma.

PEG-coated surfaces reduce the adhesion of *P. aeruginosa* as compared to their control samples over a short period of time (e.g., for a few hours). The accumulation of *P. aeruginosa* over one day on pSBMA modified glass chips formed via surface-initiated ATRP using a silane initiator. The results from that study indicated the excellent performance of pSBMA for resisting bacteria adhesion and biofilm formation. The long-term (3 day) accumulation of P. aeruginosa on the pSBMA-catechol-NH$_2$-glass surfaces was observed in situ in a laminar flow chamber. Bare glass was used as a reference. The tested chips were observed each day to study the bacterial behaviors on the surfaces. FIGS. 19A-19D display representative microscopy images of accumulated P. aeruginosa on treated and untreated glass slides over the course of the 3 days growth test and shows the quantitative changes in the number of adherent bacteria with time. On the untreated glass surface, a confluent biofilm of P. aeruginosa was observed by the second day of the growth experiment. However, no biofilm was found on the treated surfaces over the 3-day growth test. The density of adherent bacteria remained very low (about $2.7 \times 10^5$ cell/mm$^2$), especially when compared to that on of the bare glass surface by the second day (about $5.8 \times 10^7$ cell/mm$^2$). Even after 3 days of culture, the adhesion of P. aeruginosa on the pSBMA-catechol-NH$_2$-glass surface was 99.5% less than that on the 2-day bare glass (p<0.05). The results demonstrate the strong and stable anchoring properties of the catechol initiator, which allow for the creation of well-packed pSB nonfouling surfaces with appropriate surface packing densities.

Figure 21:
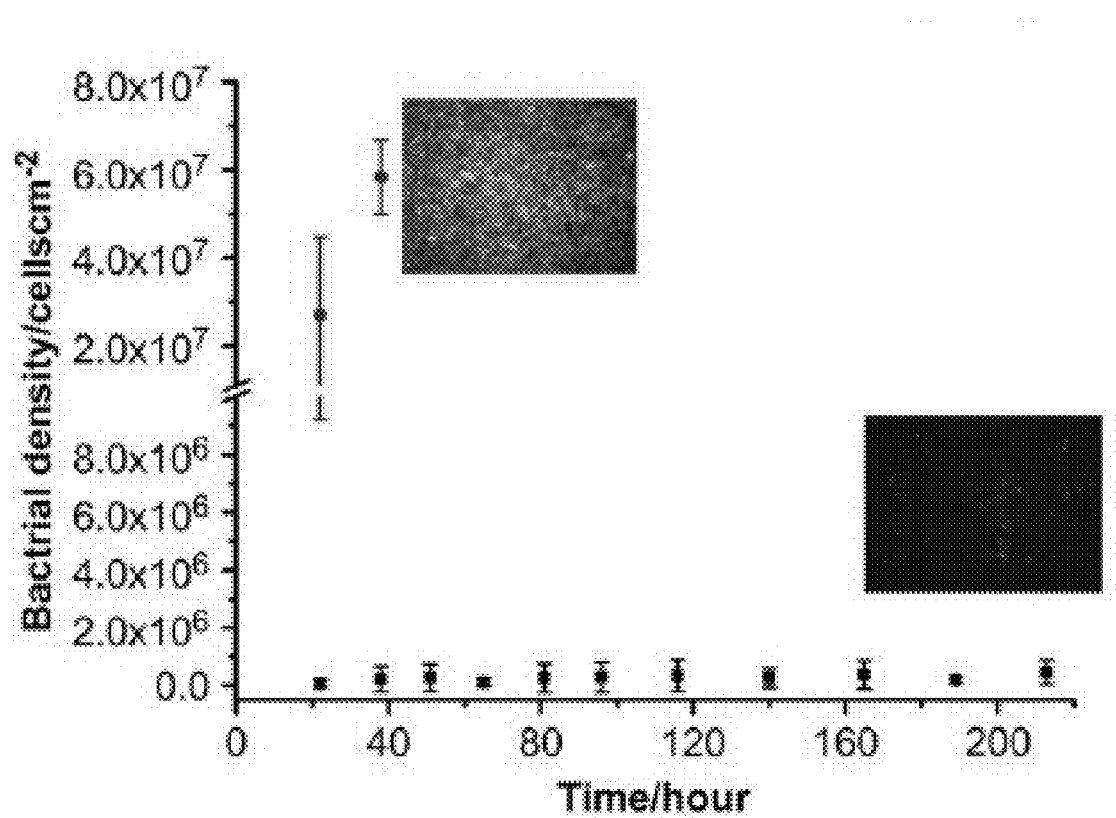
FIG. 21 compares *P. aeruginosa* accumulation on untreated glass (●) and pSBMA glass (■) surfaces as a function of time at 25° C. pSBMA brushes were grafted from a glass surface coated with 3,4-dihydroxyphenyl-L-alanine initiators.

FIG. 21 compares P. aeruginosa accumulation on untreated glass (●) and pSBMA glass (■) surfaces as a function of time at 25° C. pSBMA brushes were grafted from a glass surface coated with 3,4-dihydroxyphenyl-L-alanine initiators. The pSBMA surfaces were then exposed to P. aeruginosa PAO1 with GFP at 25° C. Results shown in FIG. 21 indicated that pSBMA coated surfaces dramatically reduce biofilm formation over 9 days, where accumulated bacterial cells on the pSBMA surface are less than 1 percent of that accumulated on the unmodified glass at 38 hours.

In one embodiment, the invention provides a copolymer having a plurality of positively charged repeating units, a plurality of negatively charged repeating units; and an adhesive moiety (e.g., catechol moiety) effective for immobilizing the polymer to a surface thereby imparting low fouling properties to the polymer-modified surface. As noted above, in one embodiment, the copolymer is substantially electronically neutral (polyampholyte). In one embodiment, the copolymer includes a single adhesive moiety. In one embodiment, the copolymer includes two adhesive moieties.

Two polyampholytes of equimolar charged monomers with two types of catecholic anchor groups were synthesized (one via ATRP and the other via free radical polymerization) of an ion-pair comonomer. Two resulting polyampholytes are nonfouling without the need to optimize their surface ratios as in the case of randomly mixed charge nonfouling materials.

Figure 22:
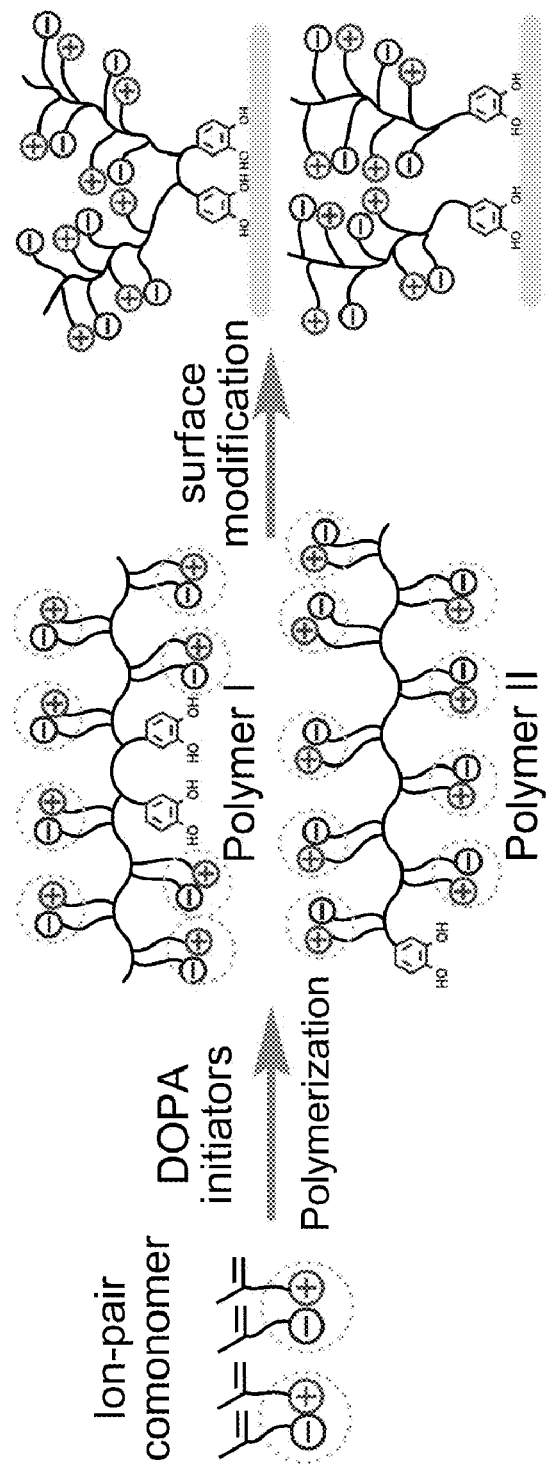
FIG. 22 is a schematic illustration of a representative method of the invention for preparing a representative surface of the invention: polymerization of a representative ion-pair comonomer with catechol initiators to provide representative polyampholytes (Polymer I and Polymer II) that are then grafted to surfaces to provide representative polyampholyte-coated surfaces of the invention.

FIG. 22 is a schematic illustration of a representative method of the invention for preparing a representative surface of the invention: polymerization of a representative ion-pair comonomer with catechol initiators to provide representative polyampholytes (Polymer I and Polymer II) that are then grafted to surfaces to provide representative polyampholyte-coated surfaces of the invention.

Figure 23:
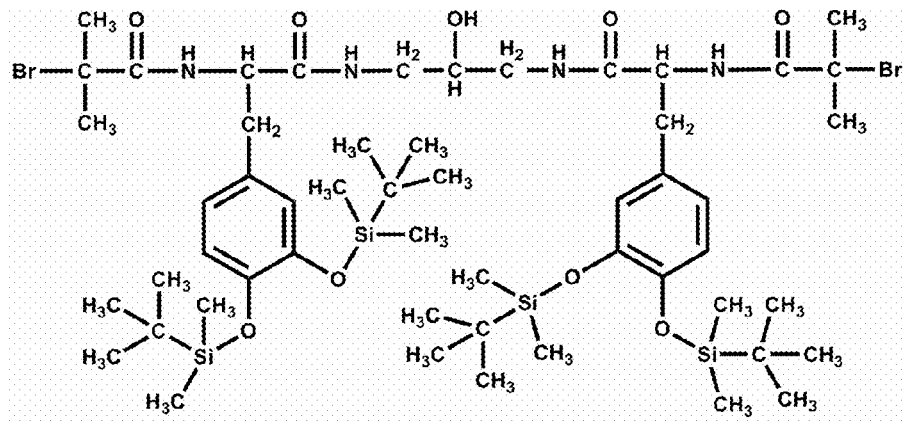
FIG. 23 illustrates the chemical structures of useful TBDMS-protected initiators (Initiator 1 and Initiator 2) and a representative ion-pair comonomer (METMA•MES) useful in the methods of the invention.
Figure 23:
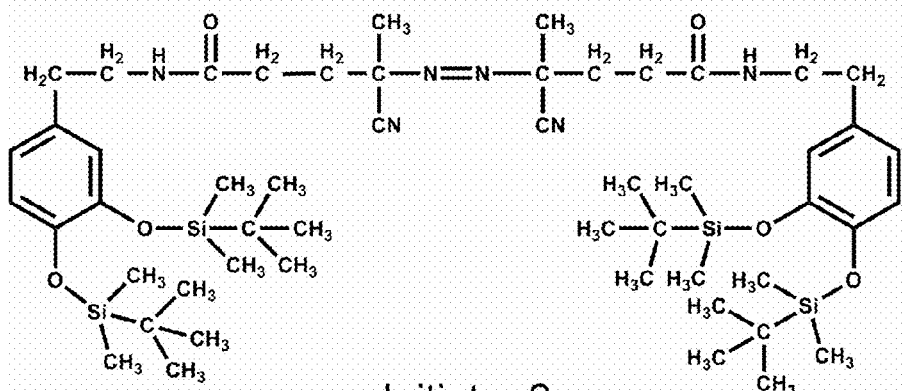
Figure 23:
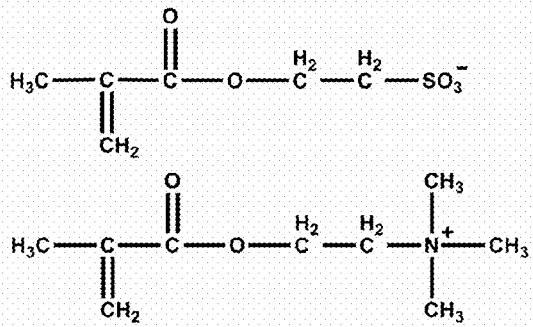

The ion-pair comonomer (METMA•MES) was synthesized from [2-(methacryloyloxy)ethyl]trimethylammonium chloride and 2-sulfoethyl methacrylate as described in Example 9. Two initiators (Initiator 1 and Initiator 2) with protected catecholic anchor groups were prepared as described in Example 9. The chemical structures of Initiator 1 and Initiator 2 are shown in FIG. 23. It can be seen that Initiator 1 can be used to initiate atom transfer radical polymerization (ATRP) and that Initiator 2 is a typical initiator for free radical polymerization. Each was modified to include an adhesive catechol group as an anchor.

Representative polyampholyte of the invention, Polymer I ($M_n$ 19143) was obtained by ATRP of METMA•MES from Initiator 1 and representative polyampholyte of the invention, Polymer II ($M_n$ 28276) was obtained by free radical polymerization of METMA•MES from Initiator 2. The preparation and characterization of the polymers and surfaces modified by the polymers are described in Example 9. Due to the different structures of Initiator 1 and Initiator 2, the adhesive groups are located at different positions in the polymer chains. For Polymer I, the two catechol groups are in the middle of the chain, and for Polymer II, the catecholic adhesive groups are located at the end(s) of the polymer chain. For free radical polymerization, two common types of termination reactions are combination and disproportionation. Because free radicals at the both ends of the growing poly (METMA•MES) chain are sterically hindered due to the presence of methyl groups, termination reaction by combination is impeded (catechol groups are at both ends), and termination reaction by disproportionation predominates (catechol groups are only at one end). Both of the polyampholytes were deprotected by tetrabutylammonium fluoride (TBAF), a mild de-protecting reagent, to remove the TBDMS groups before their usage for surface modification. A THF-water system was employed when the adhesive polymers were anchored to gold used as a model surface as described in Example 9.

The film thickness of the modified surfaces was measured by an ellipsometer. The surface modified by Polymer I had a film thickness of 5.75±2.20 nm (n=10). The surface modified by Polymer II had a film thickness of 6.94±1.88 nm (n=10). The thicker film of Polymer II than that of Polymer I can be explained by the fact that the molecular weight of Polymer II is greater than that of Polymer I. The modified surfaces were also characterized by ATR-FTIR and showed strong absorbent peaks at 1039 cm$^{-1}$, 1180 cm$^{-1}$ and 1729 cm$^{-1}$, corresponding to SO$_3$, C—O, and C=O stretches. ESCA was employed to determine their surface compositions quantitatively and the ratio of the atomic percentage of nitrogen and sulfur was used to quantify the ratio of METMA and MES on the polymer chains. The N/S ratios by ESCA for surfaces modified by Polymer I and Polymer II were 1.00±0.05 (n=4) and 0.96±0.06 (n=4), respectively. For these results, it can be concluded that the statistical METMA/MES ratios of Polymer I and Polymer II are 1:1, which demonstrates that two homogeneously mixed polyampholytes with overall charge neutrality were obtained.

Figure 24:
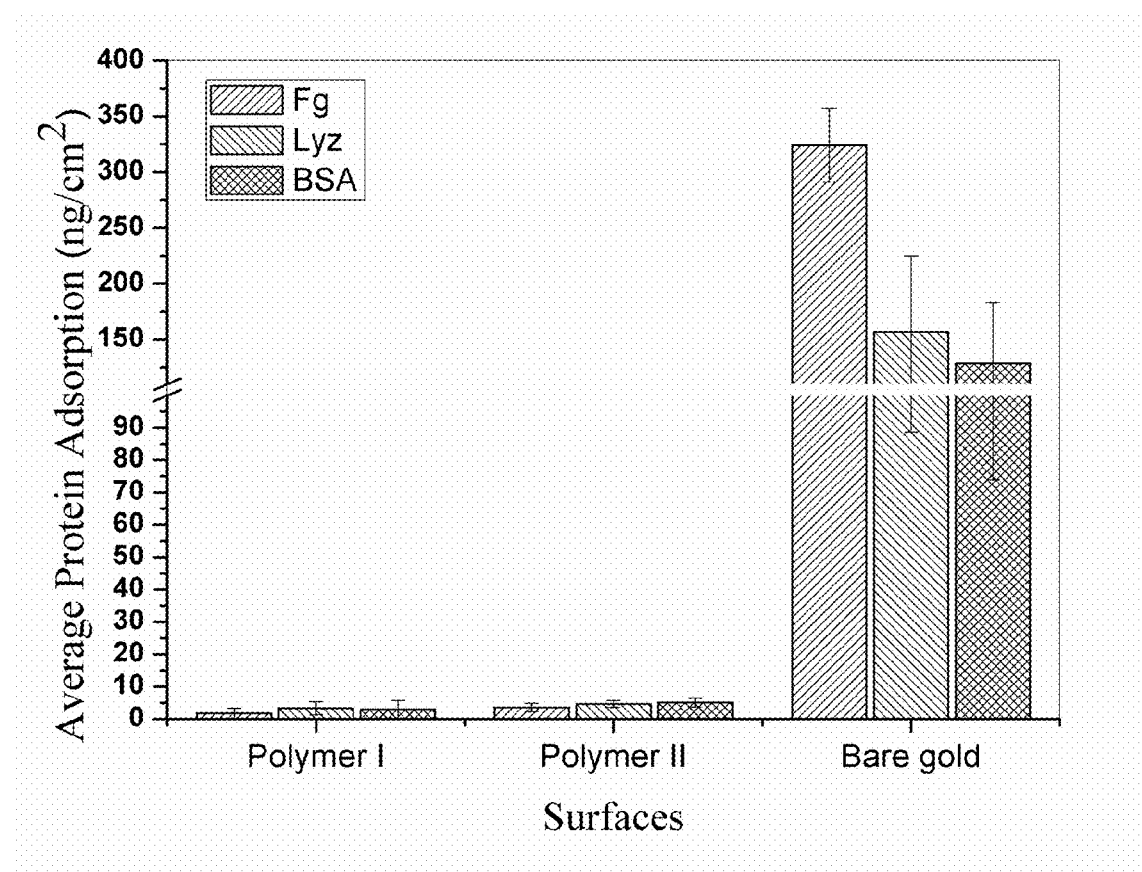
FIG. 24 compares non-specific protein adsorption (Fg, Lyz, bovine serum albumin (BSA)) to surfaces coated with representative polyampholytes of the invention (Polymer I and Polymer II). Error bars represent standard deviations of the mean (n=4).
Figure 25:
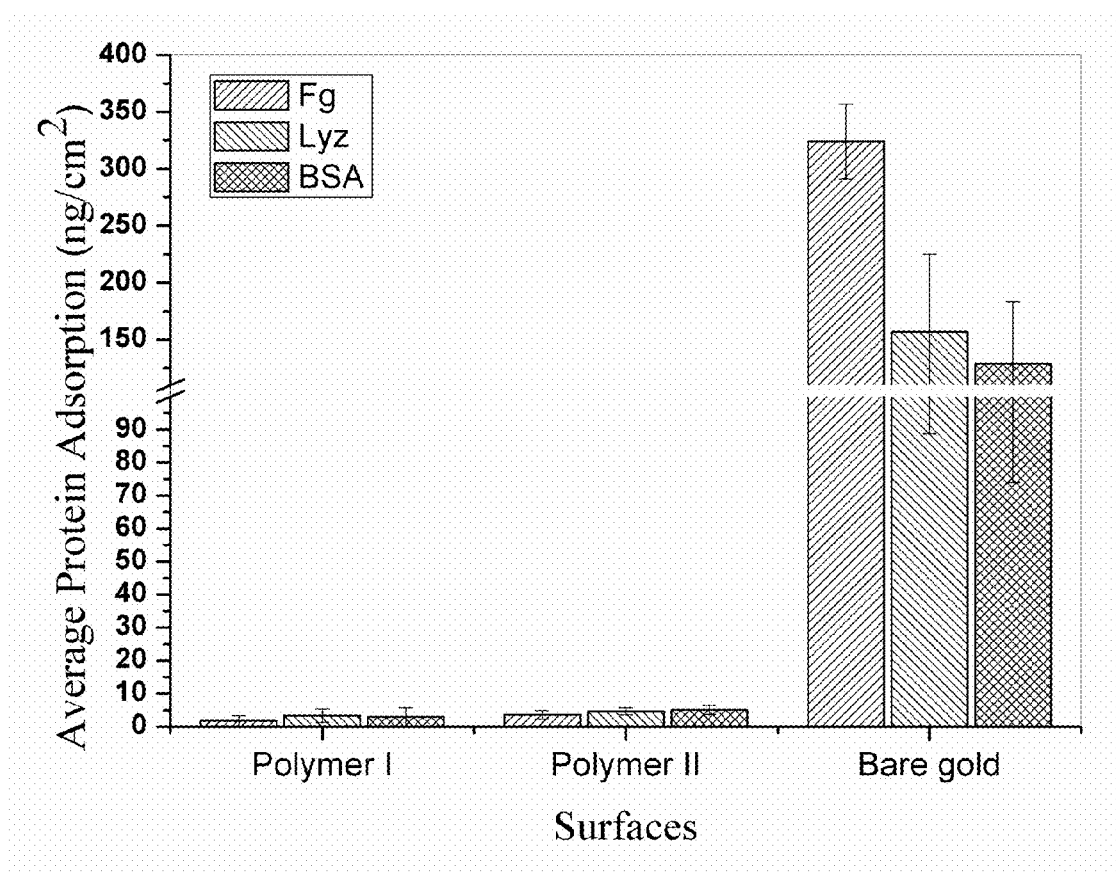
FIG. 25 compares typical SPR sensorgrams showing fibrinogen adsorption to representative polyampholyte-coated surfaces of the invention (Polymer I and Polymer II) and a bare gold surface.
Figure 26:
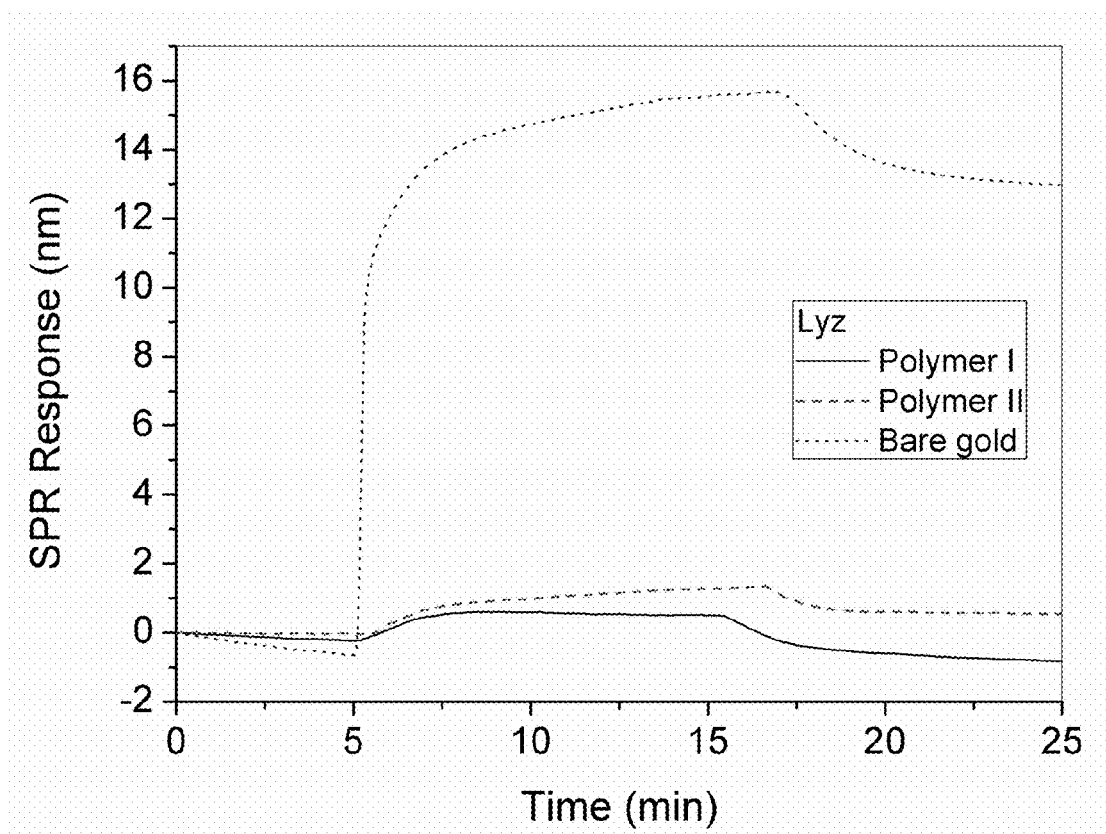
FIG. 26 compares typical SPR sensorgrams showing lysozyme adsorption to representative polyampholyte-coated surfaces of the invention (Polymer I and Polymer II) and a bare gold surface.
Figure 27:
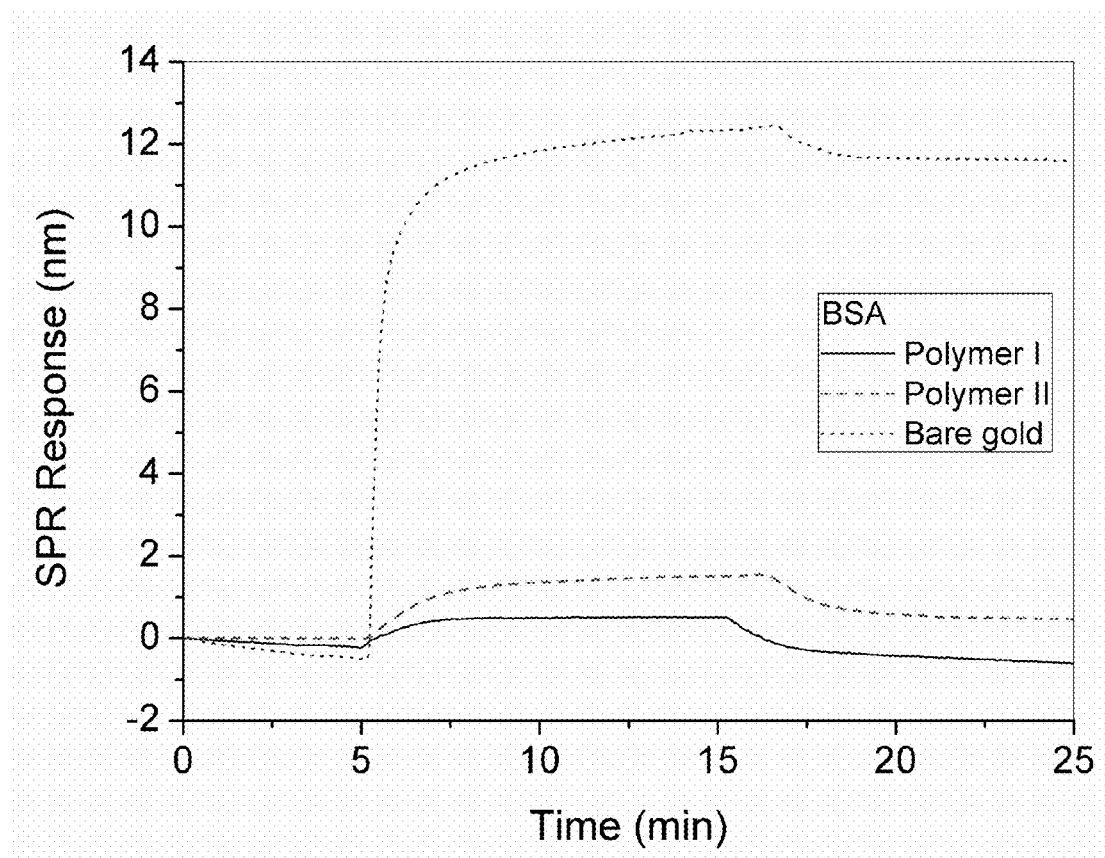
FIG. 27 compares typical SPR sensorgrams showing bovine serum albumin (BSA) adsorption to representative polyampholyte-coated surfaces of the invention (Polymer I and Polymer II) and a bare gold surface.

The protein-resistant properties of the modified surfaces were tested by a SPR sensor. The results are summarized in FIG. 24. The adsorption of Fg, Lyz, and BSA was measured simultaneously in a four-channel SPR. Typical SPR sensor-grams are illustrated in FIGS. 25-27, respectively. The measured amounts of adsorbed Fg, Lyz, and BSA are 1.7±1.6, 3.3±2.0, 2.9±2.8 ng/cm$^2$ for Polymer I, and 3.5±1.3, 4.6±1.1, 5.0±1.4 ng/cm$^2$ for Polymer II, respectively. Thus, each modified surface exhibits nonfouling properties. The nonfouling behaviors of the coated surfaces can be explained by the strong hydration layer on the surface coming from the neutral charged and the nearly perfect alternating METMA and MES on the side chains of the polymers. Polymer II modified surfaces gave slightly higher nonspecific protein adsorption than those of Polymer I, which can be attributed to the differences in polymer structures noted above. The main composition of Polymer II results from termination reaction by disproportionation, which has a single catechol group at the end of the polymer chain. In comparison to Polymer II, Polymer I has two catechol groups for stronger binding and two nonfouling chains for higher chain packing density, leading to denser adlayers and lower protein adsorption. In addition, even if there exists a small amount of Polymer II with two catechol groups resulting from termination by combination, their binding onto a gold surface is not expected to be strong to hold both anchors at the far ends of a polymer chain. If only one end is attached, then unbounded catecholic groups at the other end will lead to some nonspecific protein adsorption.

In summary, two adhesive polyampholytes were synthesized by the polymerization of an ion-pair comonomer using two types of catecholic initiators. ESCA results show the N/S ratios of 1 and 0.96 for the gold surfaces modified by Polymer I and Polymer II, respectively. These neutral charged surfaces give excellent nonfouling properties from protein solutions of Fg, Lyz and BSA.

The following examples are provided for the purpose of illustrating, not limiting, the invention.

EXAMPLES

Materials

Dopamine.hydrochloride (≥98.5%), imidazole (99%), sodium carbonate.decahydrate, 3,4-Dihydroxyphenyl-L-alanine (DOPA), 2-bromoisobutyric acid, dicyclohexyl carbodiimide (DCC), N-hydroxysuccinimide, copper (I) bromide (99.999%), copper (II) bromide (99.999%), bromoisobutyryl bromide (BIBB 98%), N-(3-sulfopropyl)-N-(methacryloxyethyl)-N,N-dimethylammonium betaine (SBMA 97%), 2,2'-bipyridine (BPY 99%), 3-aminopropyltrimethoxysilane (97%), 11-mercapto-1-undecanol (97%), 1-dodecanethiol (98+%), 3,3'-diaminobenzidine (DAB), methanol and tetrahydrofuran (HPLC grade), 4,4'-azobis(4-cyanovalerate), [2-(methacryloyloxy)ethyl]trimethylammonium chloride (75% wt. % solution in water), and albumin (from bovine serum, BSA) were purchased from Sigma-Aldrich. 2-Sulfoethyl methacrylate (>90%) was purchased from Polysciences. Tetrabutylammonium fluoride (TBAF, 1 M solution in THF containing about 5% water), 1,3-diamino-2-hydropropane, tert-butyl chlorodimethylsilane (TBDMS, 98%), and silver (I) oxide (>99%) were purchased from Acros. 11-Amino-1-undecanethiol ($HS(CH_2)_{11}NH_2$) was purchased from Dojindo Molecular Technologies (Gaithersburg, Md.). Sodium borate 10-hydrate was purchased from J. T. Baker. Fibrinogen (fraction I from bovine plasma), lysozyme (from chicken egg white), phosphate buffer saline (PBS, pH 7.4, 0.15 M, 138 mM NaCl, 2.7 mM KCl), and 3-(N-morpholino) propanesulfonic acid (MOPS, minimum 99.5%, titration) were purchased from Sigma Chemical Co. Tris crystallized free base (molecular biology grade) was purchased from Fisher Scientific. Pooled human plasma and serum were purchased from BioChemed Services (Winchester, Va.). Ethanol (absolute 200 proof) was purchased from AAPER Alcohol and Chemical Co. Water was purified using a Millipore water purification system with a minimum resistivity of 18.0 MΩ·cm. THF for reactions and washings was dried with sodium before use. N,N-dimethylformamide and dichloromethane were dried with phosphorous oxide and then distilled. N-succinimidyl 2-bromoisobutyrate (1), 3,4-bis(terbutyldimethylsiloxyl)-L-phenylalanine (2), Boc-(DOPA$_2$ (TBDMS)$_4$—NHS), CBMA monomer, and trifluoroacetic acid salt of 2-aminoethyl 2-bromoisobutyrate were prepared following reported procedures. Molecular weights of the polymers were determined using an aqueous gel permeation chromatograph (GPC) (Waters 2695 Separations Module) with a Waters 2414 refractive index detector and a Waters ultrahydrogel 250 column (7.8 mm×300 mm). The buffer solution (0.05 M Tris buffer+1.0 M NaCl) was used as the eluent with a flow rate of 0.5 mL/min at 35° C. All samples were filtered through 0.2 μm PTFE filters prior to injection. The system was calibrated with narrow molecular weight polyethylene oxide standards.

Example 1

Synthesis of a Representative pSB-Catechol Polymer: pSBMA-Catechol

In this example, the synthesis of a representative polymer of the invention, pSBMA-catechol, is described. The synthesis is schematically illustrated in FIG. 2.

2-[3,4-Di(t-butyldimethylsilyloxy)]phenethylamine (1)

The protection of the catechol oxygens was achieved by the reaction of dopamine.HCl and t-butyldimethylsilyl (TBDMS) chloride to provide Compound 1 (5.19 g, 95%), as shown in the Step 1 of FIG. 1, using a method as described in Ikeuchi M. et al., A new synthesis of phenolic 1-hydroxy-1-phenyl-2,3,4,5-tetrahydro-1H-3-benzazepines, Heterocycles 2005; 65(12):2925-2934. $^1$H NMR (300 MHz, CDCl$_3$) δ: 6.79 (d, 1H, J=8.1 Hz), 6.68 (d, 1H, J=8.1 Hz), 6.64 (d, 1H, J=2.1 Hz), 3.01 (t, 2H, J=7.5 Hz), 2.76 (t, 2H, J=7.2 Hz), 0.99 (s, 18H), 0.19 (s, 12H).

2-Bromo-2-methyl-N-[2-(3,4-di(t-butyldimethylsilyloxy)-phenyl)ethyl]propionamide (2)

Compound 2 was synthesized by reaction of Compound 1 and BIBB, as shown in step 2 of FIG. 1, using a method as described in Jones D. M. et al., Surface-initiated polymerizations in aqueous media: Effect of initiator density. Langmuir 2002; 18(4):1265-1269. The crude product was subjected to chromatography on SiO$_2$ with hexane-ethyl acetate (2:1) to obtain a white crystal product (3.74 g, 49.3%). $^1$H NMR (300 MHz, CDCl$_3$) δ: 6.79 (d, 1H, J=8.1 Hz), 6.68 (d, 1H, J=8.1 Hz), 6.64 (d, 1H, J=2.1 Hz), 3.49 (t, 2H, J=7.5 Hz), 2.74 (t, 2H, J=7.2 Hz), 1.93 (s, 6H), 0.99 (s, 18H), 0.20 (s, 12H).

Preparation of pSBMA-Catechol.

The polymerization of SBMA was carried out using Compound 2 as an initiator in solution, as shown in FIG. 2, using a method as described in Jiang S. et al., Highly Protein-Resistant Coatings from Well-Defined Diblock Copolymers Containing Sulfobetaines, Langmuir 2006; 22:2222-2226. Instead of methanol, a mixture of methanol and water (4:1, v/v) was used as the solvent.

Molecular weights of the polymers were determined using aqueous gel permeation chromatography (GPC) (Waters 2695 Separations Module) fitted with a Waters 2414 refractive index detector and a Waters ultrahydrogel 250 column (7.8 mm×300 mm). The buffer solution (0.05 M Tris buffer+1.0 M NaCl) was used as the eluent with a flow rate of 0.5 mL/min at 35° C. All samples were filtered through 0.2 micron PTFE filters prior to injection. The system was calibrated with narrow molecular weight polyethylene oxide standards. Before surface adhesion, the TBDMS groups of Compound 2 were removed using TBAF in order to achieve complete deprotection. A solution with 1 mM catechol polymer and 5 mM TBAF in THF was stirred overnight. The suspension was centrifuged and the supernatant was removed. The remaining colorless solid was washed three times with THF and dried under reduced pressure.

Example 2

Surface Coating with a Representative pSB-Catechol Polymer: pSBMA-Catechol

In this example, coating surfaces with a representative polymer of the invention, pSBMA-catechol, is described.

Self-Assembled Monolayer (SAM) Preparation.

BK-7 glass chips (Schott Glass) were coated with an adhesion-promoting titanium layer (thickness 2 nm) and a surface plasmon active gold layer (48 nm) by electron beam evaporation under vacuum. Before SAM preparation, the substrates were washed with water and pure ethanol, cleaned under UV light, and washed with water and pure ethanol. Hydroxyl and methyl terminated SAMs were formed by soaking gold-coated substrates in 0.5 mM ethanolic solutions of thiols at room temperature overnight. Following SAM formation, the substrates were rinsed with ethanol and dried with filtered air. $NH_2$-SAMs were formed overnight by soaking substrates in a 0.5 mM ethanolic solution of $HS(CH_2)_{11}$—$NH_2$ containing 3% (v/v) $N(CH_2CH_3)_3$. The substrates were then rinsed sequentially with ethanol, an ethanolic solution with 10% $CH_3CO_2H$ (v/v), and ethanol followed by drying in a stream of filtered air. Jiang S. et al., Improved method for the preparation of carboxylic acid and amine terminated self-assembled monolayers of alkanethiolates, Langmuir 2005; 21(7):2633-2636.

Preparation of $NH_2$-Glass Chips.

$NH_2$-glass chips used in long-term bacteria adhesion/biofilm formation experiments were prepared using 3-aminopropyltrimethoxysilane, following a silane procedure as described in Jiang S. et al., Superlow Fouling Sulfobetaine and Carboxybetaine Polymers on Glass Slides, Langmuir 2006; 22:10072-10077.

Surface Modification.

Clean substrates were incubated in a solution of catechol-containing zwitterionic polymer (5 mg/mL) at room temperature for 24 h. The substrates were then extensively rinsed with DI water to remove unbound polymer. Adsorption was performed in 0.1 M MOPS buffer (pH 6.0) or 10 mM Tris-HCl buffer (pH 8.5).

Example 3

Properties of Surfaces Coated with a Representative pSB-Catechol Polymer: pSBMA-Catechol In this example, the properties of surfaces coated with a representative polymer of the invention, pSBMA-catechol, is described.

Protein Adsorption.

Protein solutions were flowed for 15 min on a custom-built surface plasmon resonance (SPR) sensor from the Institute of Photonics and Electronics, Academy Sciences (Prague, Czech Republic) as described in Jiang S. et al., DNA-directed protein immobilization on mixed self-assembled monolayers via a streptavidin bridge, Langmuir 2004; 20(19):8090-8095. Briefly, the SPR sensor is based on the Kretschmann geometry of the attenuated total reflection (ATR) method and wavelength modulation. Solutions of fibrinogen and lysozyme in PBS (1.0 mg/mL), 10% human serum in PBS (0.15 M, pH 7.4), 100% human serum, and 100% human plasma were flowed over the surfaces at a flow rate of 0.05 mL/min for 15 min. A surface-sensitive SPR detector was used to monitor protein-surface interactions in real time. In this work, the wavelength shift between two buffer baselines before and after protein injection was used to measure the change in surface concentration (mass per unit area). For the SPR sensor used in the study, a 1 nm SPR wavelength shift at 750 nm represents a surface coverage of about 15 ng/cm$^2$ adsorbed proteins (Jiang S. et al., Strong Resistance of Phosphorylcholine Self-Assembled Monolayers to Protein Adsorption: Insights into Nonfouling Properties of Zwitterionic Materials, J. Am. Chem. Soc. 2005; 127:14473-14478).

Bacterial Species and Culture Conditions.

*Pseudomonas aeruginosa* PAO1 with a GFP expressing plasmid was used for adhesion and biofilm formation studies. *P. aeruginosa* was first cultured in a separate pure culture overnight at 37° C. on a trypticase soy broth (TSB) (BD, USA) agar plate (Wagner V. E. et al., Protein and bacterial fouling characteristics of peptide and antibody decorated surfaces of PEG-poly(acrylic acid) co-polymers, Biomaterials 2004; 25(12):2247-2263). The culture on an agar plates can be used for 2 weeks if kept at 4° C. Several colonies were used to inoculate 25 ml of TSB (10 g/L) containing 200 µg/mL of carbenicillin. These initial cultures were incubated at 37° C. with shaking at 100 rpm for 18 h and were then used to inoculate a second culture in 200 mL of appropriate medium.

Bacterial Adhesion Assay.

BST FC 281 Flow Cells, designed for monitoring and evaluating biofilm processes using microscopy and image analysis, were purchased from BioSurface Technologies. The FC 281 Flow Cell is a dual channel, flat plate flow cell designed for use with transmitted, fluorescent, or confocal microscopy. Parallel channels allow for direct side-by-side comparisons.

Standard 24 mm×60 mm glass cover slips coated with polymer films were fixed in the flow cell. Dimensions of the flow chamber are 50.5 mm (L), 12.5 mm (W), and 2 mm (deep). The flow chambers were sterilized and cleaned using a method as described in Jiang S. et al., Inhibition of bacterial adhesion and biofilm formation on zwitterionic surfaces, Biomaterials 2007; 28:4192-4199 and Wagner V. E. et al., Protein and bacterial fouling characteristics of peptide and antibody decorated surfaces of PEG-poly(acrylic acid) co-polymers, Biomaterials 2004; 25(12):2247-2263. PBS (pH 7.4) was first pumped through the flow cells to soak the surface. When the second suspended culture reached an optical density of 1.0 at 600 nm, bacteria were collected by centrifugation at 8000 g for 10 min at 4° C. The cell pellets were washed three times with sterile PBS and subsequently suspended in PBS to a final concentration of $10^6$ cells/mL. The cell suspension was pumped through the flow cell at a flow rate of 2.5 mL/min (shear stress of about 0.05 dyn/cm$^2$) until the chambers were full, and then flow was terminated and bacteria were allowed to adhere to the surfaces under static conditions for 30 min. After 30 min the appropriate sterile growth medium, TSB (10 g/L) with 100 µg/mL carbenicillin, was pumped into flow cell at a flow rate of 2.5 mL/min during the experiment. The vessel, connective tubing, and parallel flow reactor were shielded from light to prevent the photobleaching of the stain using aluminum foil. The effluent was collected in a waste container for proper disposal.

The bacterial accumulation was observed in situ. Because the *P. aeruginosa* strain used in this study carries green fluorescent protein (GFP) gene, samples could be imaged without staining. *P. aeruginosa* were observed directly with a CCD-CoolSNAP camera (Roper scientific, Inc., USA) mounted on Nikon Eclipse 80i with 100× oil lens and epifluorescent illumination through a FITC filter. A partially treated glass slide was also tested for the 70 h accumulation of *P. aeruginosa*.

Example 4

Synthesis of Representative pCB-Catechol Polymers

In this example, the syntheses of representative polymers of the invention, pCB-catechol, pCB-catechol$_2$, and pCB$_2$-catechol$_2$ are described. The synthesis of pCB$_2$-catechol$_2$ is illustrated schematically in FIG. 9. The synthesis of pCB-catechol$_2$ is illustrated schematically in FIG. 10.

Synthesis of pCB$_2$-Catechol$_2$

2-Bromo-2-methyl-N-1-carboxyl-2-[3,4-bis(t-butyldimethylsilyloxy)]-phenyl-ethyl propionamide (3)

N-Succinimidyl 2-bromoisobutyrate (0.528 g, 2.00 mM) was dissolved in dry DMF (2.5 mL) and 3,4-bis(t-butyldimethylsiloxyl)-L-phenylalanine (0.85 g, 2.00 mM) was added at once under N$_2$. The mixture was stirred on an ice-bath, then diisopropylethylamine (DIEA) (350 μL, 2 mM) was added via a syringe. The reaction mixture was kept in ice-bath for one hour. Its temperature was raised to room temperature for overnight. The mixture was treated with diluted solution of HCl (5%, 40 mL) and then extracted with EtOAc (30 mL). The organic layers were combined and washed with DI water (30 mL), and dried with anhydrous MgSO$_4$. The crude product was purified with silica gel with chloroform and 1% methanol as an eluent. 3,4-Bis(t-butyldimethylsilyloxy)-N-isobutyryl-L-phenylalanine was obtained as a white foam, (1.09 g, 90%). $^1$H NMR (CDCl$_3$) δ: 7.01-7.04 (d, 1H), 6.63-6.80 (m, 3H), 4.73-4.75 (m, 1H), 3.05-3.15 (m, 2H), 1.88-1.92 (d, 6H), 0.99 (s, 18H), 0.20 (s, 12H).

2-Bromo-2-methyl-N-1-(carbonyloxysuccinimide)-2-[3,4-bis-(t-butyldimethylsilyloxy)phenyl-ethyl propionamide (4)

Compound (4) was synthesized using the same synthetic procedure as 1, and the yield was 85%. $^1$H NMR (CDCl$_3$) δ: 7.01-7.03 (d, 1H), 6.64-6.79 (m, 3H), 4.72-4.74 (m, 1H), 3.05-3.15 (m, 2H), 2.86 (s, 4H), 1.88-1.92 (d, 6H), 0.99 (s, 18H), 0.20 (s, 12H).

N,N-(2-Hydroxy-1,3-propanediyl)-bis[2-(N-2-bromo-2-methyl propionamide)-3-(3,4-di(t-butyldimethylsilyloxy))phenyl]propanamide (Catechol$_2$-Br$_2$) (5)

The initiator 5 was synthesized from 4 and 1,3-diamino isopropyl alcohol. Compound 4 (1.4 g, 2.08 mmol) was dissolved in dry DMF (6 mL) and 1,3-diamino isopropyl alcohol (90 mg, 1.00 mmol) was added at once under N$_2$. The mixture was stirred on an ice-bath, then diisopropylethylamine (DIEA) (385 μL, 2.2 mM) was added via a syringe. The reaction mixture was kept in ice-bath for one hour. Its temperature was raised to room temperature for overnight. The mixture was treated with diluted solution of HCl (5%, 40 mL) and then extracted with EtOAc (30 mL). The organic layers were combined and washed with 30 mL DI water, dried (MgSO$_4$) and evaporated. The crude product was loaded onto a silica gel column with chloroform and 1% methanol as the eluent. Compound 5 was obtained as a yellow powder, the yield was 0.78 (65%). $^1$H NMR (CDCl$_3$) δ: 7.06 (m, 2H), 6.88 (m, 2H), 6.65-6.79 (m, 6H), 4.46-4.51 (m, 2H), 3.75-3.78 (t, 1), 2.90-3.46 (m, 8H), 1.84-1.93 (d, 12H), 0.99 (s, 36H), 0.19 (s, 24H).

Preparation of pCB$_2$-Catechol$_2$ (6).

Initiator 5, 26 mg (0.022 mM), BPY (20 mg, 0.13 mm), CuBr, 6.80 mg (0.047 mM), and CuBr$_2$, and 1.03 mg (0.005 mM) were placed into a three-necked flask. The system was degassed three times and filled with N$_2$, then 1 mL DMF (degassed) was added under N$_2$. The mixture was stirred for 20 min at room temperature. 1.0 g CBMA, dissolved in H$_2$O/DMF (2 mL/7 mL) was added into the reaction system. The polymerization reaction continued for 10 h. The resulting polymer precipitate was collected by filtration, and dissolved in H$_2$O again. The polymer solution was dialyzed for 2 days with DI water. The white powder (0.9 g, 90%) was obtained after removal of water. Before surface adhesion, the TBDMS groups of protected pCB$_2$-catechol$_2$ were removed using TBAF in order to achieve complete deprotection. A solution with 1.0 mM TBDMS protected pCB$_2$-catechol$_2$ and 10 mM TBAF in THF was stirred overnight. The suspension was centrifuged and the supernatant was removed. The remaining white powder (6) was washed three times with THF and dried under reduced pressure.

Synthesis of pCB-Catechol$_2$

2-Boc-DOPA$_2$-(TBDMS)$_4$-amidoethyl 2-bromoisobutyrate (Catechol$_2$-Br) (7)

Boc-DOPA$_2$(TBDMS)$_4$-NHS (1032 mg, 1.00 mM) was dissolved in dry DMF (5 mL) and trifluoroacetic acid salt of 2-aminoethyl 2-bromoisobutyrate (339 mg, 1.00 mM) was added at once under N$_2$. The mixture was stirred on an ice-bath, then diisopropylethylamine (DIEA) (385 mL, 2.2 mM) was added via a syringe. The reaction mixture was kept in ice-bath for one hour. The temperature was raised to room temperature for overnight. The mixture was treated with diluted solution of HCl (5%, 40 mL) and then extracted with EtOAc (30 mL). Organic layers were combined and washed with 30 mL DI water, dried (MgSO$_4$) and evaporated. The crude product was loaded onto a silica gel column with chloroform and 1% methanol as the eluent. Compound 7 was obtained as a white foam, (1.03 g, 91%). $^1$H NMR (CDCl$_3$) δ: 6.60-6.82 (m, 6H), 6.38-6.44 (m, 2H), 4.64-4.67 (m, 2H), 4.12-4.19 (m, 2H), 4.09-4.11 (m, 1H), 3.14-3.60 (m, 3H), 2.66-3.04 (m, 3H), 1.95 (d, 6H), 1.31 (s, 9H), 1.0 (m, 36H) 0.2 (m, 24H).

pCB-Catechol$_2$ (8).

Initiator 7, 52 mg (0.05 mmol), BPY (44 mg, 0.29 mmol), CuBr, 13.6 mg (0.094 mmol), and CuBr$_2$, 1.03 mg (0.005 mmol), were placed into a three-necked flask. The system was degassed three times and filled with N$_2$, then 1 mL DMF (degassed) added under N$_2$. The mixture was stirred for 20 min at room temperature. 1.0 g CBMA, dissolved in H$_2$O/DMF (2 mL/7 mL) was added into the reaction system. The polymerization continued for 10 h. The resulting polymer precipitate was collected by filtration, and dissolved in H$_2$O again. The polymer solution was dialyzed for 2 days with DI water, and white polymer powder (0.85 g, 85%) was obtained after removal of water. The molecular weight and molecular weight distribution of protected p-CB-catechol$_2$ were measured with GPC, Mn: 80 800 (against PEO), PDI is 1.22. The resulting polymer was deprotected with the same procedure as polymer 6 before using.

pCB-catechol was synthesized following the method described in Example 1 for pSB-catechol.

Example 5

Surface Coating with a Representative pCB-Catechol Polymer: pCBMA$_2$-Catechol$_2$ In this example, coating surfaces with a representative polymer of the invention, pCBMA$_2$-Catechol$_2$, is described.

Grafting pCB$_2$-Catechol$_2$ onto Bare Au Chip.

10 mg deprotected polymer was dissolved in 2 mL DI water (pH=3) in a 20 mL glass tube. 1 mL THF was added dropwise into this tube. The turbid polymer solution was sonicated for 10 min, then transferred to a Teflon cell. The cleaned Au chip, prepared as described in, was placed into the cell and submerged for 24 h. The chip coated with pCB$_2$-catechol$_2$ by this method was washed with DI water twice and dried with airflow before loaded on the SPR instrument.

Example 6

Properties of Surfaces Coated with a Representative pCB-Catechol Polymer: pCBMA$_2$-Catechol$_2$ In this example, the properties of surfaces coated with a representative polymer of the invention, pCBMA$_2$-catechol$_2$, is described.

Measurements of Protein Adsorption.

Protein adsorption was measured by a custom-built SPR sensor from the Institute of Photonics and Electronics, Academy Sciences (Prague, Czech Republic). Solutions of Fg and Lyz in PBS (1.0 mg/mL), 100% blood serum, and 100% blood plasma were flowed over the surfaces at a flow rate of 50 mL/min for 10 min. A surface-sensitive SPR detector was used to monitor protein-surface interactions in real time. In this work, the wavelength shift between two buffer baselines before and after protein injection was used to measure the change in surface concentration (mass per unit area). For the SPR sensor used in the study, a 1 nm SPR wavelength shift at 750 nm represents a surface coverage of about 15 ng/cm$^2$ adsorbed proteins. The detection limit of the SPR sensor used is 0.3 ng/cm$^2$.

The results are shown in FIGS. 11A-11C.

Example 7

Anti-ALCAM Immobilization and ALCAM Detection in Human Blood Samples

In this example, the immobilization of an anti-ALCAM and detection of ALCAM in human blood samples using a surface coated with a representative polymer of the invention, pCBMA$_2$-catechol$_2$, is described. The process for making and using the surface is illustrated in FIG. 12.

The carboxylate groups of the pCB surface were activated by injection of a freshly prepared solution of N-hydroxysuccinimide (NHS) (0.05 M) and N-ethyl-N-(3-diethylaminopropyl) carbodiimide hydrochloride (EDC) (0.2 M) in Milli-Q water for 7 min at 25° C. Sodium acetate buffer (10 mm), pH 5.0 at 25° C. (SA), was briefly injected to obtain a stable baseline. A solution of antibodies with an antibody concentration of 50 mg/mL in NaOH solution (pH=9.5) was flowed over spots of the activated polyCBAA surface for 14 min. The functionalized surface was washed for a short time with 10 mM phosphate buffer with 0.5 M NaCl, pH 8.2 (PBNa), to remove all noncovalently bound ligands and to deactivate the residual activated groups of pCB. The total time of deactivation was 21 min when using a buffer of pH 8-9. The SA buffer was injected again to monitor the amount of immobilized antibodies. The resulting functionalized pCB$_2$-catechol$_2$ surface is applied to detect ALCAM in 100% blood plasma. In this study, ALCAM was added into 100% plasma to obtain different concentrations up to 1000 ng/mL. The buffer solution of ALCAM was 10 mM phosphate buffer containing 0.3 M NaCl, 0.1% BSA, pH=7.4. Sample solutions were flowed over the measuring (anti-ALCAM-immobilized) surfaces for 10 min, followed by buffer injection to wash the surface. The adsorption of plasma without extra ALCAM added on the functionalized surface was used as reference.

The immobilization and detection are illustrated schematically in FIG. 12. The results are illustrated graphically in FIGS. 13A-13C.

Example 8

Preparation and Characteristics of a Representative pSB-Catechol Coated Surface

In this example, the preparation and characteristics of a representative surface of the invention (pSB-catechol-NH2-) are described. The preparation is illustrated in FIG. 14.

Synthesis of 2-Bromo-2-methyl-N-[2-(3,4-dihydroxy-phenyl)-ethyl]propionamid

2-Bromo-2-methyl-N-[2-(3,4-dihydroxy-phenyl)-ethyl] propionamide, the initiator, was synthesized through the reaction of dopamine.HCl and BIBB using a method similar to one reported previously. The product after purification was a colorless viscous liquid (1.3 g, 43%). $^1$H NMR (300 MHz, CD$_3$OD) δ: 6.68 (d, 1H, J=8.1 Hz), 6.66 (s, 1H), 6.54 (d, 1H, J=8.1 Hz), 3.36 (m, 2H), 2.67 (t, 2H, J=7.5 Hz), 1.89 (s, 6H).

SAM Preparation and Initiator Immobilization.

SPR glass chips were coated with an adhesion-promoting chromium layer (thickness 2 nm) and a surface plasmon active gold layer (48 nm) by electron beam evaporation under vacuum. Before SAM preparation, the substrates were washed with water and pure ethanol, cleaned under UV light, and washed with water and pure ethanol. SAMs were formed by soaking gold-coated substrates in pure ethanol solution of thiols at room temperature after careful cleaning. NH$_2$-SAMs were formed by soaking UV ozone-cleaned, gold coated substrates in a 0.5 mM ethanolic solution of HS(CH2)$_{11}$-NH$_2$ with 3% (v/v) N(CH$_2$CH$_3$)$_3$ overnight. The substrates were rinsed sequentially with ethanol, an ethanolic solution containing CH$_3$COOH [10% (v/v)], and ethanol, followed by drying in a stream of filtered air. The substrates were immersed in a 10 mM Tris-HCl buffer (pH=8.5) with 1 mg/mL initiator for 24 h in the dark. NH$_2$-functionalized glass chips used in the long-term bacterial adhesion experiments were prepared using 3-aminopropyltrimethoxysilane.

SBMA Polymerization.

SBMA was grafted to the surfaces via ATRP following a similar method to one reported previously. Milli-Q water and MeOH were deoxygenated by passing a continuous stream of dry N$_2$ through the solution (15 min) at room temperature. Initiator-modified samples with 2,2'-dipyridyl (210 mg, 1.34 mmol), CuBr (76.81 mg, 0.54 mmol), and CuBr$_2$ (12.04 mg, 0.05 mmol) were sealed in a glass tube, deoxygenated (three high-vacuum-pump/N$_2$ refill cycles), dissolved in MeOH (10 ml), and left at room temperature under N$_2$. SBMA (3.75 g, 26.75 mmol) was sealed in another glass tube, deoxygenated (three high-vacuum-pump/N$_2$ refill cycles), dissolved in a mixture of Milli-Q water (5 ml) and MeOH (10 ml), and left at room temperature under N$_2$. The monomer solution was then transferred into the sample tube with a syringe. Enough solution was added to submerge each sample completely. After overnight polymerization, the samples were removed, washed with warm Milli-Q water (60° C.), and dried under a stream of N$_2$. Attenuated Total Reflectance Fourier Transform Infrared (ATR-FTIR) spectra of the coated surfaces were acquired with a Bruker tensor 27 (Billerica, Mass.).

SPR and Protein Adsorption.

Protein solutions were flowed for 15 min on a custom-built SPR sensor from the Institute of Photonics and Electronics, Academy Sciences (Prague, Czech Republic). Briefly, the SPR sensor is based on the Kretschmann geometry of the attenuated total reflection (ATR) method and wavelength modulation. Solutions of fibrinogen and lysozyme in PBS (1.0 mg/mL), 10% human serum in PBS, 100% human serum, and 100% human plasma were flowed over the surfaces at a flow rate of 0.05 mL/min. A surface-sensitive SPR detector was used to monitor protein-surface interactions in real time. The wavelength shift between two buffer baselines before and after protein injection was used to measure the change in surface concentration (mass per unit area). For the SPR sensor used in the study, a 1 nm SPR wavelength shift at 750 nm represents a surface coverage of about 15 ng/cm$^2$ adsorbed proteins.

Bacterial Species and Culture Conditions.

*P. aeruginosa* (PAO1, with a GFP expressing plasmid) was first cultured in separate pure cultures overnight at 37° C. on trypticase soy broth (TSB) (BD, USA) agar plates. Cultures on agar plates can be used for 2 weeks, if kept at 4° C. Several colonies were used to inoculate 25 mL TSB (10 g/L) containing 200 µg/mL of carbenicillin. These initial cultures were incubated at 37° C. with shaking at 100 rpm for 18 h and were then used to inoculate a second culture of each species in 200 mL of appropriate medium.

Bacterial Adhesion Assay.

BST FC 281 Flow Cells, designed for monitoring and evaluation of biofilm processes using microscopy and image analysis, were purchased from BioSurface Technologies. The FC 281 Flow Cells is a dual channel, flat plate flow cell designed for use with transmitted, fluorescent, or confocal microscopy. Parallel channels allow direct side-by-side comparisons.

Standard 24 mm×60 mm glass cover slips coated with polymer films were fixed in the flow cells. Dimensions of the flow chamber were 50.5 mm (L), 12.5 mm (W), and 2 mm (deep). The flow chambers were sterilized and cleaned using a method reported previously. PBS was first pumped through the flow cell to soak the surface. When the second suspended culture reached an optical density of 1.0 at 600 nm, bacteria were collected by centrifugation at 8000 g for 10 min at 4° C. Cell pellets were washed three times with sterile PBS and subsequently suspended in PBS to a final concentration of 106 cells/mL. The cell suspension was pumped through the flow cell at a flow rate of 2.5 mL/min (shear stress of about 0.05 dyn/cm$^2$) and then flow was terminated and bacteria were allowed to adhere to the surfaces under static conditions for 30 min. After 30 min, TSB (10 g/L) with 100 µg/mL carbenicillin was pumped through the flow cell at a flow rate of 2.5 mL/min for the remainder of the experiment. The vessel, connective tubing, and parallel flow reactor were shielded from light (to prevent photobleaching of stain) using aluminum foil. The effluent was collected in a waste container for proper disposal.

The bacterial accumulation was observed in situ. Since the *P. aeruginosa* strain used in this study carries a green fluorescent protein (GFP) gene, samples could be imaged without staining. *P. aeruginosa* were observed directly with a CCD-CoolSNAP camera (Roper scientific, Inc., USA) mounted on Nikon Eclipse 80i with 100× oil lens and epifluorescent illumination through a FITC filter.

Example 9

Preparation and Characteristics of a Representative Polyampholyte-Coated Surface In this example, the preparation and characteristics of representative polyampholytes and polyampholyte-coated surfaces of the invention are described. The preparation of coated surfaces is illustrated schematically in FIG. 22. The chemical structures of representative initiators (Initiators 1 and 2) and a representative ion-pair copolymer are shown in FIG. 23.

Initiator 1

N,N'-(2-hydroxy-1,3-propanediyl)-bis[2-(N-2-bromo-2-methyl propionamide)-3-(3,4-di(t-butyldimethylsilyloxy)) phenyl]propanamide (Catechol$_2$-Br$_2$, Initiator 1) was prepared as described in Example 4.

Initiator 2

4,4'-Azobis(4-cyano-N-(2-(3,4-di(tert-butyldimethylsilyloxy))phenyl)-ethyl)-pentanamide (Initiator 2) was prepared from 4,4'-azobis(4-cyanopentanoic acid) (V501, Fluka, 0.56 g, 2 mmol) by dissolving in 40 mL 0.1 M MES [2-(N-morpholino)ethane sulfonic acid] buffer and adding an excess of 2-[3,4-di(t-butyldimethylsilyloxy)]phenethylamine dissolved in 20 mL THF. EDC [1-ethyl-3-(3-dimethylaminopropyl)carbodiimide hydrochloride] (1.92 g, 10 mmol) dissolved in 20 mL MES buffer was added under stir at room temperature. The solution mixture was stirred overnight at room temperature. The product was extracted with chloroform and applied to a silica gel chromatography (hexane/ethyl acetate (2/1), $R_f$=0.15) to provide Initiator 2 as a white powder (0.22 g, 11%). $^1$H NMR (300 MHz, CDCl$_3$), δ: 6.77 (m, 1H), 6.65 (m, 2H), 3.45 (m, 2H), 2.70 (t, 2H), 2.38 (m, 2H), 1.72 (s, 3H), 1.59 (t, 2H), 1.00 (s, 18H), 0.21 (s, 12H).

Ion-Pair Comonomer

The ion-pair monomer (2-methacryloyloxyethyltrimethylammonium 2-methacryloyloxyethanesulfonate (METMA•MES)) was synthesized as follows. To a light-shielded suspension of silver (I) oxide (10.79 g, 46.6 mmol) in 100 mL water was added slowly with stirring 2-sulfoethyl methacrylate (9.04 g, 46.6 mmol) in 10 mL water. The reaction was then continued for another 5 h at room temperature. After filtration to remove the remaining silver oxide, the filtrate was titrated by 5% wt. aqueous solution of [2-(methacryloyloxy)ethyl]trimethylammonium chloride while stirring at room temperature. The white precipitate of silver chloride formed immediately and the mixture was stirred adequately during the titration. When there was no new precipitate generated in the solution, the precipitate was filtered and the filtrate was lyophilized (15.3 g, 90%). $^1$H NMR (CDCl$_3$), δ: 1.95 (s, 6H), 3.18 (t, 2H), 3.42 (s, 9H), 4.00 (t, 2H), 4.54 (t, 2H), 4.64 (t, 2H), 5.56 (m, 1H), 5.66 (m, 1H), 6.13 (m, 2H).

Polymer I

Initiator 1 (26 mg, 0.022 mM), BPY (20 mg, 0.13 mM), and CuBr (6.50 mg, 0.045 mM) were placed into a three-necked flask, and the system was degassed three times and filled with N$_2$, then 2 mL DMF (degassed) was added under N$_2$. The mixture was stirred for 20 mins at 60° C. Ion pair monomer (0.44 g, 1.20 mM), dissolved in DMF (degassed, 3 mL) was added into the reaction system and the polymerization continued for 24 hrs at 60° C. The resulting polymer, precipitated by acetone, was collected by filtration. After dissolving in water, the polymer solution was dialyzed for 5 days with DI water. Polymer I (white powder, 0.31 g, 70%, Mn 19143, PDI 1.5) was obtained after lyophilization.

Polymer II

Initiator 2 (27.8 mg, 0.028 mM) and ion pair monomer (0.5 g, 1.37 mM) were placed into three-necked flask, and the system was degassed three times and filled with N$_2$, then 5 mL DMF (degassed) was added under N$_2$. The mixture was stirred for 10 mins, then heated to 60° C. The polymerization continued for 24 hrs at 60° C. The resulting polymer, precipitated by acetone, was collected by filtration. After dissolving in water, the polymer solution was dialyzed for 5 days with DI water. Polymer II (white powder, 0.33 g, 66%, Mn 28276, PDI 1.8) was obtained after lyophilization.

Polymer Characterization

Molecular weights of the polymers were determined using aqueous gel permeation chromatography (GPC) (Waters 2695 Separations Module) fitted with a Waters 2414 refractive index detector and two Waters ultrahydrogel columns in series (ultrahydrogel 250 and ultrahydrogel 1000, 7.8 mm×300 mm). The buffer solution (0.1 M $K_2HPO_4$—$KH_2PO_4$ buffer, pH 7.4) was used as the eluent with a flow rate of 0.7 mL/min at 50° C. All samples were filtered through 0.2 micron PTFE filters prior to injection. The system was calibrated with narrow molecular weight polyethylene oxide standards.

Polymer Deprotection

Before surface adhesion, the TBDMS groups of protected Polymer I and Polymer II were removed using TBAF in order to achieve complete deprotection. A solution with 1.0 mM TBDMS protected polymer and 10 mM TBAF in THF was stirred overnight. The suspension was centrifuged and the supernatant was removed. The remaining white powder was washed three times with THF and dried under reduced pressure.

Surface Modification 6 mg deprotected polymer was dissolved in 2 mL DI water (pH=3) in a 20 mL glass tube, and 1 mL THF was added dropwise into this tube. The solution was then transferred to a Teflon cell. Cleaned Au chips were placed into the cell and submerged for 24 hrs. The chip was washed with DI water and dried with airflow before use.

Film Thickness by Ellipsometer

Alpha-SE spectroscopic ellipsometer (J.A. Woollam Co., Inc.) was used to measure film thickness.

Surface Characterization by ATR-FTIR

Attenuated total reflectance Fourier transform infrared (ATR-FTIR) spectra of the coated surfaces were acquired with a Bruker tensor 27 instrument (Billerica, Mass.).

Composition by Electron Spectroscopy for Chemical Analysis (ESCA)

Samples coated with Polymer I and Polymer II were prepared as described above. The samples were rinsed extensively with 18.2 MΩ cm water, dried with filtered air, and placed in a desiccator overnight before analysis. ESCA spectra were taken on a Surface Science Instruments S-probe spectrometer with monochromatized Al Kα X-rays. The spot size for these acquisitions was about 800 μm. The pass energy for the survey spectra was 150 eV. Detailed scans were completed with identical pass energy for both N and S peaks to accurately quantify any small amounts of those elements. The ESCA 2000 A Analysis software v. 102.04 (Service Physics, Bend, Oreg.) was used for peak integration.

Protein Adsorption by SPR

Protein adsorption was measured with a four-channel SPR sensor (Institute of Radio Engineering and Electronics, Academy of Sciences, Prague, Czech Republic) based on the Kretschmann geometry of the attenuated total reflection method and wavelength modulation. Coated chips were rinsed extensively with 18.2 MΩ cm $H_2O$, dried with filtered air, and then mounted to a coupling prism using refractive index matching fluid (Cargille, Cedar Grove, N.J.). A baseline signal was established by flowing PBS at a rate of 50 μL/min through the sensor for 10 min. Following this, fresh 1 mg/mL protein solutions of Fg, Lyz, and BSA were flowed through independent channels for 10 min to measure the adsorption of these proteins to the polymer brush-coated surfaces. To remove unbound protein molecules and to reestablish the baseline, PBS buffer was flowed for an additional 10 min. Protein adsorption was quantified by measuring the change in wavelength in the buffer baseline before and after the injection of protein solutions. The shift was converted to an adsorbed amount. For the SPR sensor used, a 1 nm shift in wavelength starting at 750 nm represents a surface coverage of about 15 ng/cm² of adsorbed protein.

While illustrative embodiments have been illustrated and described, it will be appreciated that various changes can be made therein without departing from the spirit and scope of the invention.

The embodiments of the invention in which an exclusive property or privilege is claimed are defined as follows:

1. A polymer, comprising:
   (a) polymer backbone;
   (b) a plurality of cationic centers, each cationic center covalently coupled to the polymer backbone by a first linker;
   (c) an anionic center covalently coupled to each cationic center by a second linker; and
   (d) one or more dihydroxyphenyl groups covalently coupled to the terminus of the polymer backbone.

2. The polymer of claim 1, wherein the cationic center is selected from the group consisting of ammonium, imidazolium, triazolium, pyridinium, morpholinium, oxazolidinium, pyrazinium, pyridazinium, pyrimidinium, piperazinium, pyrrolidinium, and phosphonium.

3. The polymer of claim 1, wherein the anionic center is selected from the group consisting of a carboxylic acid group ($CO_2^-$), a sulfuric acid group ($SO_4^{-2}$), a sulfonic acid group ($SO_3^-$), a sulfinic acid group ($SO_2^-$), a phosphonic acid group ($PO_4^{-2}$), and a phosphinic acid group ($PO_3^-$).

4. The polymer of claim 1, wherein the dihydroxyphenyl group is a 3,4-dihydroxyphenyl group.

5. The polymer of claim 1 having the formula:

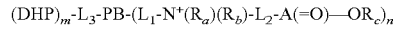

wherein

PB is the polymer backbone having n pendant groups $L_1$-$N^+(R_a)(R_b)$-$L_2$-A(=O)—$OR_c$ and m dihydroxyphenyl groups covalently coupled to the polymer backbone through a linker moiety $L_3$;

DHP is a dihydroxyphenyl group;

$N^+$ is the cationic center;

$R_a$ and $R_b$ are independently selected from alkyl and aryl, or taken together with the nitrogen to which they are attached form a cationic center;

A(=O)—$OR_c$ is the anionic center, wherein $R_c$ is hydrogen or a counterion, and wherein A is selected from the group consisting of C, S, SO, P, or PO;

$L_1$ is a linker that covalently couples the cationic center to the polymer backbone;

$L_2$ is a linker that covalently couples the cationic center to the anionic center;

$L_3$ is a linker moiety that covalently couples the m dihydroxyphenyl groups to the polymer backbone;

n is an integer from 1 to about 1,000; and m is from 1 to 20.

6. The polymer of claim 5, wherein $R_a$ and $R_b$ are independently selected from the group consisting of C1-C5 straight chain and branched alkyl groups.

7. The polymer of claim 5, wherein $L_1$ is selected from the group consisting of —C(=O)O—$(CH_2)_n$— and —C(=O)NH—$(CH_2)_n$—, wherein n is an integer from 1 to 10.

8. The polymer of claim 5, wherein $L_2$ is —$(CH_2)_n$—, where n is an integer from 1 to 5.

9. The polymer of claim 5, wherein A is selected from the group consisting of C, SO, and $PO_2$.

10. The polymer of claim 5, wherein n is from about 10 to about 500.

11. The polymer of claim 5, wherein m is 1 or 2.

12. A surface of a substrate coated with a plurality of polymers of claim 1.

13. A method for treating a surface comprising applying a polymer of claim 1 to the surface.

* * * * *